United States Patent
Waters et al.

(10) Patent No.: US 7,510,851 B2
(45) Date of Patent: Mar. 31, 2009

(54) COMPOSITIONS AND METHODS FOR DIAGNOSING AND TREATING DIABETES, INSULIN RESISTANCE AND DYSLIPIDEMIA

(75) Inventors: Steve Waters, San Ramon, CA (US); Shonna Moodie, San Francisco, CA (US); Brian Lavan, San Francisco, CA (US); Thomas A. Gustafson, Danville, CA (US)

(73) Assignee: Metabolex, Inc., Hayward, CA (US)

( * ) Notice: Subject to any disclaimer, the term of this patent is extended or adjusted under 35 U.S.C. 154(b) by 874 days.

(21) Appl. No.: 10/321,204

(22) Filed: Dec. 16, 2002

(65) Prior Publication Data

US 2003/0186871 A1    Oct. 2, 2003

Related U.S. Application Data

(60) Provisional application No. 60/341,451, filed on Dec. 17, 2001.

(51) Int. Cl.
C12Q 1/26 (2006.01)
C12Q 1/00 (2006.01)
C12Q 1/68 (2006.01)
C12N 9/02 (2006.01)
C12N 1/20 (2006.01)
C12N 5/00 (2006.01)
C07H 21/04 (2006.01)
C12N 15/00 (2006.01)
C12Q 21/04 (2006.01)

(52) U.S. Cl. .............. 435/25; 435/4; 435/6; 435/69.1; 435/71.1; 435/325; 435/252.3; 435/320.1; 435/440; 435/189; 536/23.2

(58) Field of Classification Search ................. 435/189, 435/4, 6, 25, 252.3, 320.1, 69.1, 71.1, 440; 536/23.2; 514/789
See application file for complete search history.

(56) References Cited

U.S. PATENT DOCUMENTS

| 4,593,092 | A  | * | 6/1986  | Irikura et al. ................. 544/6 |
| 5,756,299 | A  |   | 5/1998  | Hillman |
| 6,001,353 | A  |   | 12/1999 | Gibori |
| 6,368,597 | B1 |   | 4/2002  | Strassmann |
| 2002/0164847 | A1 | | 11/2002 | Climbora |

FOREIGN PATENT DOCUMENTS

WO    WO 97/11162 A1    3/1997
WO    WO 01/79223 A2    10/2001

OTHER PUBLICATIONS

Dufort et al. Molecular cloning of human type 3 3 alpha-hydroxysteroid dehydrogenase that differs from 20 alpha-hydroxysteroid dehydrogenase by seven amino acids.Biochem Biophy Res Commun. Nov. 12, 1996;228(2):474-9.*

(Continued)

*Primary Examiner*—Yong D Pak
(74) *Attorney, Agent, or Firm*—Townsend and Townsend and Crew LLP

(57) ABSTRACT

The present invention provides compositions and methods for diagnosing and treating diabetes, insulin resistance and dyslipidemia. In particular, the invention provides methods of identifying modulators of AKR1C as well as methods of diagnosing diabetes by measuring the levels of AKR1C or $9\alpha$, $11\beta$-$PGF_{2\alpha}$ in a patient.

20 Claims, 7 Drawing Sheets

OTHER PUBLICATIONS

Sequence Alignment—Dufort et al.*
Guo et al. Proc Natl Acad Sci USA. Jun. 22, 2004;101(25):9205-10.*
Kashiba et al. Impaired reductive regeneration of ascorbic acid in the Goto-Kakizaki diabetic rat. Biochem J. Oct. 15, 2000;351 Pt 2:313-8.*
Penning et al. Human 3alpha-hydroxysteroid dehydrogenase isoforms (AKR1C1-AKR1C4) of the aldo-keto reductase superfamily: functional plasticity and tissue distribution reveals roles in the inactivation and formation of male and female sex hormones. Biochem J. Oct. 1, 2000;351(Pt 1):67-77.*
Silverman et al. New assay technologies for high-throughput screening. Curr Opin Chem Biol. Jun. 1998;2(3):397-403. Review.*
Yabe-Nishimura et al. Aldose reductase in glucose toxicity: a potential target for the prevention of diabetic complications. Pharmacol Rev. Mar. 1998;50(1):21-33.*
Stolz, Andrew et al.; "cDNA Cloning and Expression of the Human Hepatic Bile Acod-binding Protein"; 1993, *The Journal of Biological Chemistry*, vol. 268, No. 14, pp. 10448-10457.

* cited by examiner

FIGURE 6

```
CLUSTAL W (1.8) multiple sequence alignment
Alignment of mouse orthologs with human AKR1C sequences.

AB059565    MNSKIQKIELNDGHSIPVLGFGTYATEEHLKKKSMESTKIAIDVGFCHIDCSHLYQNEEE
BC013482    MNSVSPRVVLNDCHFIPALGFGTTVPDKVPKDELIKATKIAIDTGFRHFDSAYLYQIEEE
D45850      MDSKQQTVRLSDGHFIPILGFGTYAPQEVPKSKATEATKIAIDAGFRHIDSASMYQNEKE
BC021607    MNSKQQTVLLNDGHFIPILGFGTSAPQEVPRSKATEATKIAIDAGFRHIDCAAVYQNEKE
BC013531    MNSKCHCVILNDGNFIPVLGFGTALPVECPKSKAKELTKIAIDAGFHHFDSASVYNTEDR
AKR1C1      MDSKYQCVKLNDGHFMPVLGFGTYAPAEVPKSKALEATKLAIEAGFRHIDSAHLYNNEEQ
AKR1C2      MDSKYQCVKLNDGHFMPVLGFGTYAPAEVPKSKALEAVKLAIEAGFHHIDSAHVYNNEEQ
AKR1C3      MDSKQQCVKLNDGHFMPVLGFGTYAPPEVPRSKALEVSKLAIEAGFRHIDSAHLYNNEEQ
AKR1C4      MDPKYQRVELNDGHFMPVLGFGTYAPPEVPRNRAVEVTKLAIEAGFRHIDSAYLYNNEEQ
AB027125    MSSKQHCVKLNDGHLIPALGFGTYKPKEVPKSKSLEAACLALDVGYLHVDTAYAYQVEEE
AB027237    MSSKQHYVKLNDGHLIPALGFGTYKPKEVPKSKSLEAACLALDVGYRHVDTAYAYQVEEE
U68535      MEN-----------IPTVGLGTWKAS---PGEVTDAVKLAINLGYRHFDCAYLYHNESE
              *.             :* :*:**   .        .  :*::  *: *.*  :  *: *..

AB059565    IGQAILSKIEDGTVKREDIFYTSKLWSTSHRPELVRPSLENSLRKLNLDYVDLYLIHFPV
BC013482    VGQAIRSKIEDGTVKREDIFYTSKLWSTFHRPELVRSCLEKTLKNAQLDYVDLYIIHFPM
D45850      VGLAIRSKIADGTVKREDIFYTSKVWCTFHRPELVRVCLEQSLKQLQLDYVDLYLIHFPM
BC021607    VGLAIRSKIVDGTVKREDIFCTSKVWQTFHRPELVQVCLEQSLKQLQLDYVDLYLIHFPI
BC013531    VGEAIRSKIADGTVRREDIFYTSKVWCTSLRPELVRASLVRSLQKLQFDYVDLYLIHYPM
AKR1C1      VGLAIRSKIADGSVKREDIFYTSKLWCNSHRPELVRPALERSLKNLQLDYVDLYLIHFPV
AKR1C2      VGLAIRSKIADGSVKREDIFYTSKLWSNSHRPELVRPALERSLKNLQLDYVDLYLIHFPV
AKR1C3      VGLAIRSKIADGSVKREDIFYTSKLWSTSHRPELVRPALENSLKKAQLDYVDLYLIHSPM
AKR1C4      VGLAIRSKIADGSVKREDIFYTSKLWCTFFQPQMVQPALESSLKKLQLDYVDLYLLHFPM
AB027125    IGQAIQSKIKAGVVKREDLFITTKLWCTCFRPELVKPALEKSLKKLQLDYVDLYIMHYPV
AB027237    IGQAIQSKIKAGVVKREDLFVTTKLWCGCFRPELVKPALEKSLKSLQLDYVDLYLIHYPV
U68535      VGMGISEKIKEGVVKREDLFVVSKLWCTCHKKSLVKTACTNTLEALNLDYLDLYLIHWPI
             :* .* .** * *:***:* .:*:*        :  ..*: .   :*.   ::**:***:* *:

AB059565    SLKPGNELLPKDEHGNLIFDTVDLCDTWEAMEKCKDAGLAKSIGVSNFNRRQLEMILNKP
BC013482    ALQPGDKLFPRDEHGKLLAEAVDLCDTWEAMEKCKDAGLAKSIGVSNFNFRQLETILNKP
D45850      AMKPGENYLPKDENGKLIYDAVDICDTWEAMEKCKDAGLAKSIGVSNFNRRQLEKILKKP
BC021607    AMKPGENYFPKDENGKFIYDAVDICDTWEAMEKCKDAGLAKSIGVCNFNRRQLEKILSKP
BC013531    ALKPGEENFPVDEHGKLIFDRVDLCATWEAMEKCKDAGLTKSIGVSNFNSRQLEMILNKP
AKR1C1      SVKPGEEVIPKDENGKILFDTVDLCATWEAVEKCKDAGLAKSIGVSNFNRRQLEMILNKP
AKR1C2      SVKPGEEVIPKDENGKILFDTVDLCATWEAMEKCKDAGLAKSIGVSNFNHRLLEMILNKP
AKR1C3      SLKPGEELSPTDENGKVIFDIVDLCTTWEAMEKCKDAGLAKSIGVSNFNRRQLEMILNKP
AKR1C4      ALKPGETPLPKDENGKVIFDTVDLCATWEVMEKCKDAGLAKSIGVSNFNCRQLEMILNKP
AB027125    PMKSGDNDFPVNEQGKSLLDTVDFCDTWERLEECKDAGLVKSIGVSNFNHRQLERILNKP
AB027237    PMKPGDNESPLDENGKFLLDTVDFCDTWERLEECKDAGLVKSIGVSNFNHRQLERILNNP
U68535      GFKPGEKDIPLDRNGKVIPSHTSFLDTWEAMEDLVFEGLVKNLGVSNFNHEQLERLLDKP
             .:.*:    * :..:*:  : . ...: *** :*.    **.*.:**.*** . ** :*.:*

AB059565    GLKYKPVCNQVECHLYLNQSKLLAYCKMNDIVLVAYGALGTQRYKYCINEDTPVLLDDPV
BC013482    GLKYKPVCNQVECHLYLNQSQMLDYCKSKDIILVSYCTLGSSRDKIWVDQKSPVLLDDPV
D45850      GLKYKPVCNQVECHPYLNQGKLLDFCRSKDIVLVAYSALGSHREKQWVDQSSPVLLDNPV
BC021607    GLKYKPVCNQVECHPYLNQRKLLDFCRSKDIVLAHSALGSNRDKEWVDKSFPVLLDDPV
BC013531    GLKYKPVCNQVECHPYLNQMKLLDFCKSKDIVLVAYGVLGTQRYGWVDQNSPVLLDEPV
AKR1C1      GLKYKPVCNQVECHPYFNQRKLLDFCKSKDIVLVAYSALGSHREEPWVDPNSPVLLEDPV
AKR1C2      GLKYKPVCNQVECHPYFNQRKLLDFCKSKDIVLVAYSALGSHREEPWVDPNSPVLLEDPV
AKR1C3      GLKYKPVCNQVECHPYFNRSKLLDFCKSKDIVLVAYSALGSQRDKRWVDPNSPVLLEDPV
AKR1C4      GLKYKPVCNQVECHPYLNQSKLLDFCKSKDIVLVAHSALGTQRHKLWVDPNSPVLLEDPV
AB027125    GLKYKPVCNQVECHLYLNQRKLLDYCESKDIVLVAYGALGTQRYKKWVDQNSPVLLNDPV
AB027237    GLKYKPVCNQVECHLYLNQSKLLDYCKSKDIVLVAYGALGTQRYKEWVDQNSPVLLNDPV
U68535      GLRVRPITNQIECHPYLNQKKLIDFCHKRNVSVTAYRPLGGSG-------GGFHLMDDTV
             **: :*: **:*** *:*: ::: :*.  .:: ::  **            *:::.*
```

FIGURE 6 continued

```
AB059565    LCAMAKKYKRTPALIALRYQLDRGIVALAKSFNEERIRENMQVFDFQLASDDMKILDGLD
BC013482    LCAMANKYKQTPALIAIRYQLQRGIVVLTRSFKEKRIKEFMKVPEFQLASEDMKVLDGLH
D45850      LGSMAKKYNRTPALIALRYQLQRGVVVLAKSFSEKRIKENMQVFEFQLTSEDMKVLDDLN
BC021607    LGSMAKKYNRTPALIALRYQVQRGVVVLAKSPIEKRIKENMQVFEFQLTSVDMKVLDGLN
BC013531    LGSMAKKYNRTPALIALRYQLQRGIVVLNTSLKEERIKENMQVFEFQLSSEDMKVLDGLN
AKR1C1      LCALAKKHKRTPALIALRYQLQRGVVVLAKSYNEQRIRQNVQVFEFQLTSEEMKAIDGLN
AKR1C2      LCALAKKHKRTPALIALRYQLQRGVVVLAKSYNEQRIRQNVQVFEFQLTSEEMKAIDGLN
AKR1C3      LCALAKKHKRTPALIALRYQLQRGVVVLARSYNEQRIRQNVQVFEFQLTAEDMKAIDGLD
AKR1C4      LCALAKKHKRTPALIALRYQLQRGVVVLAKSYNEQRIRENIQVFEFQLTSEDMKVLDGLN
AB027125    LCDVAKKNKRSPALIALRYLIQRGIVPLAQSFKENEMRENLQVFGFQLSPEDMKTLDGLN
AB027237    LCDVAKRNKRSPALIALRYLFQRGIVPLAQSFKENEMRENLQVFEFQLSPEDMKTLDGLN
U68535      IRKIAKKHGKSPAQILIRFQIQRNLIVIPKSVTPSRIRENIQVFDFELTEKDMEELLSLD
            : :*::   ::** * :*: ..*.:: :  *     ..:::  ::** *:*:  :*: : .*.

AB059565    RNLRYFPADMFKAHPNFPFFDEY
BC013482    RNLRYNTASYFDDHPNHPFTDEY
D45850      KNIRYISGSSPKDHPDFPFWDEY
BC021607    KNIRYIGSSISEDHPDFPFLDEY
BC013531    RNMRYIPAAIFKGHPNWPFLDEY
AKR1C1      RNVRYLTLDIFAGPPNYPFSDEY
AKR1C2      RNVRYLTLDIFAGPPNYPFSDEY
AKR1C3      RNLHYFNSDSFASHPNYPYSDEY
AKR1C4      RNYRYVVMDFVMDHPDYPFSDEY
AB027125    KNFRYLPAEFLVDHPEYPFVEEY
AB027237    KNFRYLPAEFLADHPEYPFSEEY
U68535      KNLRFATFPTTENHQDYPFHIEY
            :* ::          : *:  **
```

COMPOSITIONS AND METHODS FOR DIAGNOSING AND TREATING DIABETES, INSULIN RESISTANCE AND DYSLIPIDEMIA

CROSS REFERENCE TO RELATED APPLICATIONS

This application claims priority to U.S. Provisional Patent Application No. 60/341,451, filed Dec. 17, 2001, which is incorporated in its entirety for any and all purposes.

FIELD OF THE INVENTION

This invention relates to methods of diagnosing and treating diabetes.

BACKGROUND OF THE INVENTION

Diabetes mellitus can be divided into two clinical syndromes, Type 1 and Type 2 diabetes mellitus. Type 1, or insulin-dependent diabetes mellitus (IDDM), is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the level required for euglycemia (normal blood glucose level). Although the exact trigger for this immune response is not known, patients with IDDM have high levels of antibodies against pancreatic beta cells. However, not all patients with high levels of these antibodies develop IDDM.

Type 2 diabetes (also referred to as non-insulin dependent diabetes mellitus (NIDDM)) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type 2 diabetes.

Type 2 diabetes is brought on by a combination of poorly understood genetic and acquired risk factors—including a high-fat diet, lack of exercise, and aging. Worldwide, Type 2 diabetes has become an epidemic, driven by increases in obesity and a sedentary lifestyle, widespread adoption of western dietary habits, and the general aging of the populations in many countries. In 1985, an estimated 30 million people worldwide had diabetes—by 2000, this figure had increased 5-fold, to an estimated 154 million people. The number of people with diabetes is expected to double between now and 2025, to about 300 million.

Type 2 diabetes is a complex disease characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. As discussed above, one of the principal underlying causes of diabetes is thought to be an increase in insulin resistance in peripheral tissues, principally muscle and fat. Therefore, an important therapeutic goal in the treatment of diabetes is therefore to decrease peripheral insulin resistance. The present invention addresses this and other problems.

BRIEF SUMMARY OF THE INVENTION

This invention provides methods for identifying an agent for treating a patient having diabetes or a predisposition for diabetes. In some embodiments, the methods comprise: (i) contacting a solution comprising an aldo-keto reductase 1C (AKR1C) polypeptide or fragment thereof with the agent, wherein the AKR1C polypeptide or the fragment thereof catalyzes the interconversion of $9\alpha,11\beta$-P-$PGF_{2\alpha}$ from prostaglandin D2, and the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51; and (ii) selecting an agent that modulates the expression or catalytic activity of the AKR1C polypeptide or fragment thereof, thereby identifying an agent for treating a patient having diabetes or a predisposition for diabetes.

This invention provides methods for identifying an agent that modulates insulin sensitivity. In some embodiments, the methods comprise: (i) contacting a solution comprising an aldo-keto reductase 1C (AKR1C) polypeptide or fragment thereof with the agent, wherein the AKR1C polypeptide or the fragment thereof catalyzes the interconversion of $9\alpha,11\beta$-$PGF_{2\alpha}$ from prostaglandin D2, and the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51; and (ii) selecting an agent that modulates the expression or catalytic activity of the AKR1C polypeptide or fragment thereof, thereby identifying an agent that modulates insulin sensitivity.

This invention provides methods for identifying an agent that modulates PPAR activity. In some embodiments, the methods comprise: (i) contacting a solution comprising an aldo-keto reductase 1C (AKR1C) polypeptide or fragment thereof with the agent, wherein the AKR1C polypeptide or the fragment thereof catalyzes the interconversion of $9\alpha,11\beta$-$PGF_{2\alpha}$ from prostaglandin D2, and the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51; and (ii) selecting an agent that modulates the expression or catalytic activity of the AKR1C polypeptide or fragment thereof, thereby identifying an agent that modulates PPAR activity.

In some embodiments, the predisposition for diabetes is manifested by reduced insulin sensitivity. In some embodiments, the methods further comprise selecting an agent that modulates insulin sensitivity. In some embodiments, the catalytic activity of the AKR1C polypeptide is determined by measuring a change in the level of a catalytic product or substrate. In some embodiments, the catalytic product or substrate is $9\alpha,11\beta$-$PGF_{2\alpha}$. In some embodiments, the catalytic product or substrate is prostaglandin D2. In some embodiments, the contacting step is performed in vitro. In some embodiments, the AKR1C polypeptide or fragment thereof is expressed in a cell and the cell is contacted with the agent.

In some embodiments, the agent increases the catalytic activity of the AKR1C polypeptide or fragment thereof. In some embodiments, the agent decreases the catalytic activity of the AKR1C polypeptide or fragment thereof. In some embodiments, the agent increases the expression of the AKR1C polypeptide or fragment thereof. In some embodiments, the agent decreases the expression of the AKR1C polypeptide or fragment thereof.

In some embodiments, the methods further comprise the steps of administering the agent to an animal having diabetes and testing the animal for changes in the diabetic state. In some embodiments, the methods further comprise the steps of administering the agent to an animal exhibiting insulin resistance and testing the animal for modulated insulin resistance. In some embodiments, the methods further comprise the steps of contacting a cell expressing an AKR1C polypeptide or fragment thereof with the agent and testing the cell for modulated insulin resistance. In some embodiments, the methods further comprise the steps of contacting a cell expressing an AKR1C polypeptide or fragment thereof with the agent and testing the cell for modulated PPAR activity.

In some embodiments, the amino acid sequence comprises SEQ ID NO:1. In some embodiments, the amino acid sequence comprises SEQ ID NO:7. In some embodiments, the amino acid sequence comprises SEQ ID NO:17. In some embodiments, the amino acid sequence comprises SEQ ID NO:23. In some embodiments, the amino acid sequence comprises SEQ ID NO:30. In some embodiments, the amino acid sequence comprises SEQ ID NO:31. In some embodiments, the amino acid sequence comprises SEQ ID NO:32. In some embodiments, the amino acid sequence comprises SEQ ID NO:33. In some embodiments, the amino acid sequence comprises SEQ ID NO:34. In some embodiments, the amino acid sequence comprises SEQ ID NO:35. In some embodiments, the amino acid sequence comprises SEQ ID NO:36.

The invention also provides methods of treating an animal having diabetes, a predisposition for diabetes, insulin resistance or dyslipidemia. In some embodiments, the methods comprise administering a therapeutically effective amount of an agent identified by the method described above. In some embodiments, the animal is a human.

The invention also provides methods of diagnosing Type 2 diabetes or a predisposition for Type 2 diabetes in a patient. In some embodiments, the methods comprise detecting in a sample from the patient the level of an AKR1C polypeptide or fragment thereof, wherein the AKR1C polypeptide or the fragment thereof catalyzes the interconversion of $9\alpha,11\beta$-PGF$_{2\alpha}$ from prostaglandin D2, and the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51, wherein an increased level of the polypeptide in the sample compared to a level of the polypeptide in either a non-diabetic individual or a previous sample from the patient indicates that the patient is diabetic or is predisposed for at least some pathological aspects of diabetes. In some embodiments, the detecting step comprises contacting the sample with an antibody that specifically binds to an AKR1C polypeptide or fragment thereof, wherein the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51.

In some embodiments, the amino acid sequence comprises SEQ ID NO:1. In some embodiments, the amino acid sequence comprises SEQ ID NO:7. In some embodiments, wherein the amino acid sequence comprises SEQ ID NO:17. In some embodiments, the amino acid sequence comprises SEQ ID NO:23.

The invention also provides methods of diagnosing Type 2 diabetes or a predisposition for Type 2 diabetes in a patient, comprising detecting in a sample from the patient the level of a polynucleotide encoding an AKR1C polypeptide or fragment thereof, wherein the AKR1C polypeptide or the fragment thereof catalyzes the interconversion of $9\alpha,11\beta$-PGF$_{2\alpha}$ from prostaglandin D2, and the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs:30, 31, 32, 33, 34, 35, 36, 37, 39, 41, 43, 45, 47, 49, and 51, wherein an increased level of the polynucleotide in the sample compared to a level of the polynucleotide in either a non-diabetic individual or a previous sample from the patient indicates that the patient is diabetic or is predisposed for at least some pathological aspects of diabetes. In some embodiments, the detecting step comprises quantifying mRNA encoding an AKR1C polypeptide or fragment thereof, wherein the AKR1C polypeptide or the fragment thereof catalyzes the interconversion of $9\alpha,11\beta$-PGF$_{2\alpha}$ from prostaglandin D2, and the AKR1C polypeptide or fragment thereof is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51. In some embodiments, the mRNA is reverse transcribed and amplified in a polymerase chain reaction.

In some embodiments, the amino acid sequence comprises SEQ ID NO:1. In some embodiments, the amino acid sequence comprises SEQ ID NO:7. In some embodiments, wherein the amino acid sequence comprises SEQ ID NO:17. In some embodiments, the amino acid sequence comprises SEQ ID NO:23.

In some embodiments, the methods of diagnosing Type 2 diabetes or a predisposition for Type 2 diabetes in a patient comprise detecting in a sample from the patient the level of an AKR1C enzymatic substrate or product, wherein a modulated level of the AKR1C enzymatic substrate or product in the sample compared to a level of the AKR1C enzymatic substrate or product in either a non-diabetic individual or a previous sample from the patient indicates that the patient is diabetic or is predisposed for at least some pathological aspects of diabetes. In some embodiments, the AKR1C enzymatic product or substrate is selected from the group consisting of prostaglandin D2 and $9\alpha,11\beta$-PGF$_{2\alpha}$. In some embodiments, the AKR1C enzymatic substrate or product in the sample is increased compared to a level of the AKR1C enzymatic substrate or product in either a non-diabetic individual or a previous sample from the patient. In some embodiments, the AKR1C enzymatic substrate or product in the sample is decreased compared to a level of the AKR1C enzymatic substrate or product in either a non-diabetic individual or a previous sample from the patient. In some embodiments, the detecting step comprises contacting the sample with an antibody that specifically binds to the AKR1C enzymatic substrate or product. In some embodiments, the biological sample is treated to convert the AKR1C enzymatic substrate or product into a derivative of the AKR1C enzymatic substrate or product and the level of the derivative is determined.

In some embodiments, methods of diagnosing Type 2 diabetes or a predisposition for Type 2 diabetes in a patient comprise, detecting the AKR1C enzymatic activity in a biological sample from the patient, wherein an increased enzymatic activity in the sample compared to the activity in a non-diabetic individual indicates that the patient is diabetic or is predisposed for at least some pathological aspects of diabetes.

In some embodiments, the methods comprise detecting in a biological sample a polynucleotide that either: encodes an AKR1C polypeptide or is genetically linked in the human genome to the polynucleotide encoding an AKR1C polypeptide, wherein the AKR1C polypeptide catalyzes the interconversion of $9\alpha,11\beta$-$PGF_{2\alpha}$ from prostaglandin D2, and the AKR1C polypeptide is encoded by a nucleic acid that hybridizes under stringent conditions to a nucleic acid encoding a polypeptide having an amino acid sequence selected from the group consisting of SEQ ID NO:1, SEQ ID NO:7, SEQ ID NO:17, SEQ ID NO:23, SEQ ID NO:30, SEQ ID NO:31, SEQ ID NO:32, SEQ ID NO:33, SEQ ID NO:34, SEQ ID NO:35; and SEQ ID NO:36 and wherein the polynucleotide is associated with Type 2 diabetes. In some embodiments, the polynucleotide comprises a single nucleotide polymorphism.

DEFINITIONS

An "AKR1C nucleic acid" or "AKR1C polynucleotide sequence" of the invention is a subsequence or full-length polynucleotide sequence of a gene that encodes an AKR1C polypeptide. Exemplary AKR1C nucleic acids of the invention include sequences substantially identical to AKR1C1 (see, e.g., Hara, A., et al. *Biochem. J.* 313:373-376 (1996)), AKR1C2 (see, e.g., Stolz, A., et al. *J. Biol. Chem.* 268:10448-10457 (1993); Deyashiki, Y., et al. *Biochem. J.* 299:545-552 (1994); Dufort, I., et al. *Biochem. Biophys. Res. Commun.* 228:474-479 (1996)), AKR1C3 (see, e.g., Khanna, M., et al. *J. Biol. Chem.* 270:20162-20168 (1995); Lin, H. -K., et al. *Mol. Endocrinol.* 11:1971-1984 (1997)), or AKR1C4(see, e.g., Deyashiki, Y., et al. *Biochem. J.* 299:545-552 (1994); Khanna, M., et al. J. Biol. Chem. 270:20162-20168 (1995)). Exemplary AKR1C polynucleotides encode, e.g., SEQ ID NO:1, SEQ ID NO:7, SEQ ID NO:17, and SEQ ID NO:23, respectively. Other orthologs of AKR1C3 include, e.g., SEQ ID NOs:30-36. Examples of AKR1C nucleic acids include nucleic acids substantially identical to SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:38, SEQ ID NO:40, SEQ ID NO:42, SEQ ID NO:44, SEQ ID NO:46, SEQ ID NO:48, SEQ ID NO:50, or SEQ ID NO:52. Similarly, "AKR1C polypeptide" or "AKR1C" refers to a polypeptide, or fragment thereof, that is substantially identical to a polypeptide encoded by AKR1C1, AKR1C2, AKR1C3, or AKR1C4 (e.g., SEQ ID NO:1, SEQ ID NO:7, SEQ ID NO:17, SEQ ID NO:23 and SEQ ID NOs: 30-36) or peptidomimetic compositions with substantially the same activity as SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51. In some embodiments, the AKR1C polypeptides have aldo-keto reductase class 1 C activity (also referred to as "AKR1C activity").

"AKR1C activity" refers to an enzymatic activity that converts prostaglandin D2 (also referred to as "PGD2") to $9\alpha,11\beta$-prostaglandin $F_{2\alpha}$ (also referred to as "$11\beta$-$PGF_{2\alpha}$"), the reverse reaction that converts $9\alpha,11\beta$-prostaglandin $F_{2\alpha}$ to prostaglandin D2, and other activity associated with aldo-keto reductase class C activity. See, e.g., reaction 3 in FIG. 1. Since it is understood that AKR1C polypeptides can catalyze reversible reactions, the terms "substrate" and "product" are understood to be interchangeable depending on the direction of the reaction in question. Thus, while this document refers to PGD2 as a substrate and $9\alpha,11\beta$-prostaglandin $F_{2\alpha}$ as a product, under appropriate conditions AKR1C polypeptides can catalyze the synthesis of PGD2 using $9\alpha,11\beta$-prostaglandin $F_{2\alpha}$ as a substrate. Enzymatic activity can be measured according to any methods known to those of skill in the art. Common measurements include the rate of catalysis or the ability of a sample to convert PGD2 into $9\alpha,11\beta$-$PGF_{2\alpha}$ or PGD2 into $9\alpha,11\beta$-$PGF_{2\alpha}$.

An "agonist of AKR1C" refers to an agent that binds to AKR1C, stimulates, increases, activates, facilitates, enhances activation, sensitizes or up regulates the activity or expression of AKR1C.

An "antagonist of AKR1C" refers to an agent that binds to, partially or totally blocks stimulation, decreases, prevents, delays activation, inactivates, desensitizes, or down regulates the activity or expression of AKR1C.

"PPAR activity" refers to the ability of a PPAR family member (e.g., PPAR alpha, beta or gamma) to activate transcription in response to ligand binding. PPAR activity can be measured, e.g., in cell-based assays comprising a PPAR family member and a polynucleotide comprising a PPAR binding sequence and a heterologous reporter sequence. See, e.g., the examples and Reginato, et. al., *J. Biol. Chem.* 273:32679 (1998).

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamen-*

*tal Immunology,* Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the AKR1C polypeptides, antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, J. *Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as an AKR1C polypeptide, but have one or more peptide linkages optionally replaced by a linkage selected from the group consisting of, e.g., —CH2NH—, —CH2S—, —CH2—CH2—, —CH=CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of AKR1C or inhibiting or increasing the enzymatic activity of AKR1C.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. (1984) *Nuc. Acids Res.* 12:387-395).

Another example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following:50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a transacting regulatory agent. This phrase specifically encompasses degenerate codons (i.e., different codons which encode a single amino acid) of the native sequence or sequences that may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

"Inhibitors," "activators," and "modulators" of AKR1C expression or of AKR1C activity are used to refer to inhibitory, activating, or modulating molecules, respectively, identified using in vitro and in vivo assays for AKR1C expression or AKR1C activity, e.g., ligands, agonists, antagonists, and their homologs and mimetics. The term "modulator" includes inhibitors and activators. Inhibitors are agents that, e.g., inhibit expression of AKR1C or bind to, partially or totally block stimulation or enzymatic activity, decrease, prevent, delay activation, inactivate, desensitize, or down regulate the activity of AKR1C, e.g., antagonists. Activators are agents that, e.g., induce or activate the expression of a AKR1C or bind to, stimulate, increase, open, activate, facilitate, enhance activation or enzymatic activity, sensitize or up regulate the activity of AKR1C, e.g., agonists. Modulators include naturally occurring and synthetic ligands, antagonists, agonists, small chemical molecules and the like. Such assays for inhibitors and activators include, e.g., applying putative modulator compounds to peripheral cells such as fat or muscle cells, in the presence or absence of AKR1C modulators and then determining the functional effects on AKR1C activity, as described above. Samples or assays comprising AKR1C that are treated with a potential activator, inhibitor, or modulator are compared to control samples without the inhibitor, activator, or modulator to examine the extent of effect. Control samples (untreated with modulators) are assigned a relative AKR1C activity value of 100%. Inhibition of AKR1C is achieved when the AKR1C activity value relative to the control is about 80%, optionally 50% or 25-1%. Activation of AKR1C is achieved when the AKR1C activity value relative to the control is 110%, optionally 150%, optionally 200-500%, or 1000-3000% higher.

BRIEF DESCRIPTION OF THE DRAWINGS

FIG. 6 illustrates an alignment of human and mouse AKR1C sequences. (SEQ ID NOS:37, 39, 41, 43, 45, 1, 7, 17, 23, 47, 49 and 51, respectively). "*" indicates amino acid positions that have a single fully conserved residue. ":" indicates that one of the following groups is fully conserved: STA, NEQK, NHQK, NDEQ, QHRK, MILV, MILF, HY, FYW. "." indicates that one of the following groups is fully conserved: CSA, ATV, SAG, STNK, STPA, SGND, SNDEQK, NDEQHK, NEQHRK, FVLIM, HFY.

DETAILED DESCRIPTION

I. Introduction

Figure 1:
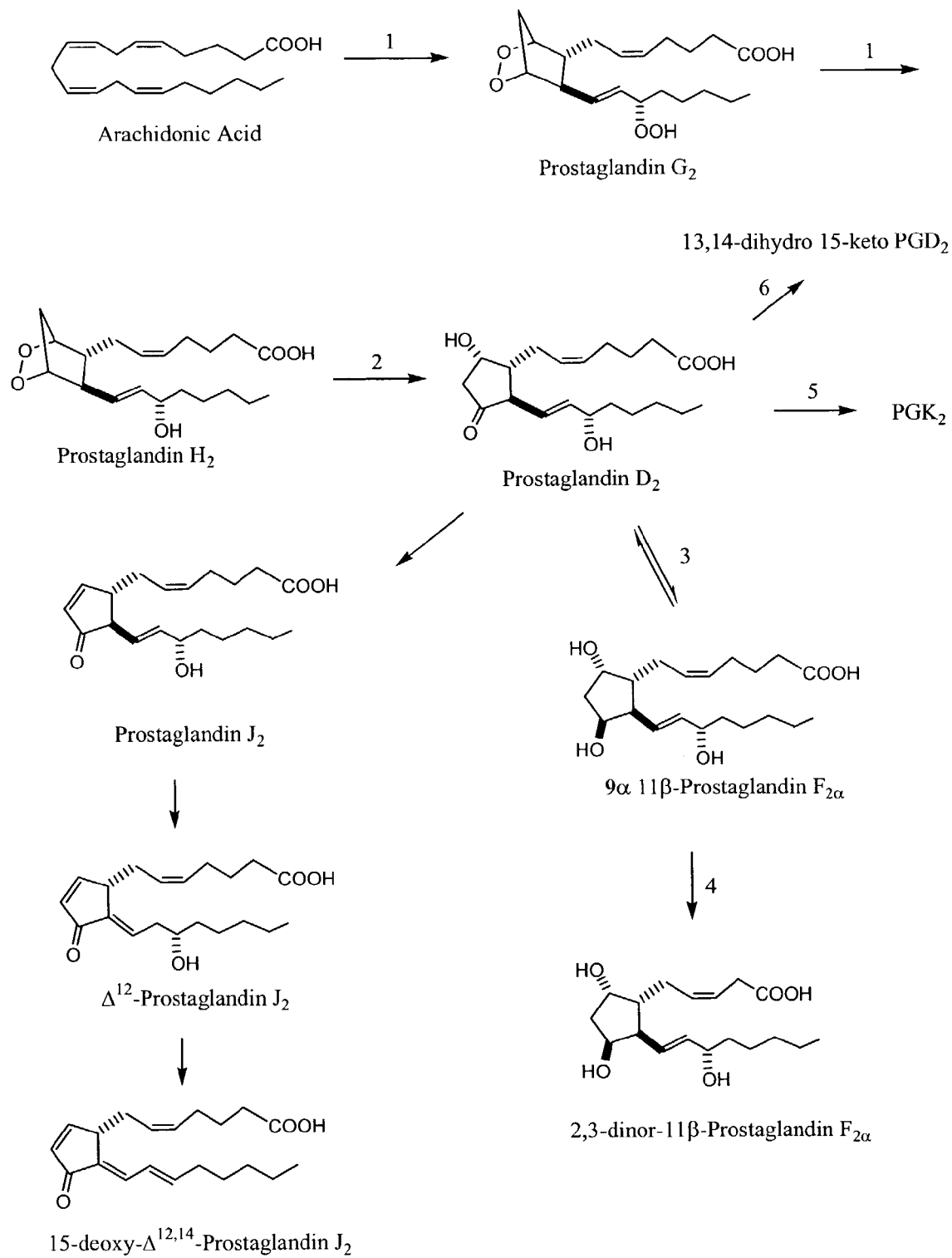
FIG. 1 illustrates the biosynthesis of prostaglandin D2 (PGD2), as well as subsequent reactions that use PGD2 as a substrate. Numbers in the figure indicate the enzyme that catalyzes the displayed reaction (1=Cyclooxygenase 1,2=GSH-dependent prostaglandin H2 D-isomerase and 3=Aldo-keto reductase 1C1, 1C2, 1C3 and 1C4).

This invention is directed to methods of using AKR1C sequences to diagnose and treat diabetes and related diseases. The present method also provides methods of identifying modulators of AKR1C expression and activity. Such modulators are useful for treating Type 2 diabetes as well as syndrome X, polycystic ovarian syndrome, HIV-protease inhibitor-induced insulin resistance, lipodystrophies, hyperglycemia, obesity, hyperlipidemia, hypertriglyceridemia, hypercholesterolemia, impaired glucose tolerance, atherosclerosis, vascular restenosis, irritable bowel syndrome, pancreatitis, adipose cell tumors and carcinomas, acute mountain sickness, Addison's disease, Alzheimer's disease, asthma, autoimmune disorders, burn injury, cold symptoms (e.g., nasal congestion, aches), inflammatory bowel diseases (e.g., Crohn's disease), ischemia-reperfusion injury, liver injury, neuropathies, ophthalmic inflammation, Parkinson's disease, septicemia, and skin disorders (e.g., acne, scleroderma) as well as the pathological aspects of such diseases. Other indications that can be treated with the modulators of the invention include, e.g., diseases involving epidermal or epithelial cell proliferation such as eczema; lupus associated skin lesions; psoriatic arthritis; rheumatoid arthritis, including rheumatoid arthritis involving hyperproliferation and inflammation of epithelial-related cells lining the joint capsule; dermatitides such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The modulators are also useful for treating processes mediated by PPAR-gamma including, e.g., cell differentiation to produce lipid-accumulating cells, the formation of macrophages which lead to the development of atherosclerotic plaques, and the like.

Members of the PPAR (peroxisome proliferation activated receptor) family of ligand-activated transcription factors (PPAR alpha, PPAR beta/delta, and PPAR gamma) have been shown to play important roles in glucose and lipid homeostasis. Synthetic ligands for PPAR-gamma, such as thiazolidinediones, increase peripheral insulin sensitivity and glucose disposal (Day, C. *Diabetic Medicine* 16:179-192 (1999). Furthermore, patients with PPAR gamma mutations have decreased insulin sensitivity (Barroso, I., et al. *Nature* 402: 880-883 (1999)). Therefore, drugs and other ligands that modulate the activity of PPAR gamma result in increased insulin sensitivity and can be used to treat individuals with insulin resistance. In the case of PPAR alpha, lipid-lowering drugs of the fibrate class such as clofibrate have been shown to mediate their effects on lipid metabolism through binding and activation of PPAR alpha; fibrates may also exert insulin sensitizing effects by this mechanism (Guerre-Millo, M. et al. *J. Biol. Chem.* 275:16638-16642 (2000)). Without intending to limit the invention to a particular theory of operation, it is believed that modulation of AKR1C levels or activity also modulates PPAR alpha and/or gamma-mediated effects. Thus, such modulators are also useful for the treatment of dyslipidemias, including hypertriglyceridemias and hyperlipoproteinemias.

The present application demonstrates that, surprisingly, elevated levels of AKR1C1, AKR1C2 and AKR1C3 mRNA occur in people with NIDDM. In some embodiments, increased expression of these enzymes, which have prostaglandin D2 11-keto-reductase activity, increases levels of $9\alpha,11\beta$-$PGF_{2\alpha}$ and decreases levels of a PPAR gamma ligand (15-deoxy-$\Delta^{12,14}$-PGJ2), thereby increasing insulin resistance. Inhibition of the PGD2 11 keto-reductase activity, therefore reduces production of $9\alpha,11\beta$-$PGF_{2\alpha}$ and increases production of 15-deoxy-$\Delta^{12,14}$-PGJ2, thereby decreasing insulin resistance. Alternatively, in embodiments where the net reaction catalyzed by AKR1C results in net synthesis of PGD2, increasing AKR1C activity or expression can decrease insulin resistance.

Figure 2:
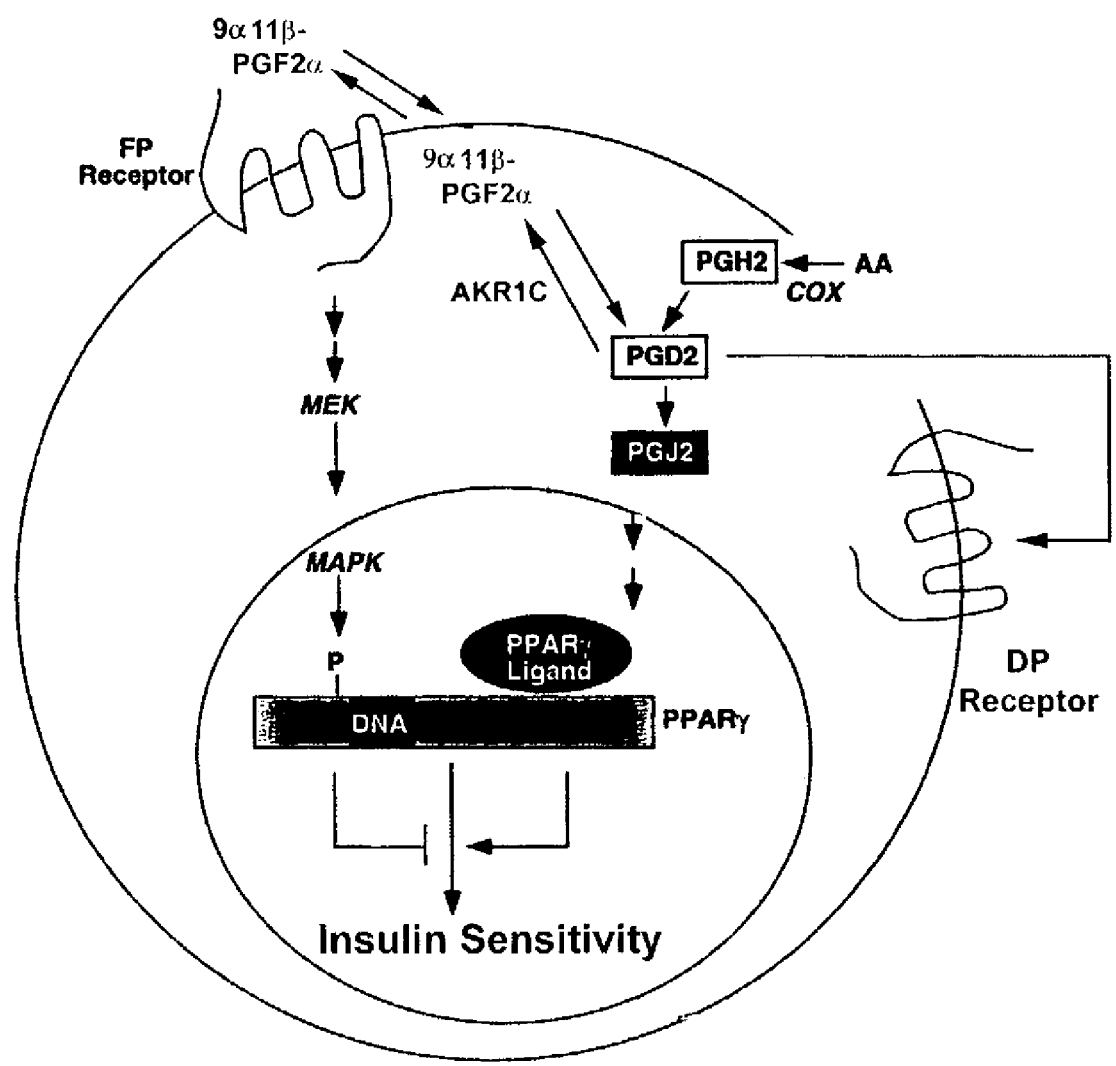
FIG. 2 illustrates signal transduction pathways involving PGD2.

Without intending to limit the invention to a particular theory of action, $9\alpha,11\beta$-$PGF_{2\alpha}$ can be released from muscle cells and act to stimulate the F prostanoid (FP) receptor on the cell surface. See, e.g., FIG. 2. Activation of this GPCR stimulates a MAP kinase-dependent phosphorylation of PPAR gamma on serine 112, causing a conformational change and a reduction in PPAR gamma ligand affinity. See, e.g., Hu et al *Science* 274:2100-2103 (1996). Thus antagonism of the FP receptor also enhances insulin sensitivity and is a useful therapy for NIDDM.

In addition, as shown herein, increased insulin sensitivity occurs in cells treated with PGD2. Without intending to limit the invention to a particular theory or mechanism, it is believed that this result occurs by activation of the DP receptor. Therefore, a DP receptor agonist is an effective therapy for NIDDM. The DP receptor is described in, e.g., Boie, Y., et al. *J. Biol. Chem.* 270:18910-18916 (1995).

Without intending to limit the invention to a particular theory or mechanism, it is believed that modulation of AKR1C activity or levels results in the modulation of PPAR alpha levels. As modulating PPAR alpha levels is an effective treatment of dyslipidemia, the present invention provides methods of treating dyslipidemia by administering modulators of AKR1C to an individual.

II. General Recombinant Nucleic Acid Methods for use with the Invention

In numerous embodiments of the present invention, nucleic acids encoding a AKR1C of interest will be isolated and cloned using recombinant methods. Such embodiments are used, e.g., to isolate AKR1C polynucleotides (e.g., SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID, NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:38, SEQ ID NO:40, SEQ ID NO:42, SEQ ID NO:44, SEQ ID NO:46, SEQ ID NO:48, SEQ ID NO:50, or SEQ ID NO:52) for protein expression or during the generation of variants, derivatives, expression cassettes, or other sequences derived from an AKR1C polypeptide (e.g., SEQ ID NO:1, SEQ ID NO:7, SEQ ID NO:17, SEQ ID NO:23 and SEQ ID NOs: 30, 31, 32, 33, 34, 35, 36, 37, 39, 41, 43, 45, 47, 49, and 51), to monitor AKR1C gene expression, for the isolation or detection of AKR1C sequences in different species, for diagnostic purposes in a patient, e.g., to detect mutations in AKR1C or to detect expression levels of AKR1C nucleic acids or AKR1C polypeptides. In some embodiments, the sequences encoding the AKR1C of the invention are operably linked to a heterologous promoter. In one embodiment, the nucleic acids of the invention are from any mammal, including, in particular, e.g., a human, a mouse, a rat, etc. In some embodiments, the nucleic acids of the invention encode an AKR1C polypeptide with the conserved amino acid residues or groups indicated in FIG. 6 by "*" ":", or ".", or any combination thereof (e.g., "*" and ":" and "." or "*" and ":" or "*" and ".", etc.)

A. General Recombinant Nucleic Acid Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences of AKR1C1, AKR1C2, AKR1C3 or AKR1C4 (e.g., SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:38, SEQ ID NO:40, SEQ ID NO:42, SEQ ID NO:44, SEQ ID NO:46, SEQ ID NO:48, SEQ ID NO:50, or SEQ ID NO:52), which provides a reference for PCR primers and defines suitable regions for isolating AKR1C-specific probes. Alternatively, where the sequence is cloned into an expression library, the expressed recombinant protein can be detected immunologically with antisera or purified antibodies made against the AKR1C of interest.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra). Peripheral cells such as fat or muscle cells are an example of suitable cells to isolate AKR1C RNA and cDNA.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific AKR1C sequences, e.g., the sequences set forth in SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:38, SEQ ID NO:40, SEQ ID NO:42, SEQ ID NO:44, SEQ ID NO:46, SEQ ID NO:48, SEQ ID NO:50, or SEQ ID NO:52. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding an AKR1C polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying the genes encoding an AKR1C polypeptide of the invention from mammalian tissues can be derived from the sequences provided herein, in particular SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, or SEQ ID NO:29. For a general overview of PCR, see, Innis et al. *PCR Protocols: A Guide to Methods and Applications*, Academic Press, San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A gene encoding an AKR1C polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Purification of Proteins of the Invention

Either naturally occurring or recombinant AKR1C can be purified for use in functional assays. Naturally occurring AKR1C can be purified, e.g., from mouse or human tissue such as adipocytes or any other source of an AKR1C ortholog. Recombinant AKR1C can be purified from any suitable expression system.

The AKR1C may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant AKR1C are being purified. For example, proteins having established molecular adhesion properties can be reversibly fused to AKR1C. With the appropriate ligand, AKR1C can be selectively adsorbed to a purification column and then freed from the column in a relatively pure form. The fused protein may be then removed by enzymatic activity. Finally AKR1C could be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Purification of Proteins from Insect Cells

Proteins can also be purified from eukaryotic gene expression systems as described in, e.g., Fernandez and Hoeffler, *Gene Expression Systems* (1999). In some embodiments, baculovirus expression systems are used to isolate AKR1C proteins or other proteins of the invention. Recombinant baculoviruses are generally generated by replacing the polyhedrin coding sequence of a baculovirus with a gene to be expressed (e.g., a AKR1C polynucleotide). Viruses lacking the polyhedrin gene have a unique plaque morphology making them easy to recognize. In some embodiments, a recombinant baculovirus is generated by first cloning a polynucleotide of interest into a transfer vector (e.g., a pUC based vector) such that the polynucleotide is operably linked to a polyhedrin promoter. The transfer vector is transfected with wildtype DNA into an insect cell (e.g., Sf9, Sf21 or BT1-TN-5B1-4 cells), resulting in homologous recombination and replacement of the polyhedrin gene in the wildtype viral DNA with the polynucleotide of interest. Virus can then be generated and plaque purified. Protein expression results upon viral infection of insect cells. Expressed proteins can be harvested from cell supernatant if secreted, or from cell lysates if intracellular. See, e.g., Ausubel et al. and Fernandez and Hoeffler, supra.

C. Standard Protein Separation Techniques For Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine (SEQ ID NO:53) (His), glutathione S transferase (GST) and the like can be used to purify polypeptides. The His tag will also act as a chelating agent for certain metals (e.g., Ni) and thus the metals can also be used to purify His-containing polypeptides. After purification, the tag is optionally removed by specific proteolytic cleavage.

It will be apparent to one of skill that chromatographic techniques can be performed at any scale and using equipment from many different manufacturers (e.g., Pharmacia Biotech).

IV. Detection of Polynucleotides of the Invention

Those of skill in the art will recognize that detection of expression of AKR1C polynucleotides has many uses. For example, as discussed herein, detection of AKR1C levels in a patient is useful for diagnosing diabetes or a predisposition for at least some of the pathological effects of diabetes. Moreover, detection of gene expression is useful to identify modulators of AKR1C expression.

A variety of methods of specific DNA and RNA measurement that use nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting an AKR1C polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of, for example, an AKR1C RNA is measured by quantitating the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), i.e. Gene Chips or microarrays, available from Affymetrix, Inc. in Santa Clara, Calif. can be used to detect changes in expression levels of a plurality of genes involved in the same regulatory pathways simultaneously. See, Tijssen, supra., Fodor et al. (1991) *Science*, 251: 767-777; Sheldon et al (1993) *Clinical Chemistry* 39(4):718-719, and Kozal et al. (1996) *Nature Medicine* 2(7):753-759. Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment. See, e.g., Schena et al., *Science* 270: 467-470 (1995)) and (Lockhart et al., *Nature Biotech.* 14: 1675-1680 (1996)).

Hybridization specificity can be evaluated by comparing the hybridization of specificity-control polynucleotide sequences to specificity-control polynucleotide probes that are added to a sample in a known amount. The specificity-control target polynucleotides may have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples are prepared and labeled with different labeling moieties. A mixture of the two labeled polynucleotide probes is added to a microarray. The microarray is then examined under conditions in which the emissions from the two different labels are individually detectable. Sequences in the microarray that are hybridized to substantially equal numbers of polynucleotide probes derived from both biological samples give a distinct combined fluorescence (Shalon et al. PCT publication WO95/35505). In some embodiments, the labels are fluorescent labels with distinguishable emission spectra, such as Cy3 and Cy5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In some embodiments, the polynucleotide probes are labeled with a fluorescent label and measurement of levels and patterns of fluorescence indicative of complex formation is accomplished by fluorescence microscopy, such as confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples are obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray.

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulavski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *PNAS* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed) *Fundamental Immunology, Third Edition* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1989); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, NY, (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

Single nucleotide polymorphism (SNP) analysis is also useful for detecting differences between alleles of AKR1C genes. AKR1C2, AKR1C3 and AKR1C4 all reside within a region of human chromosome 10 annotated as base pair number 5600000-5900000 (as determined using a BLAT search of the human genome sequence at the University of California Santa Cruz site (also referred to as Golden Path)). Within this region, 159 known SNPs have been reported to date. AKR1C-linked SNPs are useful for diagnosis of AKR1C-linked diseases (e.g., diabetes, dyslipidemia, etc.) in a patient. For example, if an individual carries at least one allele of an AKR1C-linked SNP, the individual is likely predisposed for one or more of those diseases. If the individual is homozygous for a disease-linked AKR1C SNP, the individual is particularly predisposed for AKR1C-linked disease (e.g., diabetes). In some embodiments, the the SNP associated with the AKR1C-linked disease is located within 300,000; 200,000; 100,000; 75,000; 50,000; or 10,000 base pairs of a polynucleotide encoding AKR1C.

Various real-time PCR methods including, e.g., Taqman or molecular beacon-based assays (e.g., U.S. Pat. Nos. 5,210, 015; 5,487,972; Tyagi et al., *Nature Biotechnology* 14:303 (1996); and PCT WO 95/13399 are useful to monitor for the presence of absence of a SNP. Additional SNP detection methods include, e.g., DNA sequencing, sequencing by hybridisation, dot blotting, oligonucleotide array (DNA Chip) hybridization analysis, or are described in, e.g., U.S. Pat. No. 6,177,249; Landegren et al., *Genome Research*, 8:769-776 (1998); Botstein et al., *Am J Human Genetics* 32:314-331 (1980); Meyers et al., *Methods in Enzymology* 155:501-527 (1987); Keen et al., *Trends in Genetics* 7:5 (1991); Myers et al., *Science* 230:1242-1246 (1985); and Kwok et al., *Genomics* 23:138-144 (1994).

V. Immunological Detection of AKR1C, PGD2 OR $9\alpha,11\beta$-Prostaglandin $F_{2\alpha}$ In addition to the detection of AKR1C genes and gene expression using nucleic acid hybridization technology, one can also use immunoassays to detect AKR1C polypeptides, substrates/products of AKR1C activity such as $9\alpha,11\beta$-prostaglandin $F_{2\alpha}$, chemical derivatives thereof and prostaglandin D2 ("PGD2") or chemical derivatives thereof. Immunoassays can be used to qualitatively or quantitatively analyze AKR1C or $9\alpha,11\beta$-$PGF_{2\alpha}$ or PGD2. A general overview of the applicable technology can be found in Harlow & Lane, *Antibodies: A Laboratory Manual* (1988).

A. Antibodies to Target Proteins or other Immunogens

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature*, 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the AKR1C sequences disclosed herein, or a prostaglandin such as $9\alpha,11\beta$-$PGF_{2\alpha}$ or PGD2, is conjugated to a carrier protein and used as an immunogen.

One method for detecting PGD2 is to treat a sample with methoxylamine hydrochloride to produce a stable prostaglandin D2 derivative (11-methoxime-prostaglandin D2). Antibodies and ELISA kits useful for detection of 11-methoxime-prostaglandin D2 are available from Immuno-biological Laboratories (Hamburg, Germany). Similarly, chemical derivatives of $9\alpha,11\beta$-$PGF_{2\alpha}$ can be formed and the derivative quantified. Alternatively, commercial antibodies and ELISA kits useful for detection of $9\alpha,11\beta$-$PGF_{2\alpha}$ are available from, e.g., Cayman Chemical (Ann Arbor, Mich.).

Polyclonal sera are collected and titered against the immunogen in an immunoassay, for example, a solid phase immunoassay with the immunogen immobilized on a solid support. Polyclonal antisera with a titer of $10^4$ or greater are selected and tested for their crossreactivity against non-AKR1C proteins or even other homologous proteins from other organisms, using a competitive binding immunoassay. For antisera raised against $9\alpha,11\beta$ $PGF2\alpha$, cross-reactivity is measured against non-$9\alpha,11\beta$ $PGF2\alpha$ compounds. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the AKR1C of interest or $9\alpha,11\beta$-$PGF_{2\alpha}$ or PGD2. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells according to the general protocol outlined by Huse et al., supra.

Once target immunogen-specific antibodies are available, the immunogen can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to the protein (e.g., AKR1C1, AKR1C2, AKR1C3 or AKR1C4) or a fragment thereof. This antiserum is selected to have low cross-reactivity against non-AKR1C proteins and any such cross-reactivity is removed by immunoabsorption prior to use in the immunoassay. Alternatively, antibodies that recognize more than one or even all AKR1C proteins in a sample can be used, for example to determine the overall level of AKR1C protein in a sample.

B. Immunological Binding Assays

In some embodiments, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume* 37: *Antibodies in Cell Biology*, Academic Press, Inc. NY (1993); Stites, supra. Immunological binding assays (or immunoassays) typically utilize a "capture agent" to specifically bind to and often immobilize the analyte (in this case an AKR1C of the present invention, antigenic subsequences thereof, or other immunogens such as PGD2 or $9\alpha,11\beta$-$PGF_{2\alpha}$). The capture agent is a moiety that specifically binds to the analyte. In a preferred embodiment, the capture agent is an antibody that specifically binds, for example, an AKR1C polypeptide of the invention or other immunogens such as PGD2 or $9\alpha,11\beta$-$PGF_{2\alpha}$. The antibody (e.g., anti-AKR1C antibody) may be produced by any of a number of means well known to those of skill in the art and as described above.

Immunoassays also often utilize a labeling agent to bind specifically to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins or analytes of interest from tissue samples may be either competitive or noncompetitive. Noncompetitive immunoassays are assays in which the amount of captured protein or analyte is directly measured. In one preferred "sandwich" assay, for example, the capture agent (e.g., $9\alpha,11\beta$-$PGF_{2\alpha}$ antibodies or AKR1C antibodies) can be bound directly to a solid substrate where it is immobilized. These immobilized antibodies then capture the $9\alpha,11\beta$-$PGF_{2\alpha}$ or AKR1C present in the test sample. The AKR1C or $9\alpha,11\beta$-$PGF_{2\alpha}$ thus immobilized is then bound by a labeling agent, such as a second anti-AKR1C antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of protein or analyte present in the sample is measured indirectly by measuring the amount of an added (exogenous) protein or analyte (e.g., $9\alpha,11\beta$-$PGF_{2\alpha}$ or the AKR1C of interest) displaced (or competed away) from a specific capture agent, e.g. antibodies raised to $9\alpha,11\beta$ PGF2α or to AKR1C) by the protein or analyte present in the sample. The amount of immunogen bound to the antibody is inversely proportional to the concentration of immunogen present in the sample. In a particularly preferred embodiment, the antibody is immobilized on a solid substrate. The amount of analyte may be detected by providing a labeled analyte molecule. It is understood that labels can include, e.g., radioactive labels as well as peptide or other tags that can be recognized by detection reagents such as antibodies.

Immunoassays in the competitive binding format can be used for cross-reactivity determinations. For example, the protein encoded by the sequences described herein can be immobilized on a solid support. Proteins are added to the assay and compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In a particularly preferred embodiment, western blot (immunoblot) analysis is used to detect and quantify the presence of an AKR1C of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the anti-AKR1C antibodies specifically bind to the AKR1C on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

VI. Identification of Modulators of AKR1C

Modulators of AKR1C, i.e. agonists or antagonists of AKR1C activity or AKR1C polypeptide or polynucleotide expression, are useful for treating a number of human diseases, including diabetes. Administration of AKR1C inhibitors can be used to treat diabetic patients or individuals with insulin resistance. Alternatively, activators of AKR1C can be used to treat diabetic patients or individuals with insulin resistance by stimulating synthesis of PG D2.

A. Agents that Modulate AKR1C

The agents tested as modulators of AKR1C can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). Modulators also include agents designed to reduce the level of AKR1C mRNA (e.g. antisense molecules, ribozymes, DNAzymes, small inhibitory RNAs and the like) or the level of translation from an mRNA (e.g., translation blockers such as an antisense molecules that are complementary to translation start or other sequences on an mRNA molecule). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al, *J. Amer. Chem. Soc.* 114:9217-9218 (1992)), analogous organic syntheses of small compound libraries (Chen et al., *J.*

*Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Methods of Screening for Modulators of AKR1C

A number of different screening protocols can be utilized to identify agents that modulate the level of expression or activity of AKR1C in cells, particularly mammalian cells, and especially human cells. In general terms, the screening methods involve screening a plurality of agents to identify an agent that modulates the activity of AKR1C by, e.g., binding to an AKR1C polypeptide, preventing an inhibitor or activator from binding to AKR1C, increasing association of an inhibitor or activator with AKR1C, or activating or inhibiting expression of AKR1C. In some embodiments, an agent only modulates the activity or expression of one, two or three of AKR1C1, AKR1C2, AKR1C3, or AKR1C4. In some embodiments, all AKR1C polypeptides are modulated by the agent.

1. AKR1C Binding Assays

Preliminary screens can be conducted by screening for agents capable of binding to AKR1C, as at least some of the agents so identified are likely AKR1C modulators. Binding assays are also useful, e.g., for identifying endogenous proteins that interact with AKR1C. For example, antibodies, receptors or other molecules that bind AKR1C can be identified in binding assays.

Binding assays usually involve contacting an AKR1C protein with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to AKR1C or displacement of labeled substrates. The AKR1C protein utilized in such assays can be naturally expressed, cloned or synthesized AKR1C.

In addition, mammalian or yeast two-hybrid approaches (see, e.g., Bartel, P. L. et. al. Methods Enzymol, 254:241 (1995)) can be used to identify polypeptides or other molecules that interact or bind when expressed together in a cell.

2. Expression Assays

Screening for a compound that modulates the expression of AKR1C are also provided. Screening methods generally involve conducting cell-based assays in which test compounds are contacted with one or more cells expressing AKR1C, and then detecting an increase or decrease in AKR1C expression (either transcript, translation product, or catalytic product, (e.g., $9\alpha,11\beta$-$PGF_{2\alpha}$) or substrate (e.g., prostaglandin D2 or NADPH). Assays can be performed with peripheral cells, or other cells, that express endogenous AKR1C.

AKR1C expression can be detected in a number of different ways. As described infra, the expression level of AKR1C in a cell can be determined by probing the mRNA expressed in a cell with a probe that specifically hybridizes with a transcript (or complementary nucleic acid derived therefrom) of AKR1C. Probing can be conducted by lysing the cells and conducting Northern blots or without lysing the cells using in situ-hybridization techniques. Alternatively, AKR1C protein can be detected using immunological methods in which a cell lysate is probed with antibodies that specifically bind to AKR1C.

Alternatively, the level of AKR1C enzymatic activity in a cell or other sample is determined and compared to a baseline value (e.g., a control value). Activity can be measured based on a crude extract or partially or essentially purified AKR1C from a sample. Measurement of AKR1C activity is described, for example, in Ohara et al. *Biochimicia et Biophysica Acta* 1215:59-65 (1994). In other embodiments, the quantity or level of AKR1C substrate (e.g., prostaglandin D2 or NADPH) or product (e.g., $9\alpha,11\beta$-$PGF_{2\alpha}$) is determined and compared to a baseline (control) value.

Other cell-based assays involve reporter assays conducted with cells using standard reporter gene assays. These assays can be performed in either cells that do, or do not, express AKR1C. Some of these assays are conducted with a heterologous nucleic acid construct that includes an AKR1C promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) *Nature* 282:864-869), luciferase, β-galactosidase and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. Modulated promoter expression is monitored by detecting the level of a detectable reporter. A number of different kinds of AKR1C modulators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of AKR1C expression levels for a control population (e.g., healthy individuals not having or at risk for Type 2 diabetes) or cells (e.g., tissue culture cells not exposed to an AKR1C modulator). Expression levels can also be determined for cells that do not express AKR1C as a negative control. Such cells generally are otherwise substantially genetically the same as the test cells.

A variety of different types of cells can be utilized in the reporter assays. Cells that express an endogenous AKR1C include, e.g., cells from peripheral tissues such as fat and muscle cells. Cells that do not endogenously express AKR1C can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HepG2, COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

3. Catalytic Activity

Catalytic activity of AKR1C polypeptides can be determined by measuring the production of products (e.g., $9\alpha,11\beta$-$PGF_{2\alpha}$) or by measuring the consumption of substrates (e.g., prostaglandin D2 or NADPH). Activity refers to either the rate of catalysis or the ability to the polypeptide to bind ($K_m$) the substrate or release the catalytic product ($K_d$).

Analysis of AKR1C polypeptide enzymatic activity is performed according to general biochemical procedures. Such assays include cell-based assays as well as in vitro assays involving purified or partially purified AKR1C polypeptides or crude cell lysates. The assays generally involve providing a known quantity of substrate (e.g., prostaglandin D2 and NADPH) and quantifying product (e.g., $9\alpha,11\beta$-$PGF_{2\alpha}$) as a function of time. An ELISA kit for detecting $9\alpha,11\beta$-$PGF2\alpha$ levels in samples is available from Cayman Chemical (Ann Arbor, Mich.). The catalytic activity of purified AKR1C can also be measured by monitoring the decrease in NADPH absorbance at 340 nm. See, H. Ohara et al., *Biochimica et Biophysica Acta* 1215:59-65 (1994). The activity of AKR1C can also be monitored by measuring the decrease in PGD2 levels. Biochemical analyses of AKR1C polypeptides and their activity have been described previously. See, e.g., Penning et al., *Biochem. J.* 351:67-77 (2000).

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if AKR1C is in fact modulated. The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty rats etc) or polygenic models of diabetes (e.g., a high fat fed mouse model) can be useful for validating AKR1C modulation in a diabetic animal.

C. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

The molecule of interest (e.g., AKR1C) can be bound to the solid state component, directly or indirectly, via covalent or non covalent linkage, e.g., via a tag. The tag can be any of a variety of components. In general, a molecule that binds the tag (a tag binder) is fixed to a solid support, and the tagged molecule of interest (e.g., AKR1C) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, poly-His, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag, binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:54). Such flexible linkers are known to those of skill in the art. For example, poly(ethelyne glycol) linkers are available from Shearwater Polymers, Inc., Huntsville, Ala. These linkers optionally have amide linkages, sulfhdryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of AKR1C. Control reactions that measure AKR1C activity of the cell in a reaction that does not include a potential modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions that do not include a modulator provide a background level of binding activity.

In some assays it will be desirable to have positive controls. At least two types of positive controls are appropriate. First, a known activator of AKR1C of the invention can be incubated with one sample of the assay, and the resulting increase in signal resulting from an increased expression level or activity of AKR1C are determined according to the methods herein. Second, a known inhibitor of AKR1C can be added, and the resulting decrease in signal for the expression or activity of AKR1C can be similarly detected. It will be appreciated that modulators can also be combined with activators or inhibitors to find modulators that inhibit the increase or decrease that is otherwise caused by the presence of the known modulator of AKR1C.

D. Computer-Based Assays

Yet another assay for compounds that modulate the activity of AKR1C involves computer-assisted drug design, in which a computer system is used to generate a three-dimensional structure of AKR1C based on the structural information encoded by its amino acid sequence. The input amino acid sequence interacts directly and actively with a pre-established algorithm in a computer program to yield secondary, tertiary, and quaternary structural models of the protein. The crystal structure of the rat AKR1C9 and human AKR1C2 polypeptide, as well as the rat polypeptide interacting with NADPH or NADPH and testerone has been described. See, e.g., Hoog et al *Proc. Natl. Acad. Sci. USA* 91:2517 (1994); Bennett et al *Biochemistry* 35:10702 (1996); Bennett et al *Structure* 5:799 (1997); Jin et al. *Biochemistry* 40:10161 (2001). The models of the protein structure are then examined to identify regions (e.g., the active site) of the structure that have the ability to bind substrates, for example, prostaglandin D2. Similar analyses can be performed on potential receptors or binding partners of AKR1C and can be used to identify regions of interaction with AKR1C. These regions are then used to identify polypeptides that bind to AKR1C.

Once the tertiary structure of a protein of interest has been generated, potential modulators can be identified by the computer system. Three-dimensional structures for potential modulators are generated by entering chemical formulas of compounds. The three-dimensional structure of the potential modulator is then compared to that of AKR1C to identify binding sites of AKR1C. Binding affinity between the protein and modulators is determined using energy terms to determine which ligands have an enhanced probability of binding to the protein.

VII. Compositions, Kits and Integrated Systems

The invention provides compositions, kits and integrated systems for practicing the assays described herein using nucleic acids encoding the AKR1C polypeptides of the invention, or AKR1C proteins, anti-AKR1C antibodies, etc.

The invention provides assay compositions for use in solid phase assays; such compositions can include, for example, one or more nucleic acids encoding an AKR1C immobilized on a solid support, and a labeling reagent. In each case, the assay compositions can also include additional reagents that are desirable for hybridization. Modulators of expression or activity of an AKR1C of the invention can also be included in the assay compositions.

The invention also provides kits for carrying out the assays of the invention. The kits typically include a probe that comprises an antibody that specifically binds to AKR1C or a polynucleotide sequence encoding an AKR1C polypeptide, and a label for detecting the presence of the probe. The kits may include several polynucleotide sequences encoding AKR1C polypeptides of the invention. Kits can include any of the compositions noted above, and optionally further include additional components such as instructions to practice a high-throughput method of assaying for an effect on expression of the genes encoding the AKR1C polypeptides of the invention, or on activity of the AKR1C polypeptides of the invention, one or more containers or compartments (e.g., to hold the probe, labels, or the like), a control modulator of the expression or activity of AKR1C polypeptides, a robotic armature for mixing kit components or the like.

The invention also provides integrated systems for high-throughput screening of potential modulators for an effect on the expression or activity of the AKR1C polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT®, WINDOWS95®, WINDOWS98®, or WINDOWS2000® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VIII. Administration and Pharmaceutical Compositions

Modulators of AKR1C (e.g., antagonists or agonists) can be administered directly to the mammalian subject for modulation of AKR1C activity in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17$^{th}$ ed. 1985)).

The modulators (e.g., agonists or antagonists) of the expression or activity of the AKR1C, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

The modulators (e.g., agonists or antagonists) of the expression or activity of the AKR1C, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, AKR1C modulators of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. Prog. Drug Res. (1998) 51: 33-94; Haffner, S. Diabetes Care (1998) 21: 160-178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999) 84: 1165-71; United Kingdom Prospective Diabetes Study Group: UKPDS 28, Diabetes Care (1998) 21: 87-92; Bardin, C. W., (ed.), Current Therapy In Endocrinology And Metabolism, 6th Edition (Mosby—Year Book, Inc., St. Louis, Mo. 1997); Chiasson, J. et al., Ann. Intern. Med. (1994) 121: 928-935; Coniff, R. et al., Clin. Ther. (1997) 19: 16-26; Coniff, R. et al., Am. J Med. (1995) 98: 443-451; and Iwamoto, Y. et al., Diabet. Med. (1996) 13 365-370; Kwiterovich, P. Am. J. Cardiol (1998) 82(12A):3U-17U). These studies indicate that modulation of diabetes and hyperlipidemia, among other diseases, can be further improved by the addition of a second agent to the therapeutic regimen. Combination therapy includes administration of a single pharmaceutical dosage formulation that contains an AKR1C modulator of the invention and one or more additional active agents, as well as administration of an AKR1C modulator and each active agent in its own separate pharmaceutical dosage formulation. For example, an AKR1C modulator and a thiazolidinedione can be administered to the human subject together in a single oral dosage composition, such as a tablet or capsule, or each agent can be administered in separate oral dosage formulations. Where separate dosage formulations are used, an AKR1C modulator and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated) atherosclerosis, includes combination of a modulator of AKR1C with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; vitamin B6 (also known as pyridoxine) and the pharmaceutically acceptable salts thereof, such as the HCl salt; vitamin B12 (also known as cyanocobalamin); vitamin B3 (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the modulators of the invention can be administered in combination with more than one additional active agent, for example, a combination of an AKR1C modulator with an HMG-CoA reductase inhibitor (e.g., lovastatin, simvastatin and pravastatin) and aspirin.

Another example of combination therapy can be seen in treating obesity or obesity-related disorders, wherein the AKR1C modulators can be effectively used in combination with, for example, phenylpropanolamine, phentermine, diethylpropion, mazindol; fenfluramine, dexfenfluramine, phentiramine, β3 adrenoceptor agonist agents; sibutramine, gastrointestinal lipase inhibitors (such as orlistat), and leptins. Other agents used in treating obesity or obesity-related disorders wherein the AKR1C modulators can be effectively used in combination with, for example, neuropeptide Y, enterostatin, cholecytokinin, bombesin, amylin, histamine H3 receptors, dopamine D2 receptors, melanocyte stimulating hormone, corticotrophin releasing factor, galanin and gamma amino butyric acid (GABA).

Still another example of combination therapy can be seen in modulating diabetes (or treating diabetes and its related symptoms, complications, and disorders), wherein the AKR1C modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No. 5,859, 037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose); amylin and amylin derivatives (such as pramlintide, (see, also, U.S. Pat. Nos. 5,902,726; 5,124,314; 5,175, 145 and 6,143,718.)); insulin secretogues (such as repaglinide, gliquidone, and nateglinide (see, also, U.S. Pat. Nos. 6,251,856; 6,251,865; 6,221,633; 6,174,856)), insulin; as well as the active agents discussed above for treating atherosclerosis.

A further example of combination therapy can be seen in modulating hyperlipidemia (treating hyperlipidemia and its related complications), wherein the AKR1C modulators of the invention can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

IX. Diagnosis of Diabetes

The present invention also provides methods of diagnosing diabetes or a predisposition of at least some of the pathologies of diabetes or another AKR1C-related disease. Diagnosis can involve determination of a genotype of an individual (e.g., with SNPs) and comparison of the genotype with alleles known to have an association with the occurrence of diabetes or other AKR1C-related disease. Alternatively, diagnosis also involves determining the level of AKR1C in a patient and then comparing the level to a baseline or range. Typically, the baseline value is representative of AKR1C in a healthy (i.e., non-diabetic and typically non-obese) person. As discussed above, variation of levels (e.g., high levels) of AKR1C from the baseline range indicates that the patient is either diabetic or at risk of developing at least some of the pathologies of diabetes. In some embodiments, the level of AKR1C are measured by taking a blood, urine or tissue sample from a patient and measuring the amount of AKR1C in the sample using any number of detection methods, such as those discussed herein. For instance, fasting and fed blood or urine levels can be tested.

In some embodiments, the level of the enzymatic product of AKR1C (e.g., 9α,11β-PGF$_{2α}$, PGD2, or derivatives of a product) is measured and compared to a baseline value of a healthy (i.e., non-diabetic and typically non-obese) person or persons. Modulated (e.g., high) levels of 9α,11β-PGF$_{2α}$ compared to the baseline indicates that the patient is either diabetic or at risk of developing at least some of the pathologies of diabetes. Patient samples can be blood, urine or tissue samples.

In some embodiments, the level of AKR1C activity or expression in a sample is determined and compared to a baseline value of a healthy person or persons. Alternatively, the level of AKR1C activity or expression is determined for the same individual at more than one time points, e.g., a day, a week and month, a year or longer apart. Modulation of AKR1C activity or expression between samples indicates the development of diabetes or a predisposition to develop diabetes. In some embodiments, the baseline level and the level in a sample from an individual, or at least two samples from an individual differ by at least about 5%, 10%, 20%, 50%, 75%, 100%, 200%, 500%, 1000% or more. In some embodiments, the sample from the individual is greater by at least one of the above-listed percentages relative to the baseline level. In some embodiments, the sample from the individual is lower by at least one of the above-listed percentages relative to the baseline level. Similarly, the level in a sample taken from an individual some time period after a first sample was taken can be higher or lower than the level in the first sample.

In some embodiments, the level of AKR1C activity or expression is used to monitor the effectiveness of antidiabetic therapies such as thiazolidinediones, metformin, sulfonylureas and other standard therapies. In some embodiments the activity or expression of AKR1C will be measured prior to and after treatment of diabetic or insulin resistant patients with antidiabetic therapies as a surrogate marker of clinical effectiveness. For example, the greater the reduction in AKR1C expression or activity indicates greater effectiveness.

Activity can be measured based on a crude extract or partially or essentially purified AKR1C from a sample. Measurement of AKR1C activity is described, for example, in Ohara et al. *Biochimica et Biophysica Acta* 1215:59-65 (1994).

Glucose/insulin tolerance tests can also be used to detect the effect of glucose levels on AKR1C, 9α,11β-PGF$_{2α}$, or PGD2 levels. In glucose tolerance tests, the patient's ability to tolerate a standard oral glucose load is evaluated by assessing serum and urine specimens for glucose levels. Blood samples are taken before the glucose is ingested, glucose is given by mouth, and blood or urine glucose levels are tested at set intervals after glucose ingestion. Similarly, meal tolerance tests can also be used to detect the effect of insulin or food, respectively, on AKR1C, 9α,11β-PGF$_{2α}$, or PGD2 level.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Background

Gene expression profiling was conducted using both standard and muscle-specific micro-arrays (gene chips); the latter were designed using human muscle expressed sequence tags. Gene expression profiles in muscle samples isolated from lean, obese and diabetic individuals under basal (pre-clamp) conditions and clamp conditions were compared. Clamp refers to an infusion of insulin at high concentrations into the patient (hyperinsulinemia) co-incident with an infusion of glucose to maintain normal glucose levels (euglycemia). This procedure was performed for 5 hours following the removal of the pre-clamp sample. Two studies were done which are referred to as the Study A and the Study B. For the purposes of this disclosure these studies are essentially identical in nature except that they contain largely non-overlapping sets of patients.

Example 1

This example shows that AKR1C gene expression is increased in diabetic tissue compared to healthy tissue Muscle samples from four lean individuals and three diabetics were analyzed using the micro-arrays. The level of AKR1C mRNA was 2.4-fold higher in diabetics versus lean individuals.

Muscle samples from eight lean non-diabetic, eight obese non-diabetic and ten diabetic patient enrolled in Study A were analyzed using a human muscle-specific chip set. With this group of patients, AKR1C mRNA levels were 2.5-fold higher in diabetics as compared to lean individuals when one AKR1C probe set was used to assess mRNA levels. The corresponding values for three different AKR1C probe sets were 2.6, 3.7 and 2.8-fold, respectively. During the hyperinsulinemic clamp, up-regulation of AKR1C mRNA was not observed in any patient group. Therefore, up-regulation of AKR1C mRNA is not due to the hyperinsulinemia commonly found in diabetics Analysis of data generated by combining patient data from the Study A and Study B provided further evidence of up regulation of AKR1C in diabetic muscle compared to lean muscle. The fold changes were: probe 1, 2.26 fold, p=0.00006; probe 2, 2.43 fold, p=0.001; probe 3, 2.57 fold, p=0.0018; probe 4, 2.49 fold, p=0.0012. There was some indication of up-regulation of AKR1C in obese individuals (probe 1, 1.33 fold, p=0.042; probe 2, 1.22 fold, p=0.258; probe 3, 1.32 fold, p=0.0018 and probe 4, 1.44 fold, p=0.0012). These data confirmed the up-regulation of AKR1C mRNA in human diabetic muscle compared to lean muscle.

Example 2

This example shows that AKR1C mRNA is upregulated in diabetic tissue using a technology different than gene chips.

PCR primers and Taqman MGB (minor groove binding) Probes were designed using Perkin Elmer's Primer Express software (Version 1.5). Briefly, primers are chosen to produce an amplicon of 80-120 nucleotides in length. Specificity is obtained by using primers and probes that hybridize efficiently with only one of several highly homologous cDNAs. With the correct PCR conditions, one nucleotide difference is sufficient to disrupt MGB probe hybridization. We used the following primer/probe combinations to specifically measure human AKR1C1, AKR1C2 AKR1C3 and AKR1C4 mRNA levels in a complex mixture.

```
AKR1C1 MGB probe:
6-fam-CTGGCTTCCGCCATAT             (SEQ ID NO:55)

AKR1C1 forward PCR primer:
AGCTTTAGAGGCCACCAAATTG             (SEQ ID NO:56)

AKR1C1 reverse PCR primer:
AACCTGCTCCTCATTATTGTATAAATGA       (SEQ ID NO:57)

AKR1C2 MGB probe:
6fam-AGAAGCCGGGTTCCA               (SEQ ID NO:58)

AKR1C2 forward PCR primer:
CTAGAGGCCGTCAAATTGGC               (SEQ ID NO:59)

AKR1C2 reverse PCR primer:
ACCTGCTCCTCATTATTGTAAACATGT        (SEQ ID NO:60)

AKR1C3 MGB probe:
6fam-CTTTCACCAACAGATGAA            (SEQ ID NO:61)

AKR1C3 forward PCR primer
CTTATTCATTCTCCAATGTCTCTAAAGC       (SEQ ID NO:62)

AKR1C3 reverse PCR primer
TCCACTATGTCAAATATTACTTTTCCATTT     (SEQ ID NO:63)

AKR1C4 MGB probe:
ATGAAAATGGAAAAGTAATATTCGACA        (SEQ ID NO:64)

AKR1C4 forward PCR primer:
CAGGTGAGACGCCACTACCA               (SEQ ID NO:65)

AKR1C4 reverse PCR primer:
ACCTCCCATGTGGCACAGA.               (SEQ ID NO:66)
```

Using these primer/probe sets, the levels of AKR1C1 mRNA, AKR1C2 mRNA and AKR1C3 mRNA were analyzed in samples from Study A. We found AKR1C1, AKR1C2 and AKR1C3 to be up-regulated 3.7 fold, 4.26 fold and 4.42 fold respectively in muscles from diabetic individuals when compared to muscles from lean individuals. As in the previously discussed chip data, there was no up-regulation of AKR1C1, AKR1C2 or AKR1C3 by insulin. This finding (i) indicated that AKR1C, AKR1C2 and AKR1C3 were all expressed in human muscle and (ii) that AKR1C1 mRNA, AKR1C2 mRNA and AKR1C3 mRNA were all elevated in diabetic muscle compared to lean muscle.

Example 3

This example shows that $9\alpha,11\beta\text{-PGF}_{2\alpha}$ is inactive as a PPAR activator.

Prostaglandin D2 and $9\alpha,11\beta\text{-PGF}_{2\alpha}$ were assayed in cell-based assays (ex vivo) designed to detect PPAR ligand activity. The assay uses a recombinant protein consisting of a PPAR ligand-binding domain coupled to a heterologous DNA binding domain. See, e.g., Reginato, et. al., *J. Biol. Chem.* 273:32679 (1998). Binding of a ligand to the PPAR binding domain drives expression of a reporter gene. Significant activation of PPAR alpha and PPAR gamma by PGD2, but not by $9\alpha,11\beta\text{-PGF}_{2\alpha}$, was observed. This observation shows that increasing PGD2 levels in cells will activate PPAR alpha and PPAR gamma, while increasing the levels of $9\alpha,11\beta\text{-PGF}_{2\alpha}$ is without effect. These observations demonstrate that increased levels of AKR1C reduce cellular levels of a PPAR activator (PGD2) and increase levels of a molecule that is not a PPAR activator ($9\alpha,11\beta\text{-PGF}_{2\alpha}$).

Example 4

This example shows that prostaglandin D2, but not $9\alpha,11\beta\text{-PGF}_{2\alpha}$, activates a natural PPAR-responsive promoter Prostaglandin D2 and $9\alpha,11\beta\text{-PGF}_{2\alpha}$ were assayed in cell-based assays (ex vivo) designed to detect activation of a natural PPAR responsive promoter. The assay uses the promoter region of the mouse aP2 gene, which contains binding sites for PPARs (both PPAR alpha and gamma) coupled to a reporter gene. Binding of a ligand to endogenous PPAR results in activation of the aP2 reporter gene. Significant activation of the aP2 reporter gene by PGD2, but not by $9\alpha,11\beta\text{ PGF}_{2\alpha}$, was observed. This observation shows that increasing PGD2 levels in cells will activate endogenous PPARs, while increasing the levels of $9\alpha,11\beta\text{-PGF}_{2\alpha}$ is without effect. These observations support the hypothesis that increased levels of AKR1C would reduce cellular levels of a PPAR activator (PGD2) and increase levels of an inactive molecule ($9\alpha,11\beta\text{-PGF}_{2\alpha}$).

Example 5

This example shows that $9\alpha,11\beta\text{-PGF}_{2\alpha}$ is inactive with respect to regulating endogenous genes regulated by PPAR ligands.

Using a standard mouse micro-array, we found that mouse 3T3-L1 adipocytes treated with three different thiazolidinedione-based PPAR gamma ligands (pioglitazone, rosiglitazone and troglitazone) show changes in expression of RGS2 mRNA (regulator of G protein signaling 2, U67187) and pyruvate dehydrogenase kinase 4 mRNA (J001418). For RGS2 we observed down-regulation as follows; pioglitazone 0.29 fold p<0.00009, rosiglitazone 0.25 fold p<0.00003, troglitazone, 0.27 fold p<0.00085. For PDHK4 we observed up regulation as follows; pioglitazone 3.13 fold p<2×10-6, rosiglitazone 3.16 fold p<0.00005, troglitazone 3.2 fold p<0.0006). Therefore we have found that RGS2 and PDHK4 are down-regulated and up-regulated by PPAR gamma ligands respectively. As such these regulations are reflective of endogenous PPAR activation of endogenous genes.

Primers were designed against murine RGS2 and murine PDHK4 and the gene expression changes observed with the standard mouse chips were verified using Taqman PCR with SYBR green detection. Treatment of cells with pioglitazone, rosiglitazone or troglitazone caused a down regulation of RGS2 by 0.47 fold, 0.41 fold and 0.55 fold, respectively. We observed up regulation of PDHK4 by 4.9 fold, 5.45 fold and 5.5 fold for pioglitazone, rosiglitazone and troglitazone respectively. These observations demonstrate the activity of PPAR gamma ligands can be measured in intact cells using Taqman PCR to quantify levels of endogenous genes.

Taqman primers were used to analyze the expression of RGS2 and PDHK4 in mouse 3T3-L1 adipocytes treated with rosiglitazone, PGD2 and $9\alpha,11\beta\text{-PGF}_{2\alpha}$. Down regulation of RGS2 was observed with both rosiglitazone and PGD2 treatment (0.20 fold change and 0.29 fold change respectively). In contrast, the fold change with $9\alpha,11\beta\text{-PGF}_{2\alpha}$ was 0.75. Up regulation of PDHK4 was also observed-with both rosiglitazone and PGD2 (3.73 fold change and 2.39 fold change respectively). In contrast, the fold change with $9\alpha,11\beta\text{-PGF}_{2\alpha}$ was 0.77. This data suggests that increasing cellular levels of PGD2 affects endogenous gene expression patterns in the same way as a known PPAR ligand. In contrast $9\alpha,11\beta\text{-PGF}_{2\alpha}$ is inactive with respect to regulating endogenous genes regulated by PPAR ligands.

Example 6

This example shows that PGD2, but not $9\alpha,11\beta\text{-PGF}_{2\alpha}$, enhances glucose transport.

Treatment of mouse 3T3-L1 adipocytes for 40 hours with PGD2 enhances glucose transport to similar levels as those observed with the PPAR ligand rosiglitazone. Treatment with $9\alpha,11\beta\text{-PGF}_{2\alpha}$ had no effect on glucose transport. This shows that increasing cellular levels of PGD2 results in increased PPAR activity and hence increased insulin sensitivity and that $9\alpha,11\beta\text{-PGF}_{2\alpha}$ is inactive.

Example 7

This example shows that overexpression of AKR1C1, AKR1C2, AKR1C3 or AKR1C4 in 3T3-L1 adipocytes substantially inhibits the effect of PGD2 to enhance insulin-stimulated glucose transport.

Figure 3:
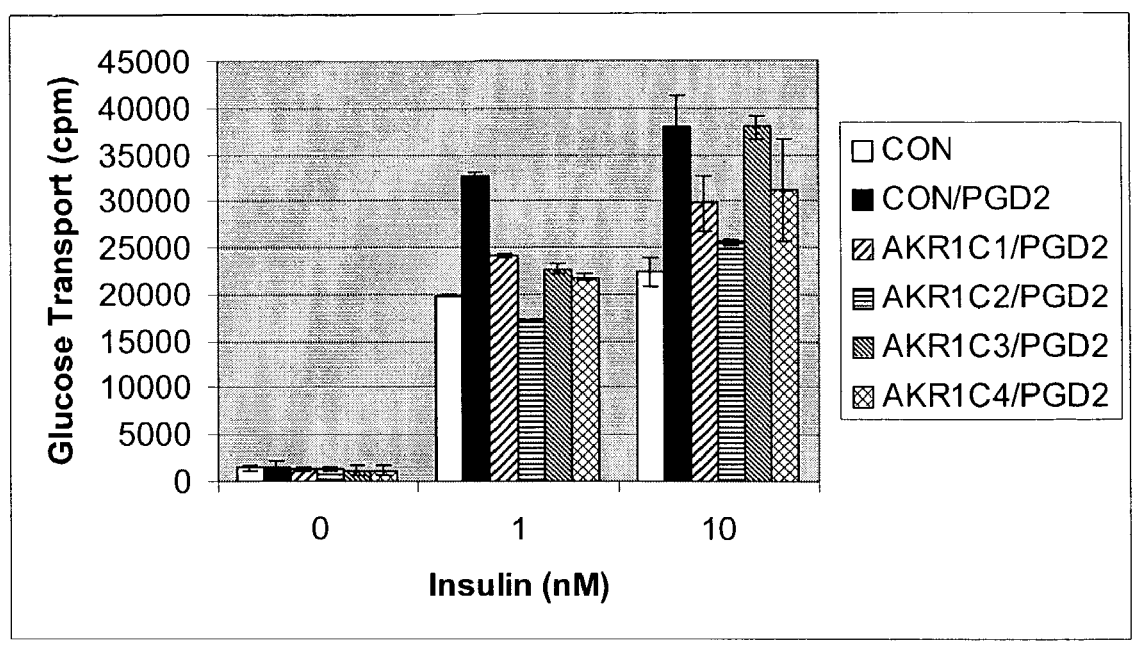
FIG. 3 illustrates glucose transport in cells infected with a control adenovirus or an adenovirus encoding AKR1C and then treated with PGD2.

3T3-L1 adipocytes were infected with either control adenovirus or recombinant adenovirus encoding the four human AKR1C isoforms and incubated 20 hours to allow for protein expression. Cells were then treated 20 hours with 4 µM PGD2 and glucose transport in the absence and presence of insulin was measured. The amount of 3H-2-deoxyglucose (cpm) incorporated into the cells is shown in FIG. 3.

In cells infected with the control virus, PGD2 enhances insulin-stimulated glucose transport. Overexpression of AKR1C1, AKR1C2, AKR1C3 or AKR1C4 substantially reduces the effectiveness of PGD2.

Overall these data demonstrate that PGD2 acts as a positive regulator of PPAR activity and that the product of AKR1C action on PGD2, namely $9\alpha,11\beta\text{-PGF}_{2\alpha}$ is inactive with regard to PPAR activity. Thus, overexpression of AKR1C induces a state of insulin resistance.

Example 8

This example demonstrates that all AKR1C isoforms have PGD2 11 keto-reductase activity.

3T3-L1 adipocytes were infected with the indicated recombinant adenovirus and incubated twenty hours to allow the cells to express the AKR1C isoform indicated. Cells were then incubated in the presence of 4 µM PGD2 for an additional 20 hours. A media sample was obtained and the amount of 9α,11β PGF2α was determined by an enzyme-linked immunoabsorbant assay. The concentration of 9α,11β-PGF2α present in the media is shown in the following table.

| Adenovirus | 9α, 11β-PGF2α Concentration |
|---|---|
| Control | 2 nM |
| AKR1C1 | 55 nM |
| AKR1C2 | 56 nM |
| AKR1C3 | 49 nM |
| AKR1C4 | 128 nM |

Example 9

This example demonstrates purification of each of the AKR1C isoforms from bacteria.

Figure 4:
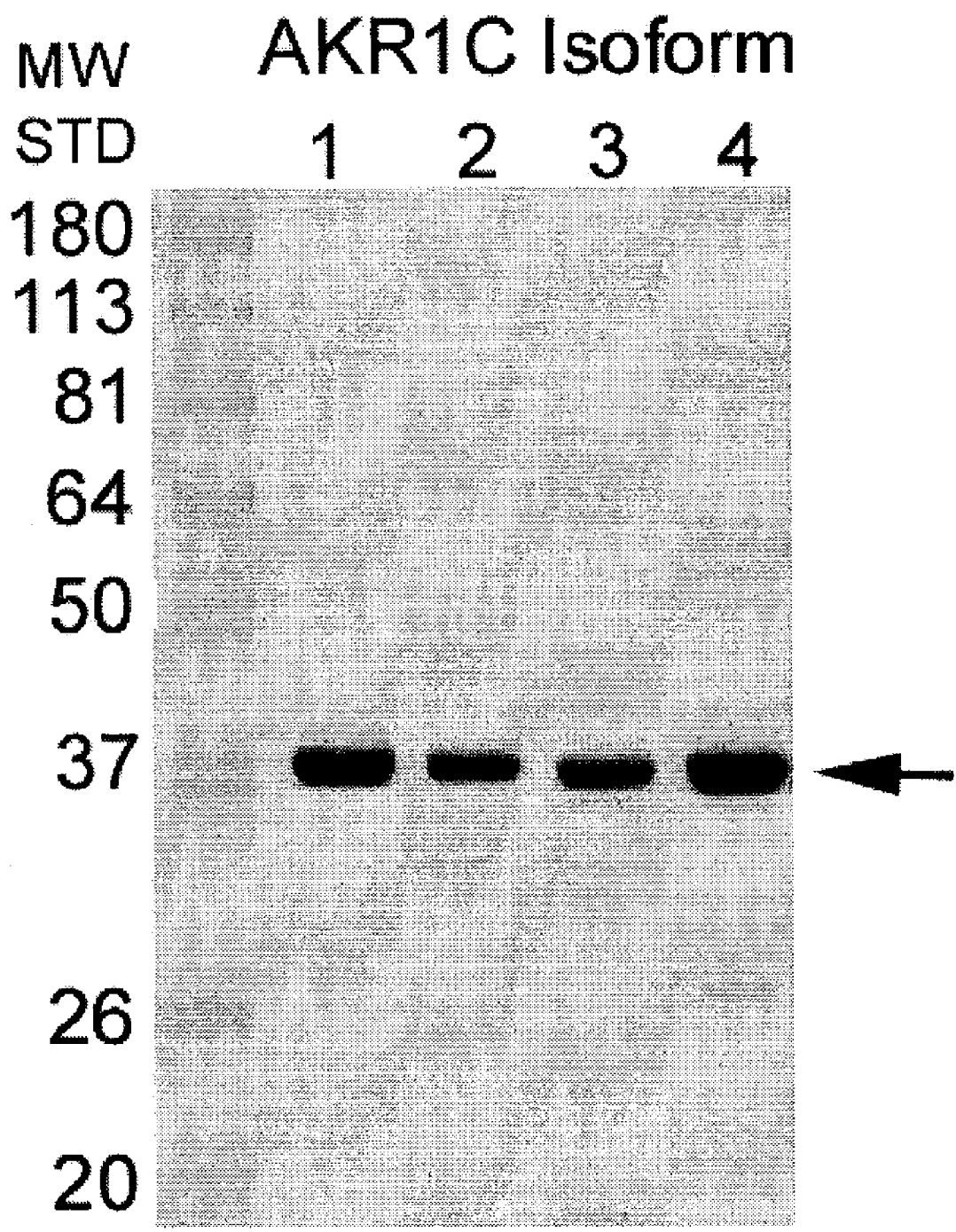
FIG. 4 illustrates results from purification of AKR1C isoforms 1, 2, 3, and 4. The arrow indicates the purified human AKR1C isoforms.

*E. Coli* were transformed with plasmid constructs encoding the human AKR1C isoforms and protein expression from the plasmid was induced by incubating with 1 mM IPTG for 2.5 hours. Bacteria were pelleted, lysed, and the AKR1C isoforms purified from the lysates by eluting from an anion exchange column and a Cibacron Blue affinity column. See, e.g., Bez, et. al., *J. Biol. Chem.* 271:30190 (1996). Purified proteins were resolved on a reduced polyacrylamide gel and the proteins stained with Coomassie Blue. See, FIG. 4. The arrow indicates the purified human AKR1C isoforms.

Example 10

This example demonstrates that the purified human AKR1C isoforms retain enzyme activity following purification and thus can be used in a high-throughput screen to identify compounds that modulate AKR1C enzyme activity.

Figure 5:
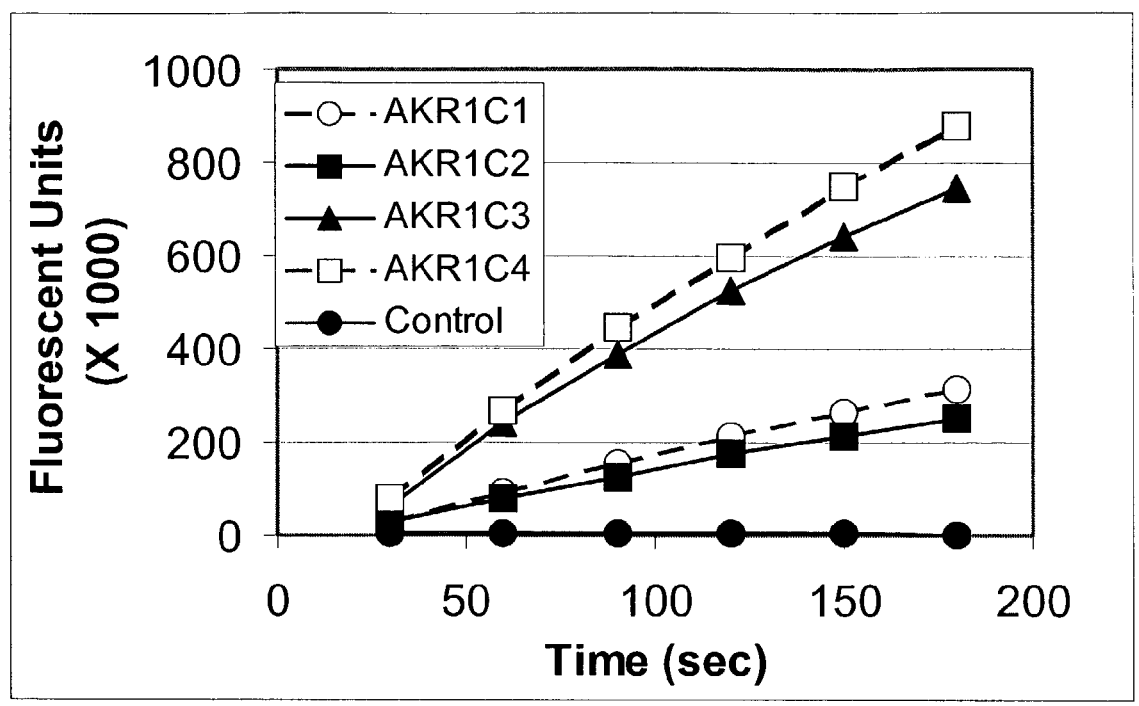
FIG. 5 illustrates the activity of purified AKR1C isoforms by measuring the oxidation of 1-acenaphthenol.

The oxidation of 1-acenaphthenol by AKR1C isoforms was determined in 200 μl containing 100 mM potassium phosphate (pH 7.0), 2.3 mM NADP, 1 mM 1-acenaphthenol, 4% methanol and 25 μl of the purified enzyme preparation. Control incubations were done in the absence of substrate (1-acenaphthenol). The rate of product formation was measured by monitoring the increase in fluorescence that occurs with NADPH production (Excitation 360 nm, Emission 450 nm). See, FIG. 5.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying an agent for modulating insulin sensitivity in a cell, the method comprising the steps of:

(i) contacting a cell comprising an aldo-keto reductase 1C (AKR1C) polypeptide or fragment thereof with an agent, wherein the AKR1C polypeptide or the fragment thereof catalyzes the interconversion of 9α, 11β-prostaglandin $F_{2\alpha}$ (9α, 11β-$PGF_{2\alpha}$) from prostaglandin D2 and wherein the polypeptide or fragment thereof is at least 95% identical to SEQ ID NO: 1, SEQ ID NO: 7, SEQ ID NO: 17, or SEQ ID NO:23;

(ii) selecting an agent that modulates the catalytic activity of the AKR1C polypeptide or fragment thereof compared to the catalytic activity of the AKR1C polypeptide in the absence of the agent, and (iii) contacting the agent selected in step ii) to a cell and testing the insulin sensitivity of the cell, thereby identifying an agent that modulates insulin sensitivity.

2. The method of claim 1, further comprising selecting an agent that decreases insulin resistance in the cell compared to insulin resistance of the cell in the absence of the agent.

3. The method of claim 1, wherein the catalytic activity of the AKR1C polypeptide is determined by measuring a change in the level of a catalytic product or substrate.

4. The method of claim 3, wherein the catalytic product or substrate is 9α,11β-$PGF_{2\alpha}$.

5. The method of claim 3, wherein the catalytic product or substrate is prostaglandin D2.

6. The method of claim 1, wherein the contacting step is performed in vitro.

7. The method of claim 1, wherein the AKR1C polypeptide or fragment thereof is expressed in a cell and the cell is contacted with the agent.

8. The method of claim 1, wherein the agent increases the catalytic activity of the AKR1C polypeptide or fragment thereof.

9. The method of claim 1, wherein the agent decreases the catalytic activity of the AKR1C polypeptide or fragment thereof.

10. The method of claim 1, further comprising the steps of administering the agent to an animal exhibiting insulin resistance and testing the animal for modulated insulin resistance.

11. The method of claim 1, further comprising the steps of contacting a cell expressing an AKR1C polypeptide or fragment thereof with the agent and testing the cell for modulated peroxisome proliferation activated receptor (PPAR) activity.

12. The method of claim 1, wherein the AKR1C polypeptide comprises SEQ ID NO:1.

13. The method of claim 1, wherein the AKR1C polypeptide comprises SEQ ID NO:7.

14. The method of claim 1, wherein the AKR1C polypeptide comprises SEQ ID NO:17.

15. The method of claim 1, wherein the AKR1C polypeptide comprises SEQ ID NO:23.

16. A method for identifying an agent for modulating insulin sensitivity in a cell, the method comprising the steps of:

(i) contacting a cell comprising an aldo-keto reductase 1C (AKR1C) polypeptide or fragment thereof with an agent, wherein the AKR1C polypeptide or the fragment thereof catalyzes the interconversion of 9α, 11β-prostaglandin $F_{2\alpha}$(9α, 11β-$PGF_{2\alpha}$) from prostaglandin D2 and wherein the polypeptide or fragment thereof is at least 95% identical to SEQ ID NO:1, SEQ ID NO:7, SEQ ID NO:17, or SEQ ID NO:23;

(ii) selecting an agent that modulates the expression of the AKR1C polypeptide or fragment thereof compared to a control cell not contacted with the agent by measuring the level of a transcription product encoding the AKR1C polypeptide in the cell and control cell, or measuring the level of the AKR1C polypeptide in the cell and control cell, and (iii) contacting the agent selected in step ii) to a cell and testing the insulin sensitivity of the cell; thereby identifying an agent that modulates insulin sensitivity.

17. The method of claim 16, wherein the agent increases the expression of the AKR1C polypeptide or fragment thereof.

18. The method of claim 16, wherein the agent decreases the expression of the AKR1C polypeptide or fragment thereof.

19. The method of claim 16, wherein the AKR1C polypeptide comprises SEQ ID NO:1, SEQ ID NO:7, SEQ ID NO:17, or SEQ ID NO:23.

20. The method of claim 1, wherein the AKR1C polypeptide comprises SEQ ID NO:1, SEQ ID NO:7, SEQ ID NO:17, or SEQ ID NO:23.

* * * * *

UNITED STATES PATENT AND TRADEMARK OFFICE
CERTIFICATE OF CORRECTION

| | | |
|---|---|---|
| PATENT NO. | : 7,510,851 B2 | Page 1 of 1 |
| APPLICATION NO. | : 10/321204 | |
| DATED | : March 31, 2009 | |
| INVENTOR(S) | : Waters et al. | |

It is certified that error appears in the above-identified patent and that said Letters Patent is hereby corrected as shown below:

On the cover page,

[*] Notice:  Subject to any disclaimer, the term of this patent is extended or adjusted under 35 USC 154(b) by 874 days Delete the phrase "by 874 days" and insert -- by 1548 days --

Signed and Sealed this

Twentieth Day of April, 2010

David J. Kappos
*Director of the United States Patent and Trademark Office*

SEQUENCE LISTING

<160> NUMBER OF SEQ ID NOS: 66

<210> SEQ ID NO 1
<211> LENGTH: 323
<212> TYPE: PRT
<213> ORGANISM: Homo sapiens

<400> SEQUENCE: 1

```
Met Asp Ser Lys Tyr Gln Cys Val Lys Leu Asn Asp Gly His Phe Met
 1               5                  10                  15

Pro Val Leu Gly Phe Gly Thr Tyr Ala Pro Ala Glu Val Pro Lys Ser
            20                  25                  30

Lys Ala Leu Glu Ala Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Cys Asn Ser His Arg Pro Glu Leu Val Arg
                85                  90                  95

Pro Ala Leu Glu Arg Ser Leu Lys Asn Leu Gln Leu Asp Tyr Val Asp
            100                 105                 110

Leu Tyr Leu Ile His Phe Pro Val Ser Val Lys Pro Gly Glu Glu Val
        115                 120                 125

Ile Pro Lys Asp Glu Asn Gly Lys Ile Leu Phe Asp Thr Val Asp Leu
    130                 135                 140

Cys Ala Thr Trp Glu Ala Val Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175
```

```
Leu Asn Lys Pro Gly Leu Lys Tyr Lys Pro Val Cys Asn Gln Val Glu
            180                 185                 190
Cys His Pro Tyr Phe Asn Gln Arg Lys Leu Leu Asp Phe Cys Lys Ser
        195                 200                 205
Lys Asp Ile Val Leu Val Ala Tyr Ser Ala Leu Gly Ser His Arg Glu
    210                 215                 220
Glu Pro Trp Val Asp Pro Asn Ser Pro Val Leu Leu Glu Asp Pro Val
225                 230                 235                 240
Leu Cys Ala Leu Ala Lys Lys His Lys Arg Thr Pro Ala Leu Ile Ala
                245                 250                 255
Leu Arg Tyr Gln Leu Gln Arg Gly Val Val Leu Ala Lys Ser Tyr
            260                 265                 270
Asn Glu Gln Arg Ile Arg Gln Asn Val Gln Val Phe Glu Phe Gln Leu
        275                 280                 285
Thr Ser Glu Glu Met Lys Ala Ile Asp Gly Leu Asn Arg Asn Val Arg
    290                 295                 300
Tyr Leu Thr Leu Asp Ile Phe Ala Gly Pro Pro Asn Tyr Pro Phe Ser
305                 310                 315                 320
Asp Glu Tyr

<210> SEQ ID NO 2
<211> LENGTH: 1146
<212> TYPE: DNA
<213> ORGANISM: Homo sapiens

<400> SEQUENCE: 2
ctgtcctggg atttggcacc tatgcgcctg cagaggttcc taaaagtaaa gctttagagg     60
ccaccaaatt ggcaattgaa gctggcttcc gccatattga ttctgctcat ttatacaata    120
atgaggagca ggttggactg ccatccgaa gcaagattgc agatggcagt gtgaagagag     180
aagacatatt ctacacttca aagctttggt gcaattccca tcgaccagag ttggtccgac    240
cagccttgga aaggtcactg aaaaatcttc aattggatta tgttgacctc taccttattc    300
attttccagt gtctgtaaag ccaggtgagg aagtgatccc aaaagatgaa atgaaaaa     360
tactatttga cacagtggat ctctgtgcca cgtgggaggc cgtggagaag tgtaaagatg    420
caggattggc caagtccatc ggggtgtcca acttcaaccg caggcagctg agatgatcc     480
tcaacaagcc agggctcaag tacaagcctg tctgcaacca ggtggaatgt catccttact    540
tcaaccagag aaaactgctg gatttctgca agtcaaaaga cattgttctg gttgcctata    600
gtgctctggg atcccaccga agaaccat gggtggaccc gaactcccg gtgctcttgg       660
aggacccagt cctttgtgcc ttggcaaaaa agcacaagcg aaccccagcc ctgattgccc    720
tgcgctacca gctacagcgt ggggttgtgg tcctggccaa gagctacaat gagcagcgca    780
tcagacagaa cgtgcaggtg tttgaattcc agttgacttc agaggagatg aaagccatag    840
atggcctaaa cagaaatgtg cgatatttga cccttgatat ttttgctggc cccctaatt     900
atccattttc tgatgaatat aacatggag gcattgcat gaggtctgcc agaaggccct     960
gcgtgtggat ggtgacacag aggatggctc tatgctggtg actggacaca tcgcctctgg   1020
ttaaatctct cctgcttggt gatttcagca agctacagca aagcccattg ccagaaagg    1080
aaagacaata attttgtttt ttcatttga aaaaattaaa tgctctctcc taaagattct   1140
tcacct                                                              1146
```

<210> SEQ ID NO 3
<211> LENGTH: 1207
<212> TYPE: DNA
<213> ORGANISM: Homo sapiens

<400> SEQUENCE: 3

| | | | | | |
|---|---|---|---|---|---|
| ccagaaatgg | attcgaaata | tcagtgtgtg | aagctgaatg | atggtcactt | catgcctgtc | 60 |
| ctgggatttg | gcacctatgc | gcctgcagag | gttcctaaaa | gtaaagcttt | agaggccacc | 120 |
| aaattggcaa | ttgaagctgg | cttccgccat | attgattctg | ctcatttata | caataatgag | 180 |
| gagcaggttg | gactggccat | ccgaagcaag | attgcagatg | gcagtgtgaa | gagagaagac | 240 |
| atattctaca | cttcaaagct | tggtgcaatt | cccatcgac | cagagttggt | ccgaccagcc | 300 |
| ttggaaaggt | cactgaaaaa | tcttcaattg | gattatgttg | acctctacct | tattcatttt | 360 |
| ccagtgtctg | taaagccagg | tgaggaagtg | atcccaaaag | atgaaaatgg | aaaaatacta | 420 |
| tttgacacag | tggatctctg | tgccacgtgg | gaggccgtgg | agaagtgtaa | agatgcagga | 480 |
| ttggccaagt | ccatcggggt | gtccaacttc | aaccgcaggc | agctggagat | gatcctcaac | 540 |
| aagccagggc | tcaagtacaa | gcctgtctgc | aaccaggtgg | aatgtcatcc | ttacttcaac | 600 |
| cagagaaaac | tgctggattt | ctgcaagtca | aaagacattg | ttctggttgc | ctatagtgct | 660 |
| ctgggatccc | accgaagaa | accatggggtg | gacccgaact | ccccggtgct | cttggaggac | 720 |
| ccagtccttt | gtgccttggc | aaaaaagcac | aagcgaaccc | cagccctgat | tgccctgcgc | 780 |
| taccagctac | agcgtggggt | tgtggtcctg | gccaagagct | acaatgagca | gcgcatcaga | 840 |
| cagaacgtgc | aggtgtttga | attccagttg | acttcagagg | agatgaaagc | catagatggc | 900 |
| ctaaacagaa | atgtgcgata | tttgacccctt | gatatttttg | ctggcccccc | taattatcca | 960 |
| ttttctgatg | aatattaaca | tggagggcat | tgcatgaggt | ctgccagaag | gccctgcgtg | 1020 |
| tggatggtga | cacagaggat | ggctctatgc | tggtgactgg | acacatcgcc | tctggttaaa | 1080 |
| tctctcctgc | ttggtgattt | cagcaagcta | cagcaaagcc | cattggccag | aaaggaaaga | 1140 |
| caataatttt | gttttttcat | tttgaaaaaa | ttaaatgctc | tctcctaaag | attcttcacc | 1200 |
| taaaaaa | | | | | | 1207 |

<210> SEQ ID NO 4
<211> LENGTH: 1195
<212> TYPE: DNA
<213> ORGANISM: Homo sapiens

<400> SEQUENCE: 4

| | | | | | |
|---|---|---|---|---|---|
| gaaatggatt | cgaaatatca | gtgtgtgaag | ctgaatgatg | gtcacttcat | gcctgtcctg | 60 |
| ggatttggca | cctatgcgcc | tgcagaggtt | cctaaaagta | aagctttaga | ggccaccaaa | 120 |
| ttggcaattg | aagctggctt | ccgccatatt | gattctgctc | atttatacaa | taatgaggag | 180 |
| caggttggac | tggccatccg | aagcaagatt | gcagatggca | gtgtgaagag | agaagacata | 240 |
| ttctacactt | caaagctttg | gtgcaattcc | catcgaccag | agttggtccg | accagccttg | 300 |
| gaaaggtcac | tgaaaaatct | tcaattggat | tatgttgacc | tctaccttat | tcattttcca | 360 |
| gtgtctgtaa | agccaggtga | ggaagtgatc | caaaagatg | aaaatggaaa | atactatttt | 420 |
| gacacagtgg | atctctgtgc | cacgtgggag | gccgtggaga | agtgtaaaga | tgcaggattg | 480 |
| gccaagtcca | tcggggtgtc | caacttcaac | cgcaggcagc | tggagatgat | cctcaacaag | 540 |
| ccagggctca | agtacaagcc | tgtctgcaac | caggtggaat | gtcatcctta | cttcaaccag | 600 |
| agaaaactgc | tggatttctg | caagtcaaaa | gacattgttc | tggttgccta | tagtgctctg | 660 |

| | |
|---|---|
| ggatcccacc gagaagaacc atgggtggac ccgaactccc cggtgctctt ggaggaccca | 720 |
| gtcctttgtg ccttggcaaa aaagcacaag cgaaccccag ccctgattgc cctgcgctac | 780 |
| cagctacagc gtggggttgt ggtcctggcc aagagctaca atgagcagcg catcagacag | 840 |
| aacgtgcagg tgtttgaatt ccagttgact tcagaggaga tgaaagccat agatggccta | 900 |
| aacagaaatg tgcgatattt gacccttgat attttttgctg cccccctaa ttatccattt | 960 |
| tctgatgaat attaacatgg agggcattgc atgaggtctg ccagaaggcc ctgcgtgtgg | 1020 |
| atggtgacac agaggatggc tctatgctgg tgactggaca catcgcctct ggttaaatct | 1080 |
| ctcctgcttg gtgatttcag caagctacag caaagcccat ggccagaaa ggaaagacaa | 1140 |
| taattttgtt ttttcatttt gaaaaaatta aatgctctct ccttctctaa aaaaa | 1195 |

<210> SEQ ID NO 5
<211> LENGTH: 1207
<212> TYPE: DNA
<213> ORGANISM: Homo sapiens

<400> SEQUENCE: 5

| | |
|---|---|
| ccagaaatgg attcgaaata tcagtgtgtg aagctgaatg atggtcactt catgcctgtc | 60 |
| ctgggatttg gcacctatgc gcctgcagag gttcctaaaa gtaaagcttt agaggccacc | 120 |
| aaattggcaa ttgaagctgg cttccgccat attgattctg ctcatttata caataatgag | 180 |
| gagcaggttg gactggccat ccgaagcaag attgcagatg cagtgtgaa gagagaagac | 240 |
| atattctaca cttcaaagct ttggtgcaat tcccatcgac cagagttggt ccgaccagcc | 300 |
| ttggaaaggt cactgaaaaa tcttcaattg gattatgttg acctctacct tattcatttt | 360 |
| ccagtgtctg taaagccagg tgaggaagtg atcccaaaag atgaaaatgg aaaaatacta | 420 |
| tttgacacag tggatctctg tgccacgtgg gaggccgtgg agaagtgtaa agatgcagga | 480 |
| ttggccaagt ccatcggggt gtccaacttc aaccgcaggc agctggagat gatcctcaac | 540 |
| aagccagggc tcaagtacaa gcctgtctgc aaccaggtgg aatgtcatcc ttacttcaac | 600 |
| cagagaaaac tgctggattt ctgcaagtca aaagacattg ttctggttgc ctatagtgct | 660 |
| ctgggatccc accgagaaga accatgggtg gacccgaact ccccggtgct cttggaggac | 720 |
| ccagtccttt gtgccttggc aaaaaagcac aagcgaaccc cagccctgat tgccctgcgc | 780 |
| taccagctac agcgtggggt tgtggtcctg gccaagagct acaatgagca gcgcatcaga | 840 |
| cagaacgtgc aggtgtttga attccagttg acttcagagg agatgaaagc catagatggc | 900 |
| ctaaacagaa atgtgcgata tttgaccctt gatattttg ctggccccc taattatcca | 960 |
| ttttctgatg aatattaaca tggagggcat tgcatgaggt ctgccagaag gccctgcgtg | 1020 |
| tggatggtga cacagaggat ggctctatgc tggtgactgg acacatcgcc tctggttaaa | 1080 |
| tctctcctgc ttggtgattt cagcaagcta cagcaaagcc cattggccag aaaggaaaga | 1140 |
| caataatttt gttttttcat tttgaaaaaa ttaaatgctc tcctaaag attcttcacc | 1200 |
| taaaaaa | 1207 |

<210> SEQ ID NO 6
<211> LENGTH: 1158
<212> TYPE: DNA
<213> ORGANISM: Homo sapiens

<400> SEQUENCE: 6

| | |
|---|---|
| aaatatcagt gtgtgaagct gaatgatggt cacttcatgc ctgtcctggg atttggcacc | 60 |
| tatgcgcctg cagaggttcc taaaagtaaa gctttagagg ccaccaaatt ggcaattgaa | 120 |

```
gctggcttcc gccatattga ttctgctcat ttatacaata atgaggagca ggttggactg    180
gccatccgaa gcaagattgc agatggcagt gtgaagagag aagacatatt ctacacttca    240
aagctttggt gcaattccca tcgaccagag ttggaccgac cagccttgga aaggtcactg    300
aaaaatcttc aattggatta tgttgacctc taccttattc attttccagt gtctgtaaag    360
ccaggtgagg aagtgatccc aaaagatgaa aatggaaaaa tactatttga cacagtggat    420
ctctgtgcca cgtgggaggc cgtggagaag tgtaaagatg cagaattggc caagtccatc    480
ggggtgtcca acttcaaccg cagcacgctg gagatgatcc tcaacaagcc agggctacaa    540
gtgaagcctg tctgcaacca ggtggaatgt catccttact tcaaccagag aaaactgctg    600
gatttctgca agtcaaaaga cattgttctg gttgcctata gtgctctggg atccctccga    660
gaagaaccat gggtggaccc gaactccccg gtgctcttgg aggacccagt cctttgtgcc    720
ttggcaaaaa agcacaagcg aaccccagcc ctgattgccc tgcgctacca gctacagcgt    780
ggggttgtgg tcctggccaa gagctacaat gagcagcgca tcagacagaa cgtgcaggtg    840
tttgaattcc agttgacttc agaggagatg aaagccatag atggcctaaa cagaaatgtg    900
cgatatttga cccttgatat ttttgctggc cccctaatt atccgatctc tgatgaatat    960
taacatggag ggcattgcat gaggtctgcc agaaggccct gcgtgtggat ggtgacacag   1020
aggatggctc tatgctggtg aatattaaca tggagggcat tgcatgaggt ctgccagaag   1080
gccctgcgtt gtggatggtg acacatagga tggctctatg ctggtgacgg gacacatcgc   1140
ctctggttaa atcaccaa                                                 1158

<210> SEQ ID NO 7
<211> LENGTH: 323
<212> TYPE: PRT
<213> ORGANISM: Homo sapiens

<400> SEQUENCE: 7

Met Asp Ser Lys Tyr Gln Cys Val Lys Leu Asn Asp Gly His Phe Met
 1               5                  10                  15

Pro Val Leu Gly Phe Gly Thr Tyr Ala Pro Ala Glu Val Pro Lys Ser
                20                  25                  30

Lys Ala Leu Glu Ala Val Lys Leu Ala Ile Glu Ala Gly Phe His His
            35                  40                  45

Ile Asp Ser Ala His Val Tyr Asn Asn Glu Glu Gln Val Gly Leu Ala
        50                  55                  60

Ile Arg Ser Lys Ile Ala Asp Gly Ser Val Lys Arg Glu Asp Ile Phe
 65                  70                  75                  80

Tyr Thr Ser Lys Leu Trp Ser Asn Ser His Arg Pro Glu Leu Val Arg
                85                  90                  95

Pro Ala Leu Glu Arg Ser Leu Lys Asn Leu Gln Leu Asp Tyr Val Asp
            100                 105                 110

Leu Tyr Leu Ile His Phe Pro Val Ser Val Lys Pro Gly Glu Glu Val
        115                 120                 125

Ile Pro Lys Asp Glu Asn Gly Lys Ile Leu Phe Asp Thr Val Asp Leu
    130                 135                 140

Cys Ala Thr Trp Glu Ala Met Glu Lys Cys Lys Asp Ala Gly Leu Ala
145                 150                 155                 160

Lys Ser Ile Gly Val Ser Asn Phe Asn His Arg Leu Leu Glu Met Ile
                165                 170                 175

Leu Asn Lys Pro Gly Leu Lys Tyr Lys Pro Val Cys Asn Gln Val Glu
            180                 185                 190
```

```
Cys His Pro Tyr Phe Asn Gln Arg Lys Leu Leu Asp Phe Cys Lys Ser
            195                 200                 205

Lys Asp Ile Val Leu Val Ala Tyr Ser Ala Leu Gly Ser His Arg Glu
        210                 215                 220

Glu Pro Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Leu Ala Lys Ser Tyr
            260                 265                 270

Asn Glu Gln Arg Ile Arg Gln Asn Val Gln Val Phe Glu Phe Gln Leu
                275                 280                 285

Thr Ser Glu Glu Met Lys Ala Ile Asp Gly Leu Asn Arg Asn Val Arg
290                 295                 300

Tyr Leu Thr Leu Asp Ile Phe Ala Gly Pro Pro Asn Tyr Pro Phe Ser
305                 310                 315                 320

Asp Glu Tyr

<210> SEQ ID NO 8
<211> LENGTH: 1290
<212> TYPE: DNA
<213> ORGANISM: Homo sapiens

<400> SEQUENCE: 8
gctaaccagg ccagtgacag aaatggattc gaaataccag tgtgtgaagc tgaatgatgg      60
tcacttcatg cctgtcctgg gatttggcac ctatgcgcct gcagaggttc ctaaaagtaa     120
agctctagag gccgtcaaat tggcaataga agccgggttc caccatattg attctgcaca     180
tgtttacaat aatgaggagc aggttggact ggccatccga agcaagattg cagatggcag     240
tgtgaagaga gaagacatat tctacacttc aaagctttgg agcaattccc atcgaccaga     300
gttggtccga ccagccttgg aaaggtcact gaaaaatctt caattggact atgttgaccct    360 ctatcttatt cattttccag tgtctgtaaa gccaggtgag gaagtgatcc caaaagatga     420
aaatggaaaa atactatttg acacagtgga tctctgtgcc acatgggagg ccatggagaa     480
gtgtaaagat gcaggattgg ccaagtccat cggggtgtcc aacttcaacc acaggctgct     540
ggagatgatc ctcaacaagc cagggctcaa gtacaagcct gtctgcaacc aggtggaatg     600
tcatccttac ttcaaccaga gaaaactgct ggatttctgc aagtcaaaag acattgttct     660
ggttgcctat agtgctctgg gatcccatcg agaagaacca tgggtggacc cgaactcccc     720
ggtgctcttg gaggacccag tcctttgtgc cttggcaaaa aagcacaagc gaaccccagc     780
cctgattgcc ctgcgctacc agctgcagcg tggggttgtg gtcctggcca agagctacaa     840
tgagcagcgc atcagacaga acgtgcaggt gtttgaattc cagttgactt cagaggagat     900
gaaagccata gatggcctaa acagaaatgt gcgatatttg acccttgata tttttgctgg     960 ccccccctaat tatccatttt ctgatgaata ttaacatgga gggcattgca tgaggtctgc    1020
cagaaggccc tgcgtgtgga tggtgacaca gaggatggct ctatgctggt gactggacac    1080
atcgcctctg gttaaatctc tcctgcttgg cgacttcagt aagctacagc taagcccatc    1140
ggccggaaaa gaaagacaat aattttgttt tcattttga aaaaattaaa tgctctctcc    1200
taaagattct tcacctaaaa aaaaaaaaaa aaaaaaaaa aaaaaaaaa aaaaaaaatt     1260 aaaaaaaaaa aaaaaaaaaa aaaaaaaaaa                                     1290
```

<210> SEQ ID NO 9
<211> LENGTH: 972
<212> TYPE: DNA
<213> ORGANISM: Homo sapiens

<400> SEQUENCE: 9

```
atggattcga aatatcagtg tgtgaagctg aatgatggtc acttcatgcc tgtcctggga      60
tttggcacct atgcgcctgc agaggttcct aaaagtaaag ctttagaggc caccaaattg     120
gcaattgaag ctggcttccg ccatattgat tctgctcatt tatacaataa tgaggagcag     180
gttggactgg ccatccgaag caagattgca gatggcagtg tgaagagaga agacatattc     240
tacacttcaa gctttggtg caattcccat cgaccagagt tggtccgacc agccttggaa     300
aggtcactga aaatcttca attggattat gttgacctct accttattca ttttccagtg     360
tctgtaaagc caggtgagga agtgatccca aaagatgaaa atggaaaaat actatttgac     420
acagtggatc tctgtgccac gtgggaggcc gtggagaagt gtaaagatgc aggattggcc     480
aagtccatcg gggtgtccaa cttcaaccgc aggcagctgg agatgatcct caacaagcca     540
gggctcaagt acaagcctgt ctgcaaccag gtggaatgtc atccttactt caaccagaga     600
aaactgctgg atttctgcaa gtcaaaagac attgttctgg ttgcctatag tgctctggga     660
tcccaccgag aagaaccatg ggtggacccg aactccccgg tgctcttgga ggacccagtc     720
ctttgtgcct tggcaaaaaa gcacaagcga accccagccc tgattgccct cgcgctaccag     780
ctacagcgtg gggttgtggt cctggccaag agctacaatg agcagcgcat cagacagaac     840
gtgcaggtgt ttgaattcca gttgacttca gaggagatga agcccataga tggcctaaac     900
agaaatgtgc gatatttgac ccttgatatt tttgctggcc ccctaattac tccattttct     960
gatgaatatt aa                                                        972
```

<210> SEQ ID NO 10
<211> LENGTH: 1219
<212> TYPE: DNA
<213> ORGANISM: Homo sapiens

<400> SEQUENCE: 10

```
tgctaaccag gccagtgaca gaaatggatt cgaaatacca gtgtgtgaag ctgaatgatg      60
gtcacttcat gcctgtcctg ggatttggca cctatgcgcc tgcagaggtt cctaaaagta     120
agctctaga ggccgtcaaa ttggcaatag aagccgggtt ccaccatatt gattctgcac     180
atgtttacaa taatgaggag caggttggac tggccatccg aagcaagatt gcagatggca     240
gtgtgaagag agaagacata ttctacactt caaagctttg gagcaattcc catcgaccag     300
agttggtccg accagccttg gaaaggtcac tgaaaaatct tcaattggac tatgttgacc     360
tctatcttat tcattttcca gtgtctgtaa agccaggtga ggaagtgatc ccaaaagatg     420
aaaatggaaa aatactattt gacacagtgg atctctgtgc cacgtgggag gccatggaga     480
gtgtaaaga tgcaggattg gccaagtcca tcggggtgtc caacttcaac cacaggctgc     540
tggagatgat cctcaacaag ccagggctca gtacaagcc tgtctgcaac caggtggaat     600
gtcatcctta cttcaaccag agaaaactgc tggatttctg caagtcaaaa gacattgttc     660
tggttgccta tagtgctctg gatcccatc gagaagaacc atgggtggac cgaactccc     720
cggtgctctt ggaggaccca gtcctttgtg ccttggcaaa aaagcacaag cgaaccccag     780
ccctgattgc cctgcgctac agctgcagc gtggggttgt ggtcctggcc aagagctaca     840
atgagcagcg catcagacag aacgtgcagg tgtttgaatt ccagttgact tcagaggaga     900
tgaaagccat agatggccta aacagaaatg tgcgatattt gaccttgat attttgctg     960
```

-continued

| | |
|---|---|
| gccccccctaa ttatccattt tctgatgaat attaacatgg agggcattgc atgaggtctg | 1020 |
| ccagaaggcc ctgcgtgtgg atggtgacac agaggatggc tctatgctgg tgactggaca | 1080 |
| catcgcctct ggttaaatct ctcctgcttg gcgacttcag taagctacag ctaagcccat | 1140 |
| cggccggaaa agaaagacaa taattttgtt ttttcatttt gaaaaaatta aatgctctct | 1200 |
| cctaaagatt cttcaccta | 1219 |

<210> SEQ ID NO 11
<211> LENGTH: 972
<212> TYPE: DNA
<213> ORGANISM: Homo sapiens

<400> SEQUENCE: 11

| | |
|---|---|
| atggattcga ataccagtg tgtgaagctg aatgatggtc acttcatgcc tgtcctggga | 60 |
| tttggcacct atgcgcctgc agaggttcct aaaagtaaag ctctagaggc cgtcaaattg | 120 |
| gcaatagaag ccgggttcca ccatattgat tctgcacatg tttacaataa tgaggagcag | 180 |
| gttggactgg ccatccgaag caagattgca gatggcagtg tgaagagaga agacatattc | 240 |
| tacacttcaa gctttggag caattcccat cgaccagagt tggtccgacc agccttggaa | 300 |
| aggtcactga aaaatcttca attggactat gttgacctct atcttattca ttttccagtg | 360 |
| tctgtaaagc caggtgagga agtgatccca aaagatgaaa atggaaaaat actatttgac | 420 |
| acagtggatc tctgtgccac atgggaggcc atggagaagt gtaaagatgc aggattggcc | 480 |
| aagtccatcg gggtgtccaa cttcaaccac aggctgctgg agatgatcct caacaagcca | 540 |
| gggctcaagt acaagcctgt ctgcaaccag gtggaatgtc atccttactt caaccagaga | 600 |
| aaactgctgg atttctgcaa gtcaaaagac attgttctgg ttgcctatag tgctctggga | 660 |
| tcccatcgag aagaaccatg ggtggacccg aactccccgg tgctcttgga ggacccagtc | 720 |
| ctttgtgcct tggcaaaaaa gcacaagcga acccccagccc tgattgccct gcgctaccag | 780 |
| ctgcagcgtg gggttgtggt cctggccaag agctacaatg agcagcgcat cagacagaac | 840 |
| gtgcaggtgt ttgaattcca gttgacttca gaggagatga agccataga tggcctaaac | 900 |
| agaaatgtgc gatatttgac ccttgatatt tttgctggcc cccctaatta tccatttttct | 960 |
| gatgaatatt aa | 972 |

<210> SEQ ID NO 12
<211> LENGTH: 1064
<212> TYPE: DNA
<213> ORGANISM: Homo sapiens

<400> SEQUENCE: 12

| | |
|---|---|
| atggattcga ataccagtg tgtgaagctg aatgatggtc acttcatgcc tgtcctggga | 60 |
| tttggcacct atgcgcctgc agaggttcct aaaagtaaag ctctagaggc cgtcaaattg | 120 |
| gcaatagaag ccgggtacca ccatattgat tctgcacatg tttacaataa tgaggagcag | 180 |
| gttggactgg ccatccgaag caagattgca gatggcagtg tgaagagaga agacatattc | 240 |
| tacacttcaa gctttggag caattcccat cgaccagagt tggtccgacc agccttggaa | 300 |
| aggtcactga aaaatcttca attggactat gctgacctct atcttattca ttttccagtg | 360 |
| tctgtaaagc caggtgagga agtgatccca aaagatgaaa atggaaaaat actatttgac | 420 |
| acagtggatc tctgtgccac atgggaggcc atggagaagt gtaaagatgc aggattggcc | 480 |
| aagtccatcg gggtgtccaa cttcaaccac aggctgctgg agatgatcct caacgagcca | 540 |
| gggctcaagt acgagcctgt ctgcaaccag gtggaatgtc atccttactt caaccagaga | 600 |

```
aaactgctgg atttctgcaa gtcaaaagac attgttctgg ttgcctatag tgctctggga    660
tcccatcgag aagaaccatg ggtggacccg aactccccgg tgctcttgga ggacccagtc    720
ctttgtgcct tggcaaaaaa gcacaagcga accccagccc tgattgccct gcgctaccag    780
ctgcagcgtg gggttgtggt cctggccaag agctacaatg agcagcgcat cagacagaac    840
gtgcaggtgt ttgaattcca gttgacttca gaggagatga agccataga tggcctaaac     900 agaaatgtgc gatatttgac ccttgatatt tttgctggcc cccctaatta tccgatttct    960
gatgaatatt aacatggagg gcattgcatg aggtctgcca aaggccctg cgtgtggatg     1020 gtgacacaga ggatggctct atgctggtga ctggacacat ggcc                     1064
```

<210> SEQ ID NO 13
<211> LENGTH: 972
<212> TYPE: DNA
<213> ORGANISM: Homo sapiens

<400> SEQUENCE: 13

```
atggattcga ataccagtg tgtgaagctg aatgatggtc acttcatgcc tgtcctggga     60
tttggcacct atgcgcctgc agaggttcct aaaagtaaag ctctagaggc cgtcaaattg    120
gcaatagaag ccgggttcca ccatattgat tctgcacatg tttacaataa tgaggagcag   180
gttggactgg ccatccgaag caagattgca gatggcagtg tgaagagaga agacatattc   240
tacacttcaa gctttggag caattcccat cgaccagagt tggtccgacc agccttggaa    300
aggtcactga aaaatcttca attggactat gttgacctct atcttattca ttttccagtg   360
tctgtaaagc caggtgagga agtgatccca aaagatgaaa atgaaaaaat actatttgac   420
acagtggatc tctgtgccac atgggaggcc atggagaagt gtaaagatgc aggattggcc   480
aagtccatcg gggtgtccaa cttcaaccac aggctgctgg agatgatcct caacaagcca   540
gggctcaagt acaagcctgt ctgcaaccag gtggaatgtc atccttactt caaccagaga   600
aaactgctgg atttctgcaa gtcaaaagac attgttctgg ttgcctatag tgctctggga   660
tcccatcgag aagaaccatg ggtggacccg aactccccgg tgctcttgga ggacccagtc   720
ctttgtgcct tggcaaaaaa gcacaagcga accccagccc tgattgccct gcgctaccag   780
ctgcagcgtg gggttgtggt cctggccaag agctacaatg agcagcgcat cagacagaac   840
gtgcaggtgt ttgaattcca gttgacttca gaggagatga agccataga tggcctaaac    900 agaaatgtgc gatatttgac ccttgatatt tttgctggcc cccctaatta tccatttct    960 gatgaatatt aa                                                        972
```

<210> SEQ ID NO 14
<211> LENGTH: 972
<212> TYPE: DNA
<213> ORGANISM: Homo sapiens

<400> SEQUENCE: 14

```
atggattcga atatcagtg tgtgaagctg aatgatggtc acttcatgcc tgtcctggga     60
tttggcacct atgcgcctgc agaggttcct aaaagtaaag ctttagaggc caccaaattg    120
gcaattgaag ctggcttccg ccatattgat tctgctcatt tatacaataa tgaggagcag    180
gttggactgg ccatccgaag caagattgca gatggcagtg tgaagagaga agacatattc   240
tacacttcaa gctttggtg caattcccat cgaccagagt tggtccgacc agccttggaa    300
aggtcactga aaaatcttca attggattat gttgacctct accttattca ttttccagtg   360
tctgtaaagc caggtgagga agtgatccca aaagatgaaa atgaaaaaat actatttgac   420
```

```
acagtggatc tctgtgccac gtgggaggcc gtggagaagt gtaaagatgc aggattggcc      480
aagtccatcg gggtgtccaa cttcaaccgc aggcagctgg agatgatcct caacaagcca      540
gggctcaagt acaagcctgt ctgcaaccag gtggaatgtc atccttactt caaccagaga      600
aaactgctgg atttctgcaa gtcaaaagac attgttctgg ttgcctatag tgctctggga      660
tcccaccgag aagaaccatg ggtggacccg aactccccgg tgctcttgga ggacccagtc      720
ctttgtgcct tggcaaaaaa gcacaagcga accccagccc tgattgccct cgctaccag       780 ctacagcgtg gggttgtggt cctggccaag agctacaatg agcagcgcat cagacagaac      840
gtgcaggtgt ttgaattcca gttgacttca gaggagatga agccataga tggcctaaac       900 agaaatgtgc gatatttgac ccttgatatt tttgctggcc cccctaatta tccattttct      960
gatgaatatt aa                                                          972
```

<210> SEQ ID NO 15
<211> LENGTH: 1194
<212> TYPE: DNA
<213> ORGANISM: Homo sapiens

<400> SEQUENCE: 15

```
acagaaatgg attcgaaata ccagtgtgtg aagctgaatg atggtcactt catgcctgtc       60
ctgggatttg gcacctatgc gcctgcagag gttcctaaaa gtaaagctct agaggccgtc      120
aaattggcaa tagaagccgg gttccaccat attgattctg cacatgttta caataatgag      180
gagcaggttg gactggccat ccgaagcaag attgcagatg gcagtgtgaa gagagaagac      240
atattctaca cttcaaagct ttggagcaat tcccatcgac cagagttggt ccgaccagcc      300
ttggaaaggt cactgaaaaa tcttcaattg gactatgttg acctctatct tattcatttt      360
ccagtgtctg taaagccagg tgaggaagtg atcccaaaag atgaaatgg aaaaatacta      420 tttgacacag tggatctctg tgccacatgg gaggccatgg agaagtgtaa agatgcagga      480
ttggccaagt ccatcgggt gtccaacttc aaccacaggc tgctggagat gatcctcaac      540
gagccagggc tcaagtacga gcctgtctgc aaccaggtgg aatgtcatcc ttacttcaac      600
cagagaaaac tgctggattt ctgcaagtca aaagacattg ttctggttgc ctatagtgct      660
ctgggatccc atcgagaaga accatgggtg gacccgaact ccccggtgct cttggaggac      720
ccagtccttt gtgccttggc aaaaaagcac aagcgaaccc cagccctgat tgccctgcgc      780
taccagctgc agcgtggggt tgtggtcctg gccaagagct acaatgagca gcgcatcaga      840
cagaacgtgc aggtgtttga attccagttg acttcagagg agatgaaagc catagatggc      900
ctaaacagaa atgtgcgata tttgacccct tgatattttg ctggcccccc taattatccg      960
atttctgatg aatattaaca tggagggcat tgcatgaggt ctgccagaag gccctgcgtg     1020
tggatggtga cacagaggat ggctctatgc tggtgactgg acacatggcc tctggttaaa     1080
tctctcctgc ttggcgactt gagtaagcta cagctaagcc catcggccgg aaaagaaaga     1140
caataatggg gttggggatg gggaaaaaat gaaatgctgg gtccaaaaaa aaaa           1194
```

<210> SEQ ID NO 16
<211> LENGTH: 972
<212> TYPE: DNA
<213> ORGANISM: Homo sapiens

<400> SEQUENCE: 16

```
atggattcga ataccagtgt gtgaagctg aatgatggtc acttcatgcc tgtcctggga       60
tttggcacct atgcgcctgc agaggttcct aaaagtaaag ctctagaggc cgtcaaattg     120
```

```
gcaatagaag ccgggttcca ccatattgat tctgcacatg tttacaataa tgaggagcag    180
gttggactgg ccatccgaag caagattgca gatggcagtg tgaagagaga agacatattc    240
tacacttcaa agctttggag caattcccat cgaccagagt tggtccgacc agccttggaa    300
aggtcactga aaaatcttca attggactat gttgacctct atcttattca ttttccagtg    360
tctgtaaagc caggtgagga agtgatccca aaagatgaaa atggaaaaat actatttgac    420
acagtggatc tctgtgccac atgggaggcc atggagaagt gtaaagatgc aggattggcc    480
aagtccatcg gggtgtccaa cttcaaccac aggctgctgg agatgatcct caacaagcca    540
gggctcaagt acaagcctgt ctgcaaccag gtggaatgtc atccttactt caaccagaga    600
aaactgctgg atttctgcaa gtcaaaagac attgttctgg ttgcctatag tgctctggga    660
tcccatcgag aagaaccatg ggtggacccg aactccccgg tgctcttgga ggacccagtc    720
ctttgtgcct tggcaaaaaa gcacaagcga accccagccc tgattgccct gcgctaccag    780
ctgcagcgtg gggttgtggt cctggccaag agctacaatg agcagcgcat cagacagaac    840
gtgcaggtgt ttgaattcca gttgacttca gaggagatga agccataga tggcctaaac    900 agaaatgtgc gatatttgac ccttgatatt tttgctggcc cccctaatta tccatttttct    960 gatgaatatt aa                                                        972

<210> SEQ ID NO 17
<211> LENGTH: 323
<212> TYPE: PRT
<213> ORGANISM: Homo sapiens

<400> SEQUENCE: 17

Met Asp Ser Lys Gln Gln Cys Val Lys Leu Asn Asp Gly His Phe Met
  1               5                  10                  15

Pro Val Leu Gly Phe Gly Thr Tyr Ala Pro Glu Val Pro Arg Ser
                 20                  25                  30

Lys Ala Leu Glu Val Ser Lys Leu Ala Ile Glu Ala Gly Phe Arg His
             35                  40                  45

Ile Asp Ser Ala His Leu Tyr Asn Asn Glu Glu Gln Val Gly Leu Ala
         50                  55                  60

Ile Arg Ser Lys Ile Ala Asp Gly Ser Val Lys Arg Glu Asp Ile Phe
     65                  70                  75                  80

Tyr Thr Ser Lys Leu Trp Ser Thr Ser His Arg Pro Glu Leu Val Arg
                 85                  90                  95

Pro Ala Leu Glu Asn Ser Leu Lys Lys Ala Gln Leu Asp Tyr Val Asp
            100                 105                 110

Leu Tyr Leu Ile His Ser Pro Met Ser Leu Lys Pro Gly Glu Glu Leu
        115                 120                 125

Ser Pro Thr Asp Glu Asn Gly Lys Val Ile Phe Asp Ile Val Asp Leu
    130                 135                 140

Cys Thr Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Arg Ser Lys Leu Leu Asp Phe Cys Lys Ser
        195                 200                 205

Lys Asp Ile Val Leu Val Ala Tyr Ser Ala Leu Gly Ser Gln Arg Asp
    210                 215                 220
```

```
Lys Arg Trp Val Asp Pro Asn Ser Pro Val Leu Glu Asp Pro Val
225                 230                 235                 240

Leu Cys Ala Leu Ala Lys Lys His Lys Arg Thr Pro Ala Leu Ile Ala
            245                 250                 255

Leu Arg Tyr Gln Leu Gln Arg Gly Val Val Leu Ala Arg Ser Tyr
        260                 265                 270

Asn Glu Gln Arg Ile Arg Gln Asn Val Gln Val Phe Glu Phe Gln Leu
        275                 280                 285

Thr Ala Glu Asp Met Lys Ala Ile Asp Gly Leu Asp Arg Asn Leu His
290                 295                 300

Tyr Phe Asn Ser Asp Ser Phe Ala Ser His Pro Asn Tyr Pro Tyr Ser
305                 310                 315                 320

Asp Glu Tyr

<210> SEQ ID NO 18
<211> LENGTH: 1223
<212> TYPE: DNA
<213> ORGANISM: Homo sapiens

<400> SEQUENCE: 18
aattccgggc agcagcaaac atttgctagt cagacaagtg acagggaatg gattccaaac      60
agcagtgtgt aaagctaaat gatggccact tcatgcctgt attgggattt ggacctatg     120
cacctccaga ggttccgaga agtaaagctt tggaggtcac aaaattagca atagaagctg     180
ggttccgcca tatagattct gctcatttat acaataatga ggagcaggtt ggactggcca     240
tccgaagcaa gattgcagat ggcagtgtga agagagaaga catattctac acttcaaagc     300
tttggtccac ttttcatcga ccagagttgg tccgaccagc cttggaaaac tcactgaaaa     360
aagctcaatt ggactatgtt gacctctatc ttattcattc ccaatgtctc taaagccag     420
gtgaggaact ttcaccaaca gatgaaaatg gaaagtaat atttgacata gtggatctct     480
gtaccacctg ggaggccatg gagaagtgta aggatgcagg attggccaag tccattgggg     540
tgtcaaactt caaccgcagg cagctggaga tgatcctcaa caagccagga ctcaagtaca     600
agcctgtctg caaccaggta gaatgtcatc cgtatttcaa ccggagtaaa ttgctagatt     660
tctgcaagtc gaaagatatt gttctggttg cctatagtgc tctgggatct caacgagaca     720
aacgatgggt ggacccgaac tccccggtgc tcttggagga cccagtcctt tgtgccttgg     780
caaaaaagca aagcgaaacc ccagccctga ttgccctgcg ctaccagctg cagcgtgggg     840
ttgtggtcct ggccaagagc tacaatgagc agcgcatcag acagaacgtg caggttttg     900
agttccagtt gactgcagag gacatgaaag ccatagatgg cctagacaga aatctccact     960
attttaacag tgatagtttt gctagccacc ctaattatcc atattcagat gaatattaac    1020
atggagggct ttgcctgatg tctaccagaa gccctgtgtg tggatggtga cgcagaggac    1080
gtctctatgc cggtgactgg acatatcacc tctacttaaa tccgtcctgt ttagcgactt    1140
cagtcaacta cagctgagtc cataggccag aaagacaata aatttttatc attttgaaat    1200
aaaaaaaaaa aaaaaccgga att                                            1223

<210> SEQ ID NO 19
<211> LENGTH: 1204
<212> TYPE: DNA
<213> ORGANISM: Homo sapiens
```

```
<400> SEQUENCE: 19
ctctgaggag aagcagcagc aaacatttgc tagtcagaca agtgacaggg aatggattcc      60
aaacagcagt gtgtaaagct aaatgatggc cacttcatgc ctgtattggg atttggcacc    120
tatgcacctc cagaggttcc gagaagtaaa gctttggagg tcacaaaatt agcaatagaa    180
gctgggttcc gccatataga ttctgctcat ttatacaata atgaggagca ggttggactg    240
gccatccgaa gcaagattgc agatggcagt gtgaagagag aagacatatt ctacacttca    300
aagctttggt ccacttttca tcgaccagag ttggtccgac agccttgga aaactcactg     360 aaaaagctc aattgactac tgttgacctc tatcttattc attctccaat gtctctaaag     420
ccaggtgagg aactttcacc aacagatgaa aatggaaaag taatatttga catagtggat    480
ctctgtacca cctgggaggc catggagaag tgtaaggatg caggattggc caagtccatt    540
ggggtgtcaa acttcaaccg caggcagctg agatgatcc tcaacaagcc aggactcaag     600
tacaagcctg tctgcaacca ggtagaatgt catccgtatt tcaaccggag taaattgcta    660
gatttctgca gtcgaaaga tattgttctg gttgcctata gtgctctggg atctcaacga     720
gacaaacgat gggtggaccc gaactccccg gtgctcttgg aggacccagt cctttgtgcc    780 ttggcaaaaaa agcacaagcg aaccccagcc ctgattgccc tgcgctacca gctgcagcgt    840
ggggttgtgg tcctggccaa gagctacaat gagcagcgca tcagacagaa cgtgcaggtt    900
tttgagttcc agttgactgc agaggacatg aaagccatag atggcctaga cagaaatctc    960
cactatttta acagtgatag ttttgctagc caccctaatt atccatattc agatgaatat   1020
taacatggag agctttgcct gatgtctacc agaagccctg tgtgtggatg gtgacgcaga   1080
ggacgtctct atgccggtga ctggacatat cacctctact aaatccgtc ctgtttagcg    1140 acttcagtca actacagctg agtccatagg ccagaaagac aataaatttt tatcattttg    1200
aaat                                                               1204

<210> SEQ ID NO 20
<211> LENGTH: 972
<212> TYPE: DNA
<213> ORGANISM: Homo sapiens

<400> SEQUENCE: 20
atggattcca aacagcagtg tgtaaagcta aatgatggcc acttcatgcc tgtattggga      60
tttggcacct atgcacctcc agaggttccg agaagtaaag ctttggaggt ctcaaaatta    120
gcaatagaag ctgggttccg ccatatagat tctgctcatt tatacaataa tgaggagcag    180
gttggactgg ccatccgaag caagattgca gatggcagtg tgaagagaga agacatattc    240
tacacttcaa gctttggtc cacttctcat cgaccagagt tggtccgacc agccttggaa     300
aactcactga aaaagctca attggactat gttgacctct atcttattca ttctccaatg    360
tctctaaagc caggtgagga actttcacca acagatgaaa atggaaaagt aatatttgac    420
atagtggatc tctgtaccac ctgggaggcc atggagaagt gtaaggatgc aggattggcc    480
aagtccattg gggtgtcaaa cttcaaccgc aggcagctgg agatgatcct caacaagcca    540
ggactcaagt acaagcctgt ctgcaaccag gtagaatgtc atccgtattt caaccggagt    600
aaattgctag atttctgcaa gtcgaaagat attgttctgg ttgcctatag tgctctggga    660
tctcaacgag acaaacgatg ggtggacccg aactccccgg tgctcttgga ggacccagtc    720
ctttgtgcct tggcaaaaaa gcacaagcga accccagccc tgattgccct gcgctaccag    780
ctgcagcgtg gggttgtggt cctggccagg agctacaatg agcagcgcat cagacagaac    840
```

```
gtgcaggttt ttgagttcca gttgactgca gaggacatga aagccataga tggcctagac    900
agaaatctcc actattttaa cagtgatagt tttgctagcc accctaatta tccatattct    960
gatgaatatt aa                                                        972
```

<210> SEQ ID NO 21
<211> LENGTH: 1175
<212> TYPE: DNA
<213> ORGANISM: Homo sapiens

<400> SEQUENCE: 21

```
gtgacaggga atggattcca aacagcagtg tgtaaagcta aatgatggcc acttcatgcc     60
tgtattggga tttggcacct atgcacctcc agaggttccg agaagtaaag ctttggaggt    120
cacaaaatta gcaatagaag ctgggttccg ccatatagat tctgctcatt tatacaataa    180
tgaggagcag gttggactgg ccatccgaag caagattgca gatggcagtg ttgagagaga    240
agacatattc tacacttcaa agctttggtc cacttttcat cgaccagagt tggtccgacc    300
agccttggaa aactcactga gaaagctcaa attggactat gttgacctct atcttattca    360
ttctccaatg tctctaaagc caggtgagga acttttcacca acagatgaaa atggaaaagt    420
aatatttgac atagtggatc tctgtaccac ctgggaggcc atggagaagt gtaaggatgc    480
aggattggcc aagtccattg gggtatcaaa cttcaaccgc aggcagctgg agatcatcct    540
caacaagcca ggactcaagt acaagcctgt ctgcaaccag gtagaatgtc atccgtattt    600
caaccggagt aaaattgctag atttctgcaa gtcgaaagat attgttctgg ttgcctatag    660
tgctctggga tctcaacgag acaaacgatg ggtggacccg aactccccgg tcctcttgga    720
ggacccagtc ctttgtgcct tgcaaaaaa gcacaagcga accccagccc tgattgccct    780
gcgctaccag ctgcagcgtg gggttgtggt cctggccaag agctacaatg agcagcgcat    840
cagacagaac gtgcaggttt ttgagttcca gttgactgca gaggacatga aagccataga    900
tggcctagac agaaatctcc actattttaa cagtgatagt tttgctagcc accctaatta    960
tccatattca gatgaatatt aacatggaga ctttgcctga tgtctaccag aaggccctgt   1020
gtgtgtgtgg atggtgacgc agaggacgtc tctatgccgg tgactccaca tatcacctct   1080
acttaaatcc gtcctgttta gcgacttcag tcaacttcag ctcactccat aggccagaaa   1140
tacaataaat ttttatcatt tttaaataaa aaaaa                              1175
```

<210> SEQ ID NO 22
<211> LENGTH: 989
<212> TYPE: DNA
<213> ORGANISM: Homo sapiens

<400> SEQUENCE: 22

```
ggcttcaggg aatggattcc aaacagcagt gtgtaaagct aaatgatggc cacttcatgc     60
ctgtattggg atttggcacc tatgcacctc cagaggttcc gagaagtaaa gctttggagg    120
tctcaaaatt agcaatagaa ctgggttcc gccatataga ttctgctcat ttatacaata    180
atgaggagca ggttggactg gccatccgaa gcaagattgc agatggcagt gtgaagagag    240
aagacatatt ctacacttca aagctttggt ccacttctca tcgaccagag ttggtccgac    300
cagccttgga aaactcactg aaaaagctc aattggacta tgttgacctc tatcttattc    360
attctccaat gtctctaaag ccaggtgagg aactttcacc aacagatgaa aatggaaaag    420
taatatttga catagtggat ctctgtacca cctgggaggc catggagaag tgtaaggatg    480
caggattggc caagtccatt ggggtgtcaa acttcaaccg caggcagctg agatgatcc    540
```

-continued

```
tcaacaagcc aggactcaag tacaagcctg tctgcaacca ggtagaatgt catccgtatt    600
tcaaccggag taaattgcta gatttctgca agtcgaaaga tattgttctg ttgcctata     660
gtgctctggg atctcaacga acaaacgat gggtggaccc gaactccccg gtgctcttgg     720
aggacccagt cctttgtgcc ttggcaaaaa agcacaagcg aaccccagcc ctgattgccc    780
tgcgctacca gctgcagcgt ggggttgtgg tcctggccag gagctacaat gagcagcgca    840
tcagacagaa cgtgcaggtt tttgagttcc agttgactgc agaggacatg aaagccatag    900
atggcctaga cagaaatctc cactatttta acagtgatag ttttgctagc caccctaatt    960
atccatattc tgatgaatat taacatgga                                      989
```

<210> SEQ ID NO 23
<211> LENGTH: 323
<212> TYPE: PRT
<213> ORGANISM: Homo sapiens

<400> SEQUENCE: 23

```
Met Asp Pro Lys Tyr Gln Arg Val Glu Leu Asn Asp Gly His Phe Met
  1               5                  10                  15

Pro Val Leu Gly Phe Gly Thr Tyr Ala Pro Glu Val Pro Arg Asn
             20                  25                  30

Arg Ala Val Glu Val Thr Lys Leu Ala Ile Glu Ala Gly Phe Arg His
         35                  40                  45

Ile Asp Ser Ala Tyr Leu Tyr Asn Asn Glu Glu Gln Val Gly Leu Ala
     50                  55                  60

Ile Arg Ser Lys Ile Ala Asp Gly Ser Val Lys Arg Glu Asp Ile Phe
 65                  70                  75                  80

Tyr Thr Ser Lys Leu Trp Cys Thr Phe Phe Gln Pro Gln Met Val Gln
                 85                  90                  95

Pro Ala Leu Glu Ser Ser Leu Lys Lys Leu Gln Leu Asp Tyr Val Asp
            100                 105                 110

Leu Tyr Leu Leu His Phe Pro Met Ala Leu Lys Pro Gly Glu Thr Pro
        115                 120                 125

Leu Pro Lys Asp Glu Asn Gly Lys Val Ile Phe Asp Thr Val Asp Leu
    130                 135                 140

Ser Ala Thr Trp Glu Val Met Glu Lys Cys Lys Asp Ala Gly Leu Ala
145                 150                 155                 160

Lys Ser Ile Gly Val Ser Asn Phe Asn Cys Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Leu Asn Gln Ser Lys Leu Leu Asp Phe Cys Lys Ser
        195                 200                 205

Lys Asp Ile Val Leu Val Ala His Ser Ala Leu Gly Thr Gln Arg His
    210                 215                 220

Lys Leu Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
            260                 265                 270

Asn Glu Gln Arg Ile Arg Glu Asn Ile Gln Val Phe Glu Phe Gln Leu
        275                 280                 285
```

```
Thr Ser Glu Asp Met Lys Val Leu Asp Gly Leu Asn Arg Asn Tyr Arg
    290                 295                 300

Tyr Val Val Met Asp Phe Leu Met Asp His Pro Asp Tyr Pro Phe Ser
305                 310                 315                 320

Asp Glu Tyr

<210> SEQ ID NO 24
<211> LENGTH: 1167
<212> TYPE: DNA
<213> ORGANISM: Homo sapiens

<400> SEQUENCE: 24
gcaagcaatg gatcccaaat atcagcgtgt agagctaaat gatggtcatt tcatgcccgt      60
attgggattt ggcacctatg cacctccaga ggttccgagg aacagagctg tagaggtcac     120
caaattagca atagaagctg gcttccgcca tattgattct gcttatttat acaataatga     180
ggagcaggtt ggactggcca tccgaagcaa gattgcagat ggcagtgtga agagagaaga     240
catattctac acttcaaagc tttggtgcac tttctttcaa ccacagatgg tccaaccagc     300
cttggaaagc tcactgaaaa aacttcaact ggactatgtt gacctctatc ttcttcattt     360
cccaatggct ctcaagccag gtgagacgcc actaccaaaa gatgaaaatg gaaaagtaat     420
attcgacaca gtggatctct ctgccacatg ggaggtcatg gagaagtgta aggatgcagg     480
attggccaag tccatcgggg tgtcaaactt caactgcagg cagctggaga tgatcctcaa     540
caagccagga ctcaagtaca agcctgtctg caaccaggta gaatgtcatc cttacctcaa     600
ccagagcaaa ctgctggatt ctgcaagtc aaaagacatt gttctggttg cccacagtgc     660
tctgggaacc caacgacata aactatgggt ggacccaaac tccccagttc ttttggagga     720
cccagttctt tgtgccttag caagaaaaca caaacgaacc ccagccctga ttgccctgcg     780
ctaccagctg cagcgtgggg ttgtggtcct ggccaagagc tacaatgagc agcggatcag     840
agagaacatc caggttttg aattccagtt gacatcagag gatatgaaag ttctagatgg     900
tctaaacaga aattatcgat atgttgtcat ggattttctt atggaccatc ctgattatcc     960 atttcagat gaatattagc atagagggtg ttgcacgaca tctagcagaa ggccctgtgg    1020
tgtggatggt gatgcagagg atgtctctat gctggtgact ggacacacgg cctctggtta    1080
aatccctccc ctcctgcttg gcaacttcag ctagctagat atatccatgg tccagaaagc    1140
aaacataata aatttttatc ttgaagt                                        1167

<210> SEQ ID NO 25
<211> LENGTH: 1167
<212> TYPE: DNA
<213> ORGANISM: Homo sapiens

<400> SEQUENCE: 25
gcaagcaatg gatcccaaat atcagcgtgt agagctaaat gatggtcatt tcatgcccgt      60
attgggattt ggcacctatg cacctccaga ggttccgagg aacagagctg tagaggtcac     120
caaattagca atagaagctg gcttccgcca tattgattct gcttatttat acaataatga     180
ggagcaggtt ggactggcca tccgaagcaa gattgcagat ggcagtgtga agagagaaga     240
catattctac acttcaaagc tttggtgcac tttctttcaa ccacagatgg tccaaccagc     300
cttggaaagc tcactgaaaa aacttcaact ggactatgtt gacctctatc ttcttcattt     360
cccaatggct ctcaagccag gtgagacgcc actaccaaaa gatgaaaatg gaaaagtaat     420
attcgacaca gtggatctct ctgccacatg ggaggtcatg gagaagtgta aggatgcagg     480
```

```
attggccaag tccatcgggg tgtcaaactt caactgcagg cagctggaga tgatcctcaa    540
caagccagga ctcaagtaca agcctgtctg caaccaggta gaatgtcatc cttacctcaa    600
ccagagcaaa ctgctggatt tctgcaagtc aaaagacatt gttctggttg cccacagtgc    660
tctgggaacc caacgacata aactatgggt ggacccaaac tccccagttc ttttggagga    720
cccagttctt tgtgccttag caaagaaaca caaacgaacc ccagccctga ttgccctgcg    780
ctaccagctg cagcgtgggg ttgtggtcct ggccaagagc tacaatgagc agcggatcag    840
agagaacatc caggttttg aattccagtt gacatcagag gatatgaaag ttctagatgg      900
tctaaacaga aattatcgat atgttgtcat ggattttctt atggaccatc ctgattatcc    960
attttcagat gaatattagc atagagggtg ttgcacgaca tctagcagaa ggccctgtgg   1020
tgtggatggt gatgcagagg atgtctctat gctggtgact ggacacacgg cctctggtta   1080
aatccctccc ctcctgcttg caacttcag ctagctagat atatccatgg tccagaaagc    1140
aaacataata aattttatc ttgaagt                                         1167
```

<210> SEQ ID NO 26
<211> LENGTH: 1157
<212> TYPE: DNA
<213> ORGANISM: Homo sapiens

<400> SEQUENCE: 26

```
cgatcccaaa tatcagcgtg tagagctaaa tgatggtcac ttcatgcccg tattgggatt      60
tggcacctat gcacctccag aggttccgag gaacagagct gtagaggtca ccaaattagc    120
aatagaagct ggcttccgcc atattgattc tgcttattta acaataatg aggagcaggt     180 tggactggcc atccgaagca agattgcaga tggcagtgtg aagagagaag acatattcta    240
cacttcaaag ctttggtgca ctttctttca accacagatg gtccaaccag ccttggaaag    300
ctcactgaaa aaacttcaac tggactatgt tgacctctat cttcttcatt tcccaatggc    360
tctcaagcca ggtgagacgc cactaccaaa agatgaaaat ggaaaagtaa tattcgacac    420
agtggatctc tctgccacat gggaggtcat ggagaagtgt aaggatgcag gattggccaa    480
gtccatcggg gtgtcaaact tcaactgcag gcagctggag atgatcctca acaagccagg    540
actcaagtac aagcctgtct gcaaccaggt agaatgtcat ccttacctca accagagcaa    600
actgctggat ttctgcaagt caaaagacat tgttctggtt gcccacagtg ctctgggaac    660
ccaacgacat aaactatggg tggacccaaa ctccccagtt cttttggagg acccagttct    720
ttgtgcctta gcaaagaaac acaaacgaac cccagccctg attgccctgc gctaccagct    780
gcagcgtggg gttgtggtcc tggccaagag ctacaatgag cagcggatca gagagaacat    840
ccaggttttt gaattccagt tgacatcaga ggatatgaaa gttctagatg gtctaaacag    900
aaattatcga tatgttgtca tggattttct tatggaccat cctgattatc cattttcaga   960
tgaatattag catagagggt gttgcacgac atctagcaga aggccctgtg tgtggatggt   1020
gatgcagagg atgtctctat gctggtgact ggacacacgg cctctggtta atccctccc    1080 ctcctgcttg caacttcag ctagctagat atatccatgg tccagaaagc aaacataata    1140
aatttttatc ttgaagt                                                   1157
```

<210> SEQ ID NO 27
<211> LENGTH: 1155
<212> TYPE: DNA
<213> ORGANISM: Homo sapiens

<400> SEQUENCE: 27

```
atcccaaata tcagcgtgta gagctaaatg atggtcactt catgcccgta ttgggatttg         60
gcacctatgc acctccagag gttccgagga acagagctgt agaggtcacc aaattagcaa        120
tagaagctgg cttccgccat attgattctg cttatttata caataatgag gagcaggttg        180
gactggccat ccgaagcaag attgcagatg cagtgtgaa gagagaagac atattctaca        240
cttcaaagct ttggtgcact ttctttcaac cacagatggt ccaaccagcc ttggaaagct        300
cactgaaaaa acttcaactg gactatgttg acctctatct tcttcatttc ccaatggctc        360
tcaagccagg tgagacgcca ctaccaaaag atgaaaatgg aaaagtaata ttcgacacag        420
tggatctctc tgccacatgg gaggtcatgg agaagtgtaa ggatgcagga ttggccaagt        480
ccatcggggt gtcaaacttc aactgcaggc agctggagat gatcctcaac aagccaggac        540
tcaagtacaa gcctgtctgc aaccaggtag aatgtcatcc ttacctcaac cagagcaaac        600
tgctggattt ctgcaagtca aaagacattg ttctggttgc ccacagtgct ctgggaaccc        660
aacgacataa actatgggtg acccaaaact ccccagttct tttggaggac ccagttcttt        720
gtgccttagc aaagaaacac aaacgaaccc cagccctgat gccctgcgc taccagctgc        780
agcgtggggt tgtggtcctg gccaagagct acaatgagca gcggatcaga gagaacatcc        840
aggttttga attccagttg acatcagagg atatgaaagt tctagatggt ctaaacagaa        900
attatcgata tgttgtcatg gattttctta tggaccatcc tgattatcca ttttcagatg        960
aatattagca tagagggtgt tgcacgacat ctagcagaag gccctgtgtg tggatggtga       1020
tgcagaggat gtctctatgc tggtgactgg acacacggcc tctggttaaa tccctcccct       1080
cctgcttggc aacttcagct agctagatat atccatggtc cagaaagcaa acataataaa       1140
tttttatctt gaagt                                                        1155
```

<210> SEQ ID NO 28
<211> LENGTH: 991
<212> TYPE: DNA
<213> ORGANISM: Homo sapiens

<400> SEQUENCE: 28

```
atggatccca aatatcagcg tgtagagcta aatgatggtc atttcatgcc cgtattggga         60
tttggcaccct atgcacctcc agaggttccg aggaacagag ctgtagaggt caccaaatta        120
gcaatagaag ctggcttccg ccatattgat tctgcttatt tatacaataa tgaggagcag        180
gttggactgg ccatccgaag caagattgca gatggcagtg tgaagagaga agacatattc        240
tacacttcaa agctttggtg cactttcttt caaccacaga tggtccaacc agccttggaa        300
agctcactga aaaacttca actggactat gttgacctct atcttcttca tttcccaatg        360
gctctcaagc caggtgagac gccactacca aaagatgaaa atggaaaagt aatattcgac        420
acagtggatc tctgtgccac atgggaggtc atggagaagt gtaaggatgc aggattggcc        480
aagtccatcg ggtgtcaaa cttcaactgc aggcagctgg agatgatcct caacaagcca        540
ggactcaagt acaagcctgt ctgcaaccag gtagaatgtc atccttacct caaccagagc        600
aaactgctgg atttctgcaa gtcaaaagac attgttctgg ttgcccacag tgctctggga        660
acccaacgac ataaactatg gtggacccca aactccccag ttcttttgga ggacccagtt        720
ctttgtgcct tagcaaagaa acacaaacga accccagccc tgattgccct gcgctaccag        780
ctgcagcgtg ggttgtggt cctggccaag agctacaatg agcagcggat cagagagaac        840
atccaggttt ttgaattcca gttgacatca gaggatatga agttctaga tggtctaaac        900
```

```
agaaattatc gatatgttgt catggatttt gttatggacc atcctgatta tccatttca    960
gatgaatatt agcatagagg gtgttgcacg a                                  991
```

<210> SEQ ID NO 29
<211> LENGTH: 972
<212> TYPE: DNA
<213> ORGANISM: Homo sapiens

<400> SEQUENCE: 29

```
atggatccca atatcagcg tgtagagcta aatgatggtc acttcatgcc cgtattggga    60
tttggcacct atgcacctcc agaggttccg aggaacagag ctgtagaggt caccaaatta   120
gcaatagaag ctggcttccg ccatattgat tctgcttatt tatacaataa tgaggagcag   180
gttggactgg ccatccgaag caagattgca gatggcagtg tgaagagaga agacatattc   240
tacacttcaa agctttggtg cactttcttt caaccacaga tggtccaacc agccttggaa   300
agctcactga aaaaacttca actggactat gttgacctct atcttcttca tttcccaatg   360
gctctcaagc aggtgagac gccactacca aaagatgaaa atggaaaagt aatattcgac   420
acagtggatc tctctgccac atgggaggtc atggagaagt gtaaggatgc aggattggcc   480
aagtccatcg gggtgtcaaa cttcaactgc aggcagctgg agatgatcct caacaagcca   540
ggactcaagt acaagcctgt ctgcaaccag gtagaatgtc atccttacct caaccagagc   600
aaactgctgg atttctgcaa gtcaaaagac attgttctgg ttgcccacag tgctctggga   660
acccaacgac ataaactatg ggtggaccca aactccccag ttcttttgga ggacccagtt   720
ctttgtgcct tagcaaagaa acacaaacga accccagccc tgattgccct gcgctaccag   780
ctgcagcgtg gggttgtggt cctggccaag agctacaatg agcagcggat cagagagaac   840
atccaggttt ttgaattcca gttgacatca gaggatatga agttctaga tggtctaaac   900
agaaattatc gatatgttgt catggatttt cttatggacc atcctgatta tccatttca    960
gatgaatatt ag                                                       972
```

<210> SEQ ID NO 30
<211> LENGTH: 323
<212> TYPE: PRT
<213> ORGANISM: Oryctolagus cuniculus

<400> SEQUENCE: 30

```
Met Asp Pro Lys Phe Gln Arg Val Ala Leu Ser Asp Gly His Phe Ile
  1               5                  10                  15
Pro Val Leu Gly Phe Gly Thr Tyr Ala Pro Glu Glu Val Pro Lys Ser
                 20                  25                  30
Lys Ala Met Glu Ala Thr Lys Ile Ala Ile Asp Ala Gly Phe Arg His
             35                  40                  45
Ile Asp Ser Ala Tyr Phe Tyr Lys Asn Glu Lys Glu Val Gly Leu Ala
         50                  55                  60
Ile Arg Ser Lys Ile Ala Asp Gly Thr Val Lys Arg Glu Asp Ile Phe
 65                  70                  75                  80
Tyr Thr Ser Lys Leu Trp Cys Thr Phe His Arg Pro Glu Leu Val Arg
                 85                  90                  95
Pro Ser Leu Glu Asp Ser Leu Lys Asn Leu Gln Leu Asp Tyr Val Asp
                100                 105                 110
Leu Tyr Ile Ile His Phe Pro Thr Ala Leu Lys Pro Gly Val Glu Ile
            115                 120                 125
Ile Pro Thr Asp Glu His Gly Lys Ala Ile Phe Asp Thr Val Asp Ile
        130                 135                 140
```

```
Cys Ala Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
            165                 170                 175

Leu Asn Lys Pro Gly Leu Lys Tyr Lys Pro Val Cys Asn Gln Val Glu
        180                 185                 190

Cys His Pro Tyr Leu Asn Gln Gly Lys Leu Leu Glu Phe Cys Lys Ser
            195                 200                 205

Lys Gly Ile Val Leu Val Ala Tyr Ser Ala Leu Gly Ser His Arg Glu
        210                 215                 220

Pro Glu Trp Val Asp Gln Ser Ala Pro Val Leu Glu Asp Pro Leu
225                 230                 235                 240

Ile Gly Ala Leu Ala Lys Lys His Gln Gln Thr Pro Ala Leu Ile Ala
                245                 250                 255

Leu Arg Tyr Gln Leu Gln Arg Gly Ile Val Val Leu Ala Lys Ser Phe
            260                 265                 270

Thr Glu Lys Arg Ile Lys Glu Asn Ile Gln Val Phe Glu Phe Gln Leu
        275                 280                 285

Pro Ser Glu Asp Met Lys Val Ile Asp Ser Leu Asn Arg Asn Phe Arg
290                 295                 300

Tyr Val Thr Ala Asp Phe Ala Ile Gly His Pro Asn Tyr Pro Phe Ser
305                 310                 315                 320

Asp Glu Tyr

<210> SEQ ID NO 31
<211> LENGTH: 323
<212> TYPE: PRT
<213> ORGANISM: Bos taurus

<400> SEQUENCE: 31

Met Asp Pro Lys Gly Gln Arg Val Lys Leu Asn Asp Gly His Phe Ile
1               5                   10                  15

Pro Val Leu Gly Phe Gly Thr Phe Ala Pro Arg Glu Val Pro Lys Ser
            20                  25                  30

Glu Ala Leu Glu Val Thr Lys Phe Ala Ile Glu Ala Gly Phe Arg His
        35                  40                  45

Ile Asp Ser Ala His Leu Tyr Gln Asn Glu Glu Gln Val Gly Gln Ala
    50                  55                  60

Ile Arg Ser Lys Ile Ala Asp Gly Thr Val Lys Arg Glu Asp Ile Phe
65                  70                  75                  80

Tyr Thr Ser Lys Leu Trp Ser Thr Ser Leu Arg Pro Glu Leu Val Arg
                85                  90                  95

Pro Ala Leu Glu Lys Ser Leu Asn Asn Leu Gln Leu Asp Tyr Val Asp
            100                 105                 110

Leu Tyr Ile Ile His Phe Pro Val Ala Leu Lys Pro Gly Glu Thr Leu
        115                 120                 125

Phe Pro Thr Asp Glu Asn Gly Lys Pro Ile Phe Asp Ser Val Asp Leu
    130                 135                 140

Cys Arg Thr Trp Glu Ala Leu Glu Lys Cys Lys Asp Ala Gly Leu Thr
145                 150                 155                 160

Lys Ser Ile Gly Val Ser Asn Phe Asn His Lys Gln Leu Glu Lys Ile
            165                 170                 175

Leu Asn Lys Pro Gly Leu Lys Tyr Lys Pro Val Cys Asn Gln Val Glu
        180                 185                 190
```

```
Cys His Pro Tyr Phe Asn Gln Ser Lys Leu Leu Asp Phe Cys Lys Ser
            195                 200                 205

His Asp Ile Val Leu Val Ala Tyr Gly Ala Leu Gly Ser Gln Arg Leu
210                 215                 220

Lys Glu Trp Val Asn Pro Asn Leu Pro Phe Leu Leu Glu Asp Pro Val
225                 230                 235                 240

Leu Ser Ala Ile Ala Lys Lys His Arg Gln Thr Pro Ala Leu Val Ala
                245                 250                 255

Leu Arg Tyr Gln Ile Gln Arg Gly Val Val Leu Ala Lys Ser Tyr
            260                 265                 270

Asn Lys Lys Arg Ile Lys Glu Asn Ile Gln Val Phe Asp Phe Glu Leu
            275                 280                 285

Thr Pro Glu Asp Met Lys Ala Ile Asp Gly Leu Asn Ser Asn Met Arg
290                 295                 300

Tyr Asn Glu Leu Leu Gly Val Gly His Pro Glu Tyr Pro Phe Val
305                 310                 315                 320

Glu Glu Tyr

<210> SEQ ID NO 32
<211> LENGTH: 323
<212> TYPE: PRT
<213> ORGANISM: Mus musculus

<400> SEQUENCE: 32

Met Asp Ser Lys Gln Gln Thr Val Arg Leu Ser Asp Gly His Phe Ile
1               5                   10                  15

Pro Ile Leu Gly Phe Gly Thr Tyr Ala Pro Gln Glu Val Pro Lys Ser
                20                  25                  30

Lys Ala Thr Glu Ala Thr Lys Ile Ala Ile Asp Ala Gly Phe Arg His
            35                  40                  45

Ile Asp Ser Ala Ser Met Tyr Gln Asn Glu Lys Glu Val Gly Leu Ala
    50                  55                  60

Ile Arg Ser Lys Ile Ala Asp Gly Thr Val Lys Arg Glu Asp Ile Phe
65                  70                  75                  80

Tyr Thr Ser Lys Val Trp Cys Thr Phe His Arg Pro Glu Leu Val Arg
                85                  90                  95

Val Cys Leu Glu Gln Ser Leu Lys Gln Leu Gln Leu Asp Tyr Val Asp
            100                 105                 110

Leu Tyr Leu Ile His Phe Pro Met Ala Met Lys Pro Gly Glu Asn Tyr
        115                 120                 125

Leu Pro Lys Asp Glu Asn Gly Lys Leu Ile Tyr Asp Ala Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Lys Ile
                165                 170                 175

Leu Lys Lys Pro Gly Leu Lys Tyr Lys Pro Val Cys Asn Gln Val Glu
            180                 185                 190

Cys His Pro Tyr Leu Asn Gln Gly Lys Leu Leu Asp Phe Cys Arg Ser
        195                 200                 205

Lys Asp Ile Val Leu Val Ala Tyr Ser Ala Leu Gly Ser His Arg Glu
    210                 215                 220

Lys Gln Trp Val Asp Gln Ser Ser Pro Val Leu Leu Asp Asn Pro Val
225                 230                 235                 240
```

```
Leu Gly Ser Met Ala Lys Lys Tyr Asn Arg Thr Pro Ala Leu Ile Ala
                245                 250                 255

Leu Arg Tyr Gln Leu Gln Arg Gly Val Val Leu Ala Lys Ser Phe
            260                 265                 270

Ser Glu Lys Arg Ile Lys Glu Asn Met Gln Val Phe Glu Phe Gln Leu
            275                 280                 285

Thr Ser Glu Asp Met Lys Val Leu Asp Asp Leu Asn Lys Asn Ile Arg
        290                 295                 300

Tyr Ile Ser Gly Ser Ser Phe Lys Asp His Pro Asp Phe Pro Phe Trp
305                 310                 315                 320

Asp Glu Tyr

<210> SEQ ID NO 33
<211> LENGTH: 323
<212> TYPE: PRT
<213> ORGANISM: Bos taurus

<400> SEQUENCE: 33

Met Asp Pro Lys Ser Gln Arg Val Lys Leu Asn Asp Gly His Phe Ile
1               5                   10                  15

Pro Val Leu Gly Phe Gly Thr Tyr Ala Pro Glu Val Pro Lys Ser
            20                  25                  30

Glu Ala Leu Glu Ala Thr Lys Phe Ala Ile Glu Val Gly Phe Arg His
        35                  40                  45

Val Asp Ser Ala His Leu Tyr Gln Asn Glu Glu Gln Val Gly Gln Ala
    50                  55                  60

Ile Arg Ser Lys Ile Ala Asp Gly Thr Val Lys Arg Glu Asp Ile Phe
65                  70                  75                  80

Tyr Thr Ser Lys Leu Trp Cys Asn Ser Leu Gln Pro Glu Leu Val Arg
                85                  90                  95

Pro Ala Leu Glu Lys Ser Leu Gln Asn Leu Gln Leu Asp Tyr Val Asp
            100                 105                 110

Leu Tyr Ile Ile His Ser Pro Val Ser Leu Lys Pro Gly Asn Lys Phe
        115                 120                 125

Val Pro Lys Asp Glu Ser Gly Lys Leu Ile Phe Asp Ser Val Asp Leu
    130                 135                 140

Cys His Thr Trp Glu Ala Leu Glu Lys Cys Lys Asp Ala Gly Leu Thr
145                 150                 155                 160

Lys Ser Ile Gly Val Ser Asn Phe Asn His Lys Gln Leu Glu Lys Ile
                165                 170                 175

Leu Asn Lys Pro Gly Leu Lys Tyr Lys Pro Val Cys Asn Gln Val Glu
            180                 185                 190

Cys His Pro Tyr Leu Asn Gln Ser Lys Leu Leu Glu Phe Cys Lys Ser
        195                 200                 205

His Asp Ile Val Leu Val Ala Tyr Ala Ala Leu Gly Ala Gln Leu Leu
    210                 215                 220

Ser Glu Trp Val Asn Ser Asn Pro Val Leu Leu Glu Asp Pro Val
225                 230                 235                 240

Leu Cys Ala Ile Ala Lys Lys His Lys Gln Thr Pro Ala Leu Val Ala
                245                 250                 255

Leu Arg Tyr Gln Val Gln Arg Gly Val Val Val Leu Ala Lys Ser Phe
            260                 265                 270

Asn Lys Lys Arg Ile Lys Glu Asn Met Gln Val Phe Asp Phe Glu Leu
        275                 280                 285
```

```
Thr Pro Glu Asp Met Lys Ala Ile Asp Gly Leu Asn Arg Asn Ile Arg
        290                 295                 300

Tyr Tyr Asp Phe Gln Lys Gly Ile Gly His Pro Glu Tyr Pro Phe Ser
305                 310                 315                 320

Glu Glu Tyr

<210> SEQ ID NO 34
<211> LENGTH: 323
<212> TYPE: PRT
<213> ORGANISM: Bos taurus

<400> SEQUENCE: 34

Met Asp Pro Lys Ser Gln Arg Val Lys Phe Asn Asp Gly His Phe Ile
  1               5                  10                  15

Pro Val Leu Gly Phe Gly Thr Tyr Ala Pro Glu Glu Val Pro Lys Ser
             20                  25                  30

Glu Ala Leu Glu Ala Thr Lys Phe Ala Ile Glu Val Gly Phe Arg His
         35                  40                  45

Val Asp Ser Ala His Leu Tyr Gln Asn Glu Glu Gln Val Gly Gln Ala
 50                  55                  60

Ile Arg Ser Lys Ile Ala Asp Gly Thr Val Lys Arg Glu Asp Ile Phe
 65                  70                  75                  80

Tyr Thr Ser Lys Leu Trp Cys Asn Ser Leu Gln Pro Glu Leu Val Arg
                 85                  90                  95

Pro Ala Leu Glu Lys Ser Leu Gln Asn Leu Gln Leu Asp Tyr Val Asp
            100                 105                 110

Leu Tyr Ile Ile His Ser Pro Val Ser Leu Lys Pro Gly Asn Lys Phe
        115                 120                 125

Val Pro Lys Asp Glu Ser Gly Lys Leu Ile Phe Asp Ser Val Asp Leu
130                 135                 140

Cys His Thr Trp Glu Ala Leu Glu Lys Cys Lys Asp Ala Gly Leu Thr
145                 150                 155                 160

Lys Ser Ile Gly Val Ser Asn Phe Asn His Lys Gln Leu Glu Lys Ile
                165                 170                 175

Leu Asn Lys Pro Gly Leu Lys Tyr Lys Pro Val Cys Asn Gln Val Glu
            180                 185                 190

Cys His Pro Tyr Leu Asn Gln Ser Lys Leu Leu Glu Phe Cys Lys Ser
        195                 200                 205

His Asp Ile Val Leu Val Ala Tyr Ala Ala Leu Gly Ala Gln Leu Leu
210                 215                 220

Ser Glu Trp Val Asn Ser Asn Pro Val Leu Leu Glu Asp Pro Val
225                 230                 235                 240

Leu Cys Ala Ile Ala Lys Lys His Lys Gln Thr Pro Ala Leu Val Ala
                245                 250                 255

Leu Arg Tyr Gln Val Gln Arg Gly Val Val Leu Ala Lys Ser Phe
            260                 265                 270

Asn Lys Lys Arg Ile Lys Glu Asn Met Gln Val Phe Asp Phe Glu Leu
        275                 280                 285

Thr Pro Glu Asp Met Lys Ala Ile Asp Gly Leu Asn Arg Asn Thr Arg
290                 295                 300

Tyr Tyr Asp Phe Gln Gln Gly Ile Gly His Pro Glu Tyr Pro Phe Ser
305                 310                 315                 320

Glu Glu Tyr
```

<210> SEQ ID NO 35
<211> LENGTH: 323
<212> TYPE: PRT
<213> ORGANISM: Rattus norvegicus

<400> SEQUENCE: 35

Met Asn Ser Lys Ile Gln Lys Met Glu Leu Asn Asp Gly His Ser Ile
1               5                   10                  15

Pro Val Leu Gly Phe Gly Thr Tyr Ala Thr Glu Glu Asn Leu Arg Lys
            20                  25                  30

Lys Ser Met Glu Ser Thr Lys Ile Ala Ile Asp Val Gly Phe Arg His
        35                  40                  45

Ile Asp Cys Ser His Leu Tyr Gln Asn Glu Glu Ile Gly Gln Ala
    50                  55                  60

Ile Val Ser Lys Ile Glu Asp Gly Thr Val Lys Arg Glu Asp Ile Phe
65                  70                  75                  80

Tyr Thr Ser Lys Leu Trp Ser Thr Ser His Arg Pro Glu Leu Val Arg
                85                  90                  95

Pro Ser Leu Glu Asn Ser Leu Arg Lys Leu Asn Leu Asp Tyr Val Asp
            100                 105                 110

Leu Tyr Leu Ile His Phe Pro Val Ser Leu Lys Pro Gly Asp Glu Leu
        115                 120                 125

Leu Pro Gln Asp Glu His Gly Asn Leu Ile Leu Asp Thr Val Asp Leu
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Lys Ile
                165                 170                 175

Leu Asn Lys Pro Gly Leu Lys His Arg Pro Val Cys Asn Gln Val Glu
            180                 185                 190

Cys His Leu Tyr Leu Asn Gln Ser Lys Leu Leu Ala Tyr Cys Lys Met
        195                 200                 205

Asn Asp Ile Val Leu Val Ala Tyr Gly Ala Leu Gly Thr Gln Arg Tyr
    210                 215                 220

Lys Tyr Cys Ile Asn Glu Asp Thr Pro Val Leu Leu Asp Asp Pro Ile
225                 230                 235                 240

Leu Cys Thr Met Ala Lys Lys Tyr Lys Arg Thr Pro Ala Leu Ile Ala
                245                 250                 255

Leu Arg Tyr Gln Leu Glu Arg Gly Ile Val Thr Leu Val Lys Ser Phe
            260                 265                 270

Asn Glu Glu Arg Ile Arg Glu Asn Leu Gln Val Phe Asp Phe Gln Leu
        275                 280                 285

Ala Ser Asp Asp Met Glu Ile Leu Asn Leu Asn Asp Arg Asn Leu Arg
    290                 295                 300

Tyr Phe Pro Ala Asn Met Phe Lys Ala His Pro Asn Phe Pro Phe Ser
305                 310                 315                 320

Asp Glu Tyr

<210> SEQ ID NO 36
<211> LENGTH: 322
<212> TYPE: PRT
<213> ORGANISM: Rattus norvegicus

<400> SEQUENCE: 36

```
Met Asp Ser Ile Ser Leu Arg Val Ala Leu Asn Asp Gly Asn Phe Ile
 1               5                  10                  15

Pro Val Leu Gly Phe Gly Thr Thr Val Pro Glu Lys Val Ala Lys Asp
            20                  25                  30

Glu Val Ile Lys Ala Thr Lys Ile Ala Ile Asp Asn Gly Phe Arg His
        35                  40                  45

Phe Asp Ser Ala Tyr Leu Tyr Glu Val Glu Glu Val Gly Gln Ala
    50                  55                  60

Ile Arg Ser Lys Ile Glu Asp Gly Thr Val Lys Arg Glu Asp Ile Phe
65                  70                  75                  80

Tyr Thr Ser Lys Leu Trp Ser Thr Phe His Arg Pro Glu Leu Val Arg
                85                  90                  95

Thr Cys Leu Glu Lys Thr Leu Lys Ser Thr Gln Leu Asp Tyr Val Asp
            100                 105                 110

Leu Tyr Ile Ile His Phe Pro Met Ala Leu Gln Pro Gly Asp Ile Phe
        115                 120                 125

Phe Pro Arg Asp Glu His Gly Lys Leu Leu Phe Glu Thr Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Cys Arg Gln Leu Glu Arg Ile
                165                 170                 175

Leu Asn Lys Pro Gly Leu Lys Tyr Lys Pro Val Cys Asn Gln Val Glu
            180                 185                 190

Cys His Leu Tyr Leu Asn Gln Ser Lys Met Leu Asp Tyr Cys Lys Ser
        195                 200                 205

Lys Asp Ile Ile Leu Val Ser Tyr Cys Thr Leu Gly Ser Ser Arg Asp
    210                 215                 220

Lys Thr Trp Val Asp Gln Lys Ser Pro Val Leu Leu Asp Asp Pro Val
225                 230                 235                 240

Leu Cys Ala Ile Ala Lys Lys Tyr Lys Gln Thr Pro Ala Leu Val Ala
                245                 250                 255

Leu Arg Tyr Gln Leu Gln Arg Gly Val Val Pro Leu Ile Arg Ser Phe
            260                 265                 270

Asn Ala Lys Arg Ile Lys Glu Leu Thr Gln Val Phe Glu Phe Gln Leu
        275                 280                 285

Ala Ser Glu Asp Met Lys Ala Leu Asp Gly Leu Asn Arg Asn Phe Arg
    290                 295                 300

Tyr Asn Asn Ala Lys Tyr Phe Asp Asp His Pro Asn His Pro Phe Thr
305                 310                 315                 320

Asp Glu
```

<210> SEQ ID NO 37
<211> LENGTH: 323
<212> TYPE: PRT
<213> ORGANISM: Mus musculus

<400> SEQUENCE: 37

```
Met Asn Ser Lys Ile Gln Lys Ile Glu Leu Asn Asp Gly His Ser Ile
 1               5                  10                  15

Pro Val Leu Gly Phe Gly Thr Tyr Ala Thr Glu Glu His Leu Lys Lys
            20                  25                  30
```

```
Lys Ser Met Glu Ser Thr Lys Ile Ala Ile Asp Val Gly Phe Cys His
         35                  40                  45
Ile Asp Cys Ser His Leu Tyr Gln Asn Glu Glu Ile Gly Gln Ala
 50                  55                  60
Ile Leu Ser Lys Ile Glu Asp Gly Thr Val Lys Arg Glu Asp Ile Phe
 65                  70                  75                  80
Tyr Thr Ser Lys Leu Trp Ser Thr Ser His Arg Pro Glu Leu Val Arg
                 85                  90                  95
Pro Ser Leu Glu Asn Ser Leu Arg Lys Leu Asn Leu Asp Tyr Val Asp
                100                 105                 110
Leu Tyr Leu Ile His Phe Pro Val Ser Leu Lys Pro Gly Asn Glu Leu
            115                 120                 125
Leu Pro Lys Asp Glu His Gly Asn Leu Ile Phe Asp Thr Val Asp Leu
130                 135                 140
Cys Asp Thr Trp Glu Ala Met Glu Lys Cys Lys Asp Ala Gly Leu Ala
145                 150                 155                 160
Lys Ser Ile Gly Val Ser Asn Phe Asn Arg Arg Gln Leu Glu Met Ile
                165                 170                 175
Leu Asn Lys Pro Gly Leu Lys Tyr Lys Pro Val Cys Asn Gln Val Glu
            180                 185                 190
Cys His Leu Tyr Leu Asn Gln Ser Lys Leu Leu Ala Tyr Cys Lys Met
        195                 200                 205
Asn Asp Ile Val Leu Val Ala Tyr Gly Ala Leu Gly Thr Gln Arg Tyr
    210                 215                 220
Lys Tyr Cys Ile Asn Glu Asp Thr Pro Val Leu Leu Asp Asp Pro Val
225                 230                 235                 240
Leu Cys Ala Met Ala Lys Lys Tyr Lys Arg Thr Pro Ala Leu Ile Ala
                245                 250                 255
Leu Arg Tyr Gln Leu Asp Arg Gly Ile Val Ala Leu Ala Lys Ser Phe
            260                 265                 270
Asn Glu Glu Arg Ile Arg Glu Asn Met Gln Val Phe Asp Phe Gln Leu
        275                 280                 285
Ala Ser Asp Asp Met Lys Ile Leu Asp Gly Leu Asp Arg Asn Leu Arg
    290                 295                 300
Tyr Phe Pro Ala Asp Met Phe Lys Ala His Pro Asn Phe Pro Phe Phe
305                 310                 315                 320
Asp Glu Tyr

<210> SEQ ID NO 38
<211> LENGTH: 1193
<212> TYPE: DNA
<213> ORGANISM: Mus musculus

<400> SEQUENCE: 38
agagaatctt ctaggtcaga gcagtggctg agaatgaatt ccaaaattca gaagatagaa      60
ttaaatgatg gtcactccat tcctgtcctg ggctttggca cctatgcaac tgaagagcat     120
ctcaagaaaa agtctatgga gtccaccaaa atagctatag atgttgggtt ctgccatatt     180
gattgttctc acttgtacca gaatgaagaa gagataggcc aggccattct aagcaagatt     240
gaagatggca ctgtgaaaag ggaagatata ttctatactt cgaagctttg gtcaacttcc     300
catcgtccag agttggtcag acccagcttg gaaaattccc tgaggaaact taatttggac     360
tatgtagacc tctatctcat tcatttccca gtgtctctga agccagggaa tgagcttttg     420
cctaaagatg agcatggaaa cttaatattt gacacagtgg atctctgtga cacatgggag     480
```

-continued

```
gccatggaga agtgtaagga tgcagggctg gccaagtcca tcggggtgtc taactttaac      540
cgtagacaac tggagatgat cctgaacaag ccagggctca gtacaagcc tgtgtgcaac       600 caggtagaat gccatcttta tctcaaccag agcaagctgc tggcctactg caagatgaat      660
gacattgttc tggttgccta tggtgccctg ggaactcaaa gatacaaata ctgtataaat      720
gaggataccc cagttctctt ggatgatcca gttctttgtg ccatggcaaa gaagtacaag      780
cggactccag ccctgattgc ccttcgctac cagctggacc gtgggattgt ggccctagcc      840
aagagtttca atgaggagag aatcagagaa acatgcagg tctttgattt ccaattggct       900
tcagatgaca tgaaaatttt agatggcctg gacagaaatc ttcggtactt tcctgctgat      960
atgtttaagg ctcaccctaa cttttccattc ttcgatgaat attaagatgg aggcccttgc     1020
cacgagttct attagaagat cttttgtgtg atgctggact ctcagatgcc aataactcga      1080
cacaccgcct ccaatcactg cttagcaact caccccagt taattcaata aattttgctt       1140 ctttctata aataaataaa aatattttgc tttaaaaaaa aaaaaaaaa aaa               1193
```

<210> SEQ ID NO 39
<211> LENGTH: 323
<212> TYPE: PRT
<213> ORGANISM: Mus musculus

<400> SEQUENCE: 39

```
Met Asn Ser Val Ser Pro Arg Val Val Leu Asn Asp Gly His Phe Ile
  1               5                  10                  15

Pro Ala Leu Gly Phe Gly Thr Thr Val Pro Asp Lys Val Pro Lys Asp
                 20                  25                  30

Glu Leu Ile Lys Ala Thr Lys Ile Ala Ile Asp Thr Gly Phe Arg His
             35                  40                  45

Phe Asp Ser Ala Tyr Leu Tyr Gln Ile Glu Glu Val Gly Gln Ala
         50                  55                  60

Ile Arg Ser Lys Ile Glu Asp Gly Thr Val Lys Arg Glu Asp Ile Phe
 65                  70                  75                  80

Tyr Thr Ser Lys Leu Trp Ser Thr Phe His Arg Pro Glu Leu Val Arg
                 85                  90                  95

Ser Cys Leu Glu Lys Thr Leu Lys Asn Ala Gln Leu Asp Tyr Val Asp
            100                 105                 110

Leu Tyr Ile Ile His Phe Pro Met Ala Leu Gln Pro Gly Asp Lys Leu
        115                 120                 125

Phe Pro Arg Asp Glu His Gly Lys Leu Leu Ala Glu Ala Val Asp Leu
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Phe Arg Gln Leu Glu Thr Ile
                165                 170                 175

Leu Asn Lys Pro Gly Leu Lys Tyr Lys Pro Val Cys Asn Gln Val Glu
            180                 185                 190

Cys His Leu Tyr Leu Asn Gln Ser Gln Met Leu Asp Tyr Cys Lys Ser
        195                 200                 205

Lys Asp Ile Ile Leu Val Ser Tyr Cys Thr Leu Gly Ser Ser Arg Asp
    210                 215                 220

Lys Ile Trp Val Asp Gln Lys Ser Pro Val Leu Leu Asp Asp Pro Val
225                 230                 235                 240

Leu Cys Ala Met Ala Asn Lys Tyr Lys Gln Thr Pro Ala Leu Ile Ala
                245                 250                 255
```

```
Ile Arg Tyr Gln Leu Gln Arg Gly Ile Val Val Leu Thr Arg Ser Phe
            260                 265                 270
Lys Glu Lys Arg Ile Lys Glu Phe Met Lys Val Phe Glu Phe Gln Leu
        275                 280                 285
Ala Ser Glu Asp Met Lys Val Leu Asp Gly Leu His Arg Asn Leu Arg
    290                 295                 300
Tyr Asn Thr Ala Ser Tyr Phe Asp Asp His Pro Asn His Pro Phe Thr
305                 310                 315                 320
Asp Glu Tyr

<210> SEQ ID NO 40
<211> LENGTH: 2459
<212> TYPE: DNA
<213> ORGANISM: Mus musculus

<400> SEQUENCE: 40
cagaagtctc aagacctgcg tggttgcatg agtaacaagc tatgaattct gtatccccac      60
gtgtggtact aaacgatggt cacttcatcc ctgcactggg gtttggaacc actgtgcccg     120
ataaggttcc taaggatgaa cttatcaagg ctactaaaat agctatagat actggattcc     180
gccattttga ctccgcttat ttgtaccaaa tagaagagga agtaggccag gccattagaa     240
gcaagattga agatggcact gtgaagagag aagatatatt ctatacttca aagctttgga     300
gcactttcca tcgaccagaa ttggtccgat cttgcttgga aaagacactg aagaatgcac     360
aactggacta tgttgatctt tacattattc atttcccaat ggctttgcag cctggagata     420
aactatttcc acgagacgaa catggaaaac tgttggctga agcagtggat ctctgtgaca     480
catgggaggc catggaaaag tgtaaagatg ccggactggc caagtccatc ggagtgtcga     540
actttaactt caggcagctg gagacgattc tgaacaagcc ggggctcaag tacaagcctg     600
tgtgcaacca ggtagaatgc atctttatt taaaccagag ccaaatgctg gactattgta     660
agtcaaaaga catcattctg gtttcctact gcacattggg aagttcacga gacaaaatct     720
gggtggacca gaaaagtcca gttctcttag atgatccagt tctttgtgcc atggcaaata     780
agtacaagca aacaccagca ctgattgcca ttcgttacca attacagcgt ggaattgtgg     840
tcctgaccag gagtttcaag gagaagcgga tcaaagagtt catgaaggtt tttgaattcc     900
agttggcttc agaggacatg aaagtcctgg atggcttgca cagaaattta agatacaata     960
ctgcgagtta ttttgatgac catcccaatc atccatttac tgatgaatat aacatggtg    1020
gcctttgcca gcatttctat cagaagatct gctgatgcat catgatatga gagatatctt    1080
ggatactggt gactgaacac atcccttctc atcagatcac tgtatctatt aattcacagt    1140
cagatggagc aaagtccaaa gagctatgag ggaagccata ttttgtcac acgctgaaat    1200
ggaacaccat gttgcttttc ctattcttgt gtttttaaag attcatttat tttattttac    1260
atatgtaagt gtacatgtat gtatatctca tgaatgtctg tgtctatgaa gggaagaaga    1320
gagttatagg tcacttggaa ctggagctac ggatgattgt gaatcaccat gtgggcactg    1380
ggagccaaac ctaagtcttc tgttagagca gcaagtgcca ttaaatgccg agccatctca    1440
ttaggtccca ctctaaagat tcttgcctgc tactatttct agaacctcaa tgttttgttt    1500
tcttctgatt tctgacacca acctgttttg ctagaagttt tgggcatgaa gtcattgttg    1560
aagacaatca ttgcaaaggc atctctgggt gggaatttga aggatttttc aacattaagg    1620
gaattaattg ttagtggtta ttgataagta aatattcctc atgtgctttg aggaagaaga    1680
aaatactcca tagctcttcg ctttttctta ttttggaggt aaggcacatg tgaggagtga    1740
```

-continued

```
ccaagagact cagggttctc tccagcaacc caagaaccag agctccaaga gcctggggag    1800
tatgttctcc ttgtgggaaa tttgggaggt tggtaagaag agaactaatc taaaagcatc    1860
atcatggctc agatgtaggg aagttgagaa gaaagctgaa tatgtctctg cttgggaagt    1920 atctttttg  gtaattacat gtgacagtaa aaggaaaatc tacagatttc attcaagaca    1980
gactgctaga ctggatgttt atattttcaa gggattcaga agttgcatta ctgagctatg    2040
ttagaagaaa ccaattcaca tgagtataaa ctccatattc aagttttctc tgatttaaaa    2100
atcggttttc tgaaacatga tctcatatgt ttataggtaa acgagtcaga cttacaaaag    2160
atctcaaagt tactaaattg tatagtcgaa ttaagattaa aagaatatat ttgatgagac    2220
aagttattta aattttcaaa aattatatga aatactgtat ttgaatcagc agtgtttaag    2280
gaagttgtta acatttagtc atctttttg  cacaaagagt atcttcagag aaatcagaga    2340
gaaaagatag tatgtttata gaagattcag aataatgtgg aggtaaatat tgtttagaat    2400
atagttggat ttatatattt cattaataaa tgcctcaaat aagaaaaaaa aaaaaaaaa      2459
```

<210> SEQ ID NO 41
<211> LENGTH: 323
<212> TYPE: PRT
<213> ORGANISM: Mus musculus

<400> SEQUENCE: 41

```
Met Asp Ser Lys Gln Gln Thr Val Arg Leu Ser Asp Gly His Phe Ile
 1               5                  10                  15

Pro Ile Leu Gly Phe Gly Thr Tyr Ala Pro Gln Glu Val Pro Lys Ser
            20                  25                  30

Lys Ala Thr Glu Ala Thr Lys Ile Ala Ile Asp Ala Gly Phe Arg His
        35                  40                  45

Ile Asp Ser Ala Ser Met Tyr Gln Asn Glu Lys Glu Val Gly Leu Ala
    50                  55                  60

Ile Arg Ser Lys Ile Ala Asp Gly Thr Val Lys Arg Glu Asp Ile Phe
65                  70                  75                  80

Tyr Thr Ser Lys Val Trp Cys Thr Phe His Arg Pro Glu Leu Val Arg
                85                  90                  95

Val Cys Leu Glu Gln Ser Leu Lys Gln Leu Gln Leu Asp Tyr Val Asp
            100                 105                 110

Leu Tyr Leu Ile His Phe Pro Met Ala Met Lys Pro Gly Glu Asn Tyr
        115                 120                 125

Leu Pro Lys Asp Glu Asn Gly Lys Leu Ile Tyr Asp Ala Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Lys Ile
                165                 170                 175

Leu Lys Lys Pro Gly Leu Lys Tyr Lys Pro Val Cys Asn Gln Val Glu
            180                 185                 190

Cys His Pro Tyr Leu Asn Gln Gly Lys Leu Leu Asp Phe Cys Arg Ser
        195                 200                 205

Lys Asp Ile Val Leu Val Ala Tyr Ser Ala Leu Gly Ser His Arg Glu
    210                 215                 220

Lys Gln Trp Val Asp Gln Ser Ser Pro Val Leu Leu Asp Asn Pro Val
225                 230                 235                 240

Leu Gly Ser Met Ala Lys Lys Tyr Asn Arg Thr Pro Ala Leu Ile Ala
                245                 250                 255
```

```
Leu Arg Tyr Gln Leu Gln Arg Gly Val Val Leu Ala Lys Ser Phe
            260                 265                 270

Ser Glu Lys Arg Ile Lys Glu Asn Met Gln Val Phe Glu Phe Gln Leu
        275                 280                 285

Thr Ser Glu Asp Met Lys Val Leu Asp Asp Leu Asn Lys Asn Ile Arg
        290                 295                 300

Tyr Ile Ser Gly Ser Ser Phe Lys Asp His Pro Asp Phe Pro Phe Trp
305                 310                 315                 320

Asp Glu Tyr

<210> SEQ ID NO 42
<211> LENGTH: 1178
<212> TYPE: DNA
<213> ORGANISM: Mus musculus

<400> SEQUENCE: 42
atggattcta agcagcagac agtgcgtcta agtgatggtc acttcatccc tatactgggg      60
tttggtacct atgcacctca agaggtacct aagagtaagg ctacagaagc tactaaaata     120
gccatagatg ctggtttccg ccatattgat tctgcttcta tgtatcaaaa tgaaaaggaa     180
gtaggactag ccatccgaag caagatagca gatggcactg tgaagaggga agatatattt     240
tacacatcaa aggtttggtg tacttttcat cgtccagaac tcgtacgggt ctgcttggaa     300
cagtcattga agcaactcca gttggactat gtggacctgt acctcattca tttcccaatg     360
gccatgaagc cgggagaaaa ttatctccca aaagatgaaa atggaaaatt aatatatgat     420
gctgtggata tctgtgacac ctgggaagcc atggagaaat gcaaggatgc aggattggcc     480
aagtccattg gggtgtccaa ctttaaccgc aggcagctgg agaagatcct gaaaaagccg     540
gggctcaagt acaagcctgt gtgcaaccag gtagaatgtc atccttatct caatcaggga     600
aaacttctgg atttctgcag gtcaaaagac attgttctgg ttgcttacag tgctctggga     660
agccatcgtg aaaaacaatg ggttgatcag agctctcctg ttcttttgga taatccagtt     720
cttggctcaa tggcaaaaaa gtacaatcga actcctgcgc tgattgccct tcgctaccag     780
ctacaacgtg gggttgtggt cctcgccaag agtttctctg agaagaggat aaaagagaat     840
atgcaggttt ttgaatttca gttgacttca gaggacatga agtcctcga tgacctgaat     900
aaaaatatcc gatacataag tggttctagc tttaaggacc atcctgattt tccattttgg     960
gatgaatact aactggaggt ccattttgtg ccttgtgcca gatgtcactg cattggaaga    1020
gtgtatagga agagtattct caaaatgtga tgattacata tcaccctaat ccaagcttct    1080
gagcaattct ggctctgctg aatctaccca ttttaaccaa gaaagccaaa actatgtata    1140
tttctccttt ctaagaaata aaagaatcgt tattcttt                            1178

<210> SEQ ID NO 43
<211> LENGTH: 323
<212> TYPE: PRT
<213> ORGANISM: Mus musculus

<400> SEQUENCE: 43

Met Asn Ser Lys Gln Gln Thr Val Leu Leu Asn Asp Gly His Phe Ile
1               5                   10                  15

Pro Ile Leu Gly Phe Gly Thr Ser Ala Pro Gln Glu Val Pro Arg Ser
            20                  25                  30

Lys Ala Thr Glu Ala Thr Lys Ile Ala Ile Asp Ala Gly Phe Arg His
        35                  40                  45
```

| | | | | | | | | | | | |
|---|---|---|---|---|---|---|---|---|---|---|---|
|Ile|Asp|Cys|Ala|Ala|Val|Tyr|Gln|Asn|Glu|Lys|Glu|Val|Gly|Leu|Ala|
|50| | | | |55| | | | |60| | | | | |

Ile Asp Cys Ala Ala Val Tyr Gln Asn Glu Lys Glu Val Gly Leu Ala
 50                  55                  60

Ile Arg Ser Lys Ile Val Asp Gly Thr Val Lys Arg Glu Asp Ile Phe
 65                  70                  75                  80

Cys Thr Ser Lys Val Trp Gln Thr Phe His Arg Pro Glu Leu Val Gln
                 85                  90                  95

Val Cys Leu Glu Gln Ser Leu Lys Gln Leu Gln Leu Asp Tyr Val Asp
            100                 105                 110

Leu Tyr Leu Ile His Phe Pro Ile Ala Met Lys Pro Gly Glu Asn Tyr
            115                 120                 125

Phe Pro Lys Asp Glu Asn Gly Lys Phe Ile Tyr Asp Ala Val Asp Ile
130                 135                 140

Cys Asp Thr Trp Glu Ala Met Glu Lys Cys Lys Asp Ala Gly Leu Ala
145                 150                 155                 160

Lys Ser Ile Gly Val Cys Asn Phe Asn Arg Arg Gln Leu Glu Lys Ile
                165                 170                 175

Leu Ser Lys Pro Gly Leu Lys Tyr Lys Pro Val Cys Asn Gln Val Glu
            180                 185                 190

Cys His Pro Tyr Leu Asn Gln Arg Lys Leu Leu Asp Phe Cys Arg Ser
            195                 200                 205

Lys Asp Ile Val Leu Val Ala His Ser Ala Leu Gly Ser Asn Arg Asp
210                 215                 220

Lys Glu Trp Val Asp Lys Ser Phe Pro Val Leu Leu Asp Asp Pro Val
225                 230                 235                 240

Leu Gly Ser Met Ala Lys Lys Tyr Asn Arg Thr Pro Ala Leu Ile Ala
                245                 250                 255

Leu Arg Tyr Gln Val Gln Arg Gly Val Val Val Leu Ala Lys Ser Phe
            260                 265                 270

Ile Glu Lys Arg Ile Lys Glu Asn Met Gln Val Phe Glu Phe Gln Leu
            275                 280                 285

Thr Ser Val Asp Met Lys Val Leu Asp Gly Leu Asn Lys Asn Ile Arg
290                 295                 300

Tyr Ile Gly Ser Ser Ile Ser Glu Asp His Pro Asp Phe Pro Phe Leu
305                 310                 315                 320

Asp Glu Tyr

<210> SEQ ID NO 44
<211> LENGTH: 1212
<212> TYPE: DNA
<213> ORGANISM: Mus musculus

<400> SEQUENCE: 44
gaggactgag aagccatgaa ttccaagcag cagacagttc ttctaaatga tggtcacttc      60
atccctatac tcgggtttgg tacctctgca cctcaagagg tacctaggag taaggctaca     120
gaagccacca aaatagctat agatgctggt ttccgccata ttgattgtgc tgctgtgtat     180
caaaatgaaa aggaggtagg attagccatc agaagcaaga ttgtagatgg cactgtgaag     240
agggaagata tattttgcac atcaaaggtt tggcaaacat tcatcgtcc agaactggtg      300 caggtatgct tggaacaatc attgaagcaa ctccagttag attatgtgga cctgtacctc     360
attcatttcc caatagccat gaagccagga gagaattatt tcccaaaaga tgagaatgga     420
aaattcatat atgatgcagt ggatatctgt gacacctggg aagccatgga gaaatgcaag     480
gatgcaggat tggccaagtc catcggggtg tgcaacttta accgcaggca gctggagaag     540

```
atcctgagta agccgggggct caagtacaag cctgtgtgca accaggtaga atgtcatcct    600
tatctcaacc agagaaaact tctggatttc tgcaggtcaa aagacattgt tttggttgct    660
catagtgctc tgggaagtaa ccgtgataaa gaatgggtgg acaagagctt cctgttctt    720 ttggatgatc cagttcttgg ctcaatggca aaaaagtaca atcgaacgcc tgcgctgatt    780
gcccttcgct accaggtgca acgtgggggtt gtggtcctag ccaagagttt cattgagaag    840
aggataaaag agaatatgca ggttttttgaa tttcagttga cttcggtgga catgaaagtt    900
cttgatggcc tgaataaaaa tatccgatac ataggtagtt ctatttctga ggaccatcct    960 gatttttccat ttttggatga atactaacat ggaggtccct gtcatgcctt gtgccagaag   1020
tcactacatg ggaagactgt atagaaagga tactctcaaa atgtgatgat tgcatatcac   1080
cctcatccta acttctgagc aattctggct ctgctgagtc tataatctta agcaagaaag   1140
caaaaactat atatatttcc cccttctaa gaaataaaag aatcatttt ctttagcaaa   1200 aaaaaaaaaa aa                                                       1212

<210> SEQ ID NO 45
<211> LENGTH: 323
<212> TYPE: PRT
<213> ORGANISM: Mus musculus

<400> SEQUENCE: 45

Met Asn Ser Lys Cys His Cys Val Ile Leu Asn Asp Gly Asn Phe Ile
 1               5                  10                  15

Pro Val Leu Gly Phe Gly Thr Ala Leu Pro Val Glu Cys Pro Lys Ser
            20                  25                  30

Lys Ala Lys Glu Leu Thr Lys Ile Ala Ile Asp Ala Gly Phe His His
        35                  40                  45

Phe Asp Ser Ala Ser Val Tyr Asn Thr Glu Asp Arg Val Gly Glu Ala
    50                  55                  60

Ile Arg Ser Lys Ile Ala Asp Gly Thr Val Arg Arg Glu Asp Ile Phe
65                  70                  75                  80

Tyr Thr Ser Lys Val Trp Cys Thr Ser Leu Arg Pro Glu Leu Val Arg
                85                  90                  95

Ala Ser Leu Val Arg Ser Leu Gln Lys Leu Gln Phe Asp Tyr Val Asp
            100                 105                 110

Leu Tyr Leu Ile His Tyr Pro Met Ala Leu Lys Pro Gly Glu Glu Asn
        115                 120                 125

Phe Pro Val Asp Glu His Gly Lys Leu Ile Phe Asp Arg Val Asp Leu
    130                 135                 140

Cys Ala Thr Trp Glu Ala Met Glu Lys Cys Lys Asp Ala Gly Leu Thr
145                 150                 155                 160

Lys Ser Ile Gly Val Ser Asn Phe Asn Ser Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Leu Asn Gln Met Lys Leu Leu Asp Phe Cys Lys Ser
        195                 200                 205

Lys Asp Ile Val Leu Val Ala Tyr Gly Val Leu Gly Thr Gln Arg Tyr
    210                 215                 220

Gly Gly Trp Val Asp Gln Asn Ser Pro Val Leu Leu Asp Glu Pro Val
225                 230                 235                 240

Leu Gly Ser Met Ala Lys Lys Tyr Asn Arg Thr Pro Ala Leu Ile Ala
                245                 250                 255
```

-continued

```
Leu Arg Tyr Gln Leu Gln Arg Gly Ile Val Val Leu Asn Thr Ser Leu
                260                 265                 270
Lys Glu Glu Arg Ile Lys Glu Asn Met Gln Val Phe Glu Phe Gln Leu
            275                 280                 285
Ser Ser Glu Asp Met Lys Val Leu Asp Gly Leu Asn Arg Asn Met Arg
        290                 295                 300
Tyr Ile Pro Ala Ala Ile Phe Lys Gly His Pro Asn Trp Pro Phe Leu
305                 310                 315                 320

Asp Glu Tyr

<210> SEQ ID NO 46
<211> LENGTH: 1194
<212> TYPE: DNA
<213> ORGANISM: Mus musculus

<400> SEQUENCE: 46
gtgaaggcaa acatcaagct gagccagctt attttgaaga gggacacata atgaactcca      60
aatgtcattg tgtcatattg aatgatggta acttcattcc agtgctgggt tttggtactg     120
ctcttcctgt agagtgtccc aagagtaaag ctaaggagct caccaaaata gctatagatg     180
ctggtttcca tcactttgat tctgcttctg tctataatac cgaagatcgt gtaggagagg     240
ccatcagaag caagattgct gatggcactg taaggagaga agatatattt tacacctcaa     300
aggtttggtg tactagcctt cgcccagaac ttgtgagagc ttccttggta cggtcactgc     360
aaaaacttca gttcgattat gtggacctgt atctcattca ttacccaatg gccctgaaac     420
caggagaaga aaattttcca gtagatgaac atggaaaatt aatatttgac agagtggacc     480
tctgtgccac ctgggaggcc atggagaagt gtaaggatgc aggactaacc aagtccattg     540
gggtgtctaa ctttaactct agacagttgg agatgattct gaataagcct gggctcaagt     600
acaagccggt atgcaaccag gtagaatgcc atccttatct caaccaaatg aaacttctgg     660
atttctgcaa atcaaaagat attgtattgg ttgcctatgg tgttctagga acacaacgat     720
atggaggatg ggtagaccag aattcccctg ttctcttgga tgaaccagtt cttggttcca     780
tggcaaaaaa atataatcga actccagcct tgattgccct tcgctaccag ttacagcgtg     840
ggattgtggt cctcaacacc agtctcaaag aggagcggat caaagagaac atgcaggttt     900
ttgaattcca gctgagttca gaggatatga agttcttga tggcctgaac agaaatatgc     960
gatacatacc tgctgccatt ttcaagggcc accctaattg gccatttttg gatgaatact    1020
agtatgtgag gatgtctcct gaaaagccta tgagtggaca ctgctcagc tgctgccatc    1080
tacagacttg ccacttctct gtagcaattg agaacttctt gaagataaca aaaagatatc    1140
ataccactct gaaaacaaat aaaagactca ttcttcagca aaaaaaaaaa aaaa          1194

<210> SEQ ID NO 47
<211> LENGTH: 323
<212> TYPE: PRT
<213> ORGANISM: Mus musculus

<400> SEQUENCE: 47

Met Ser Ser Lys Gln His Cys Val Lys Leu Asn Asp Gly His Leu Ile
  1               5                  10                  15
Pro Ala Leu Gly Phe Gly Thr Tyr Lys Pro Lys Glu Val Pro Lys Ser
                 20                  25                  30
Lys Ser Leu Glu Ala Ala Cys Leu Ala Leu Asp Val Gly Tyr Leu His
             35                  40                  45
```

-continued

```
Val Asp Thr Ala Tyr Ala Tyr Gln Val Glu Glu Ile Gly Gln Ala
     50                  55                  60
Ile Gln Ser Lys Ile Lys Ala Gly Val Val Lys Arg Glu Asp Leu Phe
 65                  70                  75                  80
Ile Thr Thr Lys Leu Trp Cys Thr Cys Phe Arg Pro Glu Leu Val Lys
                 85                  90                  95
Pro Ala Leu Glu Lys Ser Leu Lys Leu Gln Leu Asp Tyr Val Asp
            100                 105                 110
Leu Tyr Ile Met His Tyr Pro Val Pro Met Lys Ser Gly Asp Asn Asp
            115                 120                 125
Phe Pro Val Asn Glu Gln Gly Lys Ser Leu Leu Asp Thr Val Asp Phe
130                 135                 140
Cys Asp Thr Trp Glu Arg Leu Glu Glu Cys Lys Asp Ala Gly Leu Val
145                 150                 155                 160
Lys Ser Ile Gly Val Ser Asn Phe Asn His Arg Gln Leu Glu Arg Ile
                165                 170                 175
Leu Asn Lys Pro Gly Leu Lys Tyr Lys Pro Val Cys Asn Gln Val Glu
            180                 185                 190
Cys His Leu Tyr Leu Asn Gln Arg Lys Leu Leu Asp Tyr Cys Glu Ser
            195                 200                 205
Lys Asp Ile Val Leu Val Ala Tyr Gly Ala Leu Gly Thr Gln Arg Tyr
210                 215                 220
Lys Lys Trp Val Asp Gln Asn Ser Pro Val Leu Leu Asn Asp Pro Val
225                 230                 235                 240
Leu Cys Asp Val Ala Lys Lys Asn Lys Arg Ser Pro Ala Leu Ile Ala
                245                 250                 255
Leu Arg Tyr Leu Ile Gln Arg Gly Ile Val Pro Leu Ala Gln Ser Phe
            260                 265                 270
Lys Glu Asn Glu Met Arg Glu Asn Leu Gln Val Phe Gly Phe Gln Leu
            275                 280                 285
Ser Pro Glu Asp Met Lys Thr Leu Asp Gly Leu Asn Lys Asn Phe Arg
290                 295                 300
Tyr Leu Pro Ala Glu Phe Leu Val Asp His Pro Glu Tyr Pro Phe Val
305                 310                 315                 320
Glu Glu Tyr
```

<210> SEQ ID NO 48
<211> LENGTH: 1201
<212> TYPE: DNA
<213> ORGANISM: Mus musculus

<400> SEQUENCE: 48

| | |
|---|---|
| gagacaatga gctccaaaca gcactgtgtc aaactaaatg atggccactt aattcctgcc | 60 |
| ctgggctttg gcacctataa acccaaggag gttcccaaga gtaagtcact ggaggctgca | 120 |
| tgcctagcgc tagatgttgg gtacctccat gttgatactg cttatgcata ccaagtagaa | 180 |
| gaggagatag gacaggccat tcaaagcaag attaaagctg ggttgtaaa gagagaagac | 240 |
| ctgttcatca ctacaaagct tggtgcact tgctttcgac cagagctggt caagcctgcc | 300 |
| ttggaaaagt cactgaaaaa gcttcagctg gattatgttg atctttacat tatgcattac | 360 |
| ccagtgccaa tgaagtcagg ggataatgat tttccagtaa atgagcaagg gaaatctctg | 420 |
| ttggacactg tggatttctg tgacacatgg gagaggttgg aggagtgtaa ggatgcagga | 480 |
| ttggtcaagt ccattggggt gtccaacttt aaccacaggc agctggagcg aatcctcaat | 540 |

```
aagccaggac tgaagtacaa acctgtctgc aaccaggttg aatgtcatct ctatttgaac      600
cagcgtaagc tactggatta ctgcgaatca aaagacattg ttctcgttgc ttacggtgct      660
ctggggaccc agcgatataa aaaatgggtg gaccaaaact ccccagttct cttgaatgat      720
ccagttcttt gtgatgtggc caaaaaaaac aagcgaagtc ctgccttgat tgcacttcga      780
tacctgattc aacgtgggat tgtgcccctg gcccagagtt tcaaagagaa tgagatgaga      840
gagaatttgc aggtttttgg atttcagttg tcccctgagg acatgaaaac actagatggc      900
ctgaacaaaa actttcgata ccttccagca gagttccttg ttgaccaccc agagtatcca      960
tttgtggagg aatattaaca tggggaccta atcatggctt ctgcctgatg tcccctgtgt     1020
gtggacagtg atgctggcaa tatgaccaag atggactgtt ggatggactt gtcatttctg     1080
atcaatcttg gttgcttagc aactcacatt cagctgaagc tttaattaat gatctcaaag     1140
aaatggaata taattttcat gatgctttga aataaatatg aattttctc ttaaaaaaaa     1200 a                                                                     1201
```

<210> SEQ ID NO 49
<211> LENGTH: 323
<212> TYPE: PRT
<213> ORGANISM: Mus musculus

<400> SEQUENCE: 49

```
Met Ser Ser Lys Gln His Tyr Val Lys Leu Asn Asp Gly His Leu Ile
 1               5                  10                  15

Pro Ala Leu Gly Phe Gly Thr Tyr Lys Pro Lys Glu Val Pro Lys Ser
            20                  25                  30

Lys Ser Leu Glu Ala Ala Cys Leu Ala Leu Asp Val Gly Tyr Arg His
        35                  40                  45

Val Asp Thr Ala Tyr Ala Tyr Gln Val Glu Glu Ile Gly Gln Ala
    50                  55                  60

Ile Gln Ser Lys Ile Lys Ala Gly Val Val Lys Arg Glu Asp Leu Phe
65                  70                  75                  80

Val Thr Thr Lys Leu Trp Cys Gly Cys Phe Arg Pro Glu Leu Val Lys
                85                  90                  95

Pro Ala Leu Glu Lys Ser Leu Lys Ser Leu Gln Leu Asp Tyr Val Asp
            100                 105                 110

Leu Tyr Leu Ile His Tyr Pro Val Pro Met Lys Pro Gly Asp Asn Glu
        115                 120                 125

Ser Pro Leu Asp Glu Asn Gly Lys Phe Leu Leu Asp Thr Val Asp Phe
    130                 135                 140

Cys Asp Thr Trp Glu Arg Leu Glu Glu Cys Lys Asp Ala Gly Leu Val
145                 150                 155                 160

Lys Ser Ile Gly Val Ser Asn Phe Asn His Arg Gln Leu Glu Arg Ile
                165                 170                 175

Leu Asn Asn Pro Gly Leu Lys Tyr Lys Pro Val Cys Asn Gln Val Glu
            180                 185                 190

Cys His Leu Tyr Leu Asn Gln Ser Lys Leu Leu Asp Tyr Cys Lys Ser
        195                 200                 205

Lys Asp Ile Val Leu Val Ala Tyr Gly Ala Leu Gly Thr Gln Arg Tyr
    210                 215                 220

Lys Glu Trp Val Asp Gln Asn Ser Pro Val Leu Leu Asn Asp Pro Val
225                 230                 235                 240

Leu Cys Asp Val Ala Lys Arg Asn Lys Arg Ser Pro Ala Leu Ile Ala
                245                 250                 255
```

Leu Arg Tyr Leu Phe Gln Arg Gly Ile Val Pro Leu Ala Gln Ser Phe
            260                 265                 270

Lys Glu Asn Glu Met Arg Glu Asn Leu Gln Val Phe Glu Phe Gln Leu
        275                 280                 285

Ser Pro Glu Asp Met Lys Thr Leu Asp Gly Leu Asn Lys Asn Phe Arg
    290                 295                 300

Tyr Leu Pro Ala Glu Phe Leu Ala Asp His Pro Glu Tyr Pro Phe Ser
305                 310                 315                 320

Glu Glu Tyr

<210> SEQ ID NO 50
<211> LENGTH: 1212
<212> TYPE: DNA
<213> ORGANISM: Mus musculus

<400> SEQUENCE: 50

```
cggtcgacgg acaatgagct ccaaacagca ctatgtcaaa ctaaatgatg ggcacttaat      60
tcctgccctg ggctttggca cctataaacc caaggaggtt cccaagagta agtcactgga     120
ggctgcatgc ctagctctag atgttgggta ccgccatgtt gatactgctt atgcatacca     180
agtagaagag gagataggac aggccattca agcaagatt aaagctgggg ttgtaaagag      240
agaagacctg ttcgtcacta caaagctttg gtgcggttgc tttcgaccag agctggtcaa     300
gcctgctttg gaaaaatcac tgaaaagcct tcagctggat tatgttgatc tttaccttat     360
acattaccca gtgccaatga agccagggga taatgaatct ccattagatg agaacgggaa     420
atttctattg gacactgtgg atttctgtga cacatgggag aggttggagg aatgtaagga     480
tgcaggattg gtcaagtcca ttggggtgtc aactttaac cacaggcagc tagagagaat      540
cctcaacaac ccaggactga agtacaaacc tgtctgcaac caggttgaat gtcatctcta     600
tttgaaccag agtaagctat tggattactg caagtcaaaa gacattgttc ttgttgctta     660
cggtgctctg gggacccagc gatataaaga atgggtggac cagaactccc cagttctctt     720
gaatgatcca gttctttgtg atgtggccaa aaggaacaag cgaagccctg ccctaattgc     780
acttcgatac ctgtttcaac gtgggattgt gcccctggcc cagagtttca agagaatga     840
gatgagagag aatttgcagg ttttgaatt tcagttgtcc cctgaggaca tgaaaacact     900
agatggccta aacaaaaact ttcgatacct tccagcagag ttccttgctg accacccgga     960
gtatccattt tcggaggaat attaacatgg ggcctaatc atggcttctg cctgatgtcc     1020
ctgtgtgtgg acagtgatgc tggcaatatg accaagatgg actgttggat ggacttgtca     1080
tttctgatca atcttggttg cttagcaact cacattcagc tgaagcttta attaatgatc     1140
tcaaagaaat ggaatataat tttcatgatg ctttgaaata aatatgaatt tttctcttaa     1200
aaaaaaaaaa aa                                                         1212
```

<210> SEQ ID NO 51
<211> LENGTH: 301
<212> TYPE: PRT
<213> ORGANISM: Mus musculus

<400> SEQUENCE: 51

Met Glu Asn Ile Pro Thr Val Gly Leu Gly Thr Trp Lys Ala Ser Pro
  1               5                  10                  15

Gly Glu Val Thr Asp Ala Val Lys Leu Ala Ile Asn Leu Gly Tyr Arg
            20                  25                  30

His Phe Asp Cys Ala Tyr Leu Tyr His Asn Glu Ser Glu Val Gly Met
            35                  40                  45

Gly Ile Ser Glu Lys Ile Lys Glu Gly Val Val Lys Arg Glu Asp Leu
        50                  55                  60

Phe Val Val Ser Lys Leu Trp Cys Thr Cys His Lys Lys Ser Leu Val
65                  70                  75                  80

Lys Thr Ala Cys Thr Asn Thr Leu Glu Ala Leu Asn Leu Asp Tyr Leu
                85                  90                  95

Asp Leu Tyr Leu Ile His Trp Pro Ile Gly Phe Lys Pro Gly Glu Lys
            100                 105                 110

Asp Ile Pro Leu Asp Arg Asn Gly Lys Val Ile Pro Ser His Thr Ser
        115                 120                 125

Phe Leu Asp Thr Trp Glu Ala Met Glu Asp Leu Val Phe Glu Gly Leu
    130                 135                 140

Val Lys Asn Leu Gly Val Ser Asn Phe Asn His Glu Gln Leu Glu Arg
145                 150                 155                 160

Leu Leu Asp Lys Pro Gly Leu Arg Val Arg Pro Ile Thr Asn Gln Ile
                165                 170                 175

Glu Cys His Pro Tyr Leu Asn Gln Lys Lys Leu Ile Asp Phe Cys His
            180                 185                 190

Lys Arg Asn Val Ser Val Thr Ala Tyr Arg Pro Leu Gly Gly Ser Gly
        195                 200                 205

Gly Gly Phe His Leu Met Asp Asp Thr Val Ile Arg Lys Ile Ala Lys
    210                 215                 220

Lys His Gly Lys Ser Pro Ala Gln Ile Leu Ile Arg Phe Gln Ile Gln
225                 230                 235                 240

Arg Asn Leu Ile Val Ile Pro Lys Ser Val Thr Pro Ser Arg Ile Arg
                245                 250                 255

Glu Asn Ile Gln Val Phe Asp Phe Glu Leu Thr Glu Lys Asp Met Glu
            260                 265                 270

Glu Leu Leu Ser Leu Asp Lys Asn Leu Arg Phe Ala Thr Phe Pro Thr
        275                 280                 285

Thr Glu Asn His Gln Asp Tyr Pro Phe His Ile Glu Tyr
    290                 295                 300

<210> SEQ ID NO 52
<211> LENGTH: 1675
<212> TYPE: DNA
<213> ORGANISM: Mus musculus

<400> SEQUENCE: 52
gaattcagca cgaggcaaag gggaaccatg gaaaacatcc ctacagtggg cttgggcacc      60
tggaaggcct ccccaggaga agtgactgat gcagttaagt tggctatcaa cctgggctac     120
cggcacttcg attgtgctta cttataccac aatgagagcg aggtgggaat gggaatcagt     180
gagaagatca aggagggcgt ggtgaagaga gaggatctct ttgtagtcag taagctgtgg     240
tgtacctgcc acaagaagtc attggtgaaa acagcatgca ccaataccct ggaagcccta     300
aacttggatt acctggacct ctacctcata cactggccca tcggtttcaa gcctggggaa     360
aaagatatcc ctttggatcg caatggcaag gtcataccca gtcacaccag ctttcttgac     420 acttggagg ccatggagga cctggtgttt gagggtctgg tgaagaacct tggggtgtcc     480
aactttaacc atgaacagct tgagaggctt ttggataagc ctggtttgag ggtcaggccg     540
ataactaacc agattgaatg tcacccatat cttaatcaaa agaagctgat tgattttgc      600

-continued

```
cataaaagaa atgtgtctgt gactgcttac cgtcccctcg gtggctcagg aggtgggttt     660
cacttgatgg atgatactgt cattcgaaag attgcaaaga agcatgggaa gtctcctgct    720
cagattttga tccgatttca gatccaaagg aacttaatag tgatcccccaa atctgtcacc   780
ccaagtcgga ttagagagaa tatccaggta tttgattttg aattaactga aaagatatg    840
gaggaactcc tcagcctaga caagaacctc cgtttcgcca cattcccac aactgaaaat    900
caccaagact atcctttcca catagagtat tgaaacagct tcactcgcca tcatctctgc    960
tcagcagaac cagatcacca agctctgtcc aactctgtaa aggctatgtg gtccctgtgt  1020
gaaccacagc accagacaca gacacagcca agaatgacga acagagtaag aagcaaggaa  1080
atccgtacct agaacagaac cagttcagag aaaaaataaa gacctaggta tgagacaggg  1140
aaagaccatg gaggctgtgg ctgcttccaa gttgttagga atagctgagt gcaaagaata  1200
ttgtaattgt tgtcagttag tcgtagcctt tctggcttct attttcagaa gtgaaatgct  1260
aattgctcac gaattaaaat taccttcaca ttttaagaaa acctgcttga cagaagtgtt  1320
tgaataatat gtaagatttg agaaattagt ataattaata tccatgagat aatttcagta  1380
accacggacc tgaggctgat tgtgtaccta cctccataat tctagatgat atgaagcaaa  1440
tttcctgtat taagagaaga aaggctatgg agactgagac cccagctcag acaaaatgtg  1500
ttttaattt tgttacttaa aaacttctgt gtgactcatt cctacctacc ctactgccat  1560
gcgaatgaga tggaattcca taaaactgat ggtccagaac ttgttcctgt ctgtattatg  1620
agaatataaa gtatcaccat ttttttcctaa aaaaaaaaaa aaaaaaaaac tcgag      1675
```

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence:
      hexahistidine affinity tag

<400> SEQUENCE: 53

His His His His His His
 1               5

<210> SEQ ID NO 54
<211> LENGTH: 200
<212> TYPE: PRT
<213> ORGANISM: Artificial Sequence
<220> FEATURE:
<223> OTHER INFORMATION: Description of Artificial Sequence:poly Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 54

Gly Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

```
Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                 85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 55
<211> LENGTH: 16
<212> TYPE: DNA
<213> ORGANISM: Artificial Sequence
<220> FEATURE:
<223> OTHER INFORMATION: Description of Artificial Sequence:AKR1C1 MGB
      probe
<220> FEATURE:
<221> NAME/KEY: modified_base
<222> LOCATION: (1)
<223> OTHER INFORMATION: n = c modified by 6-fam

<400> SEQUENCE: 55
ntggcttccg ccatat                                                    16

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence:AKR1C1
      forward PCR primer

<400> SEQUENCE: 56
agctttagag gccaccaaat tg                                             22

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence:AKR1C1
      reverse PCR primer

<400> SEQUENCE: 57
aacctgctcc tcattattgt ataaatga                                       28

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence:AKR1C2 MGB
      probe
```

```
<220> FEATURE:
<221> NAME/KEY: modified_base
<222> LOCATION: (1)
<223> OTHER INFORMATION: n = a mosified by 6-fam

<400> SEQUENCE: 58
ngaagccggg ttcca                                                    15

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:AKR1C2
      forward PCR primer

<400> SEQUENCE: 59
ctagaggccg tcaaattggc                                               20

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence:AKR1C2
      reverse PCR primer

<400> SEQUENCE: 60
acctgctcct cattattgta aacatgt                                       27

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:AKR1C3 MGB
      probe
<220> FEATURE:
<221> NAME/KEY: modified_base
<222> LOCATION: (1)
<223> OTHER INFORMATION: n = c modified by 6-fam

<400> SEQUENCE: 61
ntttcaccaa cagatgaa                                                 18

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence:AKR1C3
      forward PCR primer

<400> SEQUENCE: 62
cttattcatt ctccaatgtc tctaaagc                                      28

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence:AKR1C3
      reverse PCR primer

<400> SEQUENCE: 63
tccactatgt caaatattac ttttccattt                                    30
```

-continued

```
<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence:AKR1C4 MGB
      probe

<400> SEQUENCE: 64
atgaaaatgg aaaagtaata ttcgaca                                              27

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:AKR1C4
      forward PCR primer

<400> SEQUENCE: 65
caggtgagac gccactacca                                                      20

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence:AKR1C4
      reverse PCR primer

<400> SEQUENCE: 66
acctcccatg tggcacaga                                                       19
```